US011135223B2

(12) United States Patent
Chae et al.

(10) Patent No.: US 11,135,223 B2
(45) Date of Patent: Oct. 5, 2021

(54) COMPOSITIONS AND METHODS FOR INHIBITING DKK-1

(71) Applicant: YALE UNIVERSITY, New Haven, CT (US)

(72) Inventors: Wook-Jin Chae, New Haven, CT (US); Alfred Bothwell, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 16/071,546

(22) PCT Filed: Jan. 20, 2017

(86) PCT No.: PCT/US2017/014374
§ 371 (c)(1),
(2) Date: Jul. 20, 2018

(87) PCT Pub. No.: WO2017/127706
PCT Pub. Date: Jul. 27, 2017

(65) Prior Publication Data
US 2019/0022094 A1 Jan. 24, 2019

Related U.S. Application Data

(60) Provisional application No. 62/281,778, filed on Jan. 22, 2016.

(51) Int. Cl.
| *A61K 31/506* | (2006.01) |
| *A61K 31/573* | (2006.01) |
| *A61K 31/538* | (2006.01) |
| *C07K 16/18* | (2006.01) |
| *C07K 16/28* | (2006.01) |
| *A61P 11/06* | (2006.01) |
| *A61P 33/02* | (2006.01) |
| *A61K 39/00* | (2006.01) |
| *A61K 45/06* | (2006.01) |

(52) U.S. Cl.
CPC .......... *A61K 31/506* (2013.01); *A61K 31/538* (2013.01); *A61K 31/573* (2013.01); *A61P 11/06* (2018.01); *A61P 33/02* (2018.01); *C07K 16/18* (2013.01); *C07K 16/2896* (2013.01); *A61K 45/06* (2013.01); *A61K 2039/505* (2013.01); *A61K 2300/00* (2013.01); *G01N 2800/24* (2013.01); *Y02A 50/30* (2018.01)

(58) Field of Classification Search
CPC .. A61K 31/506; A61K 31/538; A61K 31/573; A61K 2039/505; A61K 45/06; C07K 16/18; C07K 16/2896; A61P 11/06; A61P 33/02; G01N 2800/24; Y02A 50/30; Y02A 50/41

See application file for complete search history.

(56) References Cited

U.S. PATENT DOCUMENTS

| 2003/0149008 | A1* | 8/2003 | Sahadevan | ........... | A61K 9/0024 514/170 |
| 2009/0285811 | A1* | 11/2009 | Gant | ........... | A61K 31/58 424/133.1 |
| 2010/0298200 | A1* | 11/2010 | Liu | ........... | A61P 31/12 514/1.1 |
| 2010/0298308 | A1* | 11/2010 | Wu | ........... | A61P 3/00 514/229.8 |
| 2013/0209475 | A1 | 8/2013 | Richards | | |

FOREIGN PATENT DOCUMENTS

| WO | 0134180 A2 | 5/2001 | |
| WO | WO-2009026319 A1 * | 2/2009 | ........... C07D 239/26 |
| WO | WO-2015187637 A1 * | 12/2015 | ......... C07K 16/2851 |

OTHER PUBLICATIONS

Beasley et. al., The Lancet, 2015, vol. 386, pp. 1075-1085 (Year: 2015).*
Martinez et. al., J. Bras. Pneumol. 2015, Sociedade Brasileira de Pneumologia e Tisiologia, vol. 41(5), pp. 454-466 (Year: 2015).*
Colditz et. al., Breast Cancer Res. Treat., 2014, NIH, vol. 145(3), pp. 567-579 (1-23) (Year: 2014).*
Kato et. al., J. Immunol., publ. 2007, vol. 179, pp. 1080-1087 (Year: 2007).*
Abbas and Janeway, "Immunology: improving on nature in the twenty-first century," 2000, Cell 100:129-138.
Allen and Wynnn, "Evolution of Th2 immunity: a rapid repair response to tissue destructive pathogens, 2011," PLoS Pathog 7:e1002003 (4 pages).
Barnes, "Immunology of asthma and chronic obstructive pulmonary disease," 2008, Nat Rev Immunol 8:183-92.
Belkaid et al., "The role of interleukin (IL)-10 in the persistence of Leishmania major in the skin after healing and the therapeutic potential of anti-IL-10 receptor antibody for sterile cure," 2001, J Exp Med 194:1497-506.
Bothwell et al., "Regulation of Chronic Lung Inflammation to House Dust Mite Allergen by Wnt Antagonsit," 2015, J Immunol., 194 (1 Supplement):48.1 (5 pages).
Bothwell, A et al., "Cutaneous leishmaniasis is regulated by Wnt antagonist Dkk-1 from activated platelets (MPF7P.715)", 2015, J Immunol 194 (1 Supplement):203.16.
Brott and Sokol, "Regulation of Wnt/LRP signaling by distinct domains of Dickkopf proteins," 2002, Mol Cell Biol 22:6100-10.
Butler, "Shear stress platelet activation," 1995, Lancet 346:841.
Caporaso et al.,"Global patterns of 16S rRNA diversity at a depth of millions of sequences per sample," 2011, PNAS 108(S1):4516-22.
Caporaso et al., "Ultra-high-throughput microbial community analysis on the Illumina HiSeq and MiSeq platforms," 2012, ISME J, 6:1621-4.
Carvalho et al., "Lymph node hypertrophy following Leishmania major infection is dependent on TLR9," 2012, J Immunol 188:1394-401.
Centers for Disease Control, "Vital Signs: Asthma Prevalence, Disease Characteristics, and Self-Management Education—United States, 2001-2009," 2011, MMWR Morb Mortal Wkly Rep 60:547-52.

(Continued)

Primary Examiner — Sarah Pihonak
(74) Attorney, Agent, or Firm — Riverside Law LLP

(57) ABSTRACT

The present invention provides compositions and methods for inhibiting Dkk-1 for treating or preventing an inflammatory or inflammatory-related disease or disorder.

7 Claims, 48 Drawing Sheets

(56) References Cited

OTHER PUBLICATIONS

Cheng et al., "Crystal structures of the extracellular domain of LRP6 and its complex with DKK1," 2011, Nat Struct Mol Biol 18:1204-10.
Chi, "Regulation and function of mTOR signalling in T cell fate decisions," 2012, Nat Rev Immunol 12:325-38.
Choi et al., "Circulating follicular helper-like T cells in systemic lupus erythematosus: association with disease activity," 2015, Arthritis Rheumatol 67:988-99.
Cruciat and Niehrs, Secreted and transmembrane wnt inhibitors and activators, 2013, Cold Spring Harb Perspect Biol 5:a015081 (27 pages).
National Center for Biotechnology Information. PubChem Database. QHLITPHIARVDJI-UHFFFAOYSA-N, CID=25199517, https://pubchem.ncbi.nlm.nih.gov/compound/25199517 (14 pages).
Diacovo et al., "Platelet-mediated lymphocyte delivery to high endothelial venules," 1996, Science 273:252-5.
Diarra et al., "Dickkopf-1 is a master regulator of joint remodeling," 2007, Nat Med 13:156-63.
Ding et al., "Beta-catenin stabilization extends regulatory T cell survival and induces anergy in nonregulatory T cells," 2008, Nat Med 14:162-9.
Divekar and Kita, "Recent advances in epithelium-derived cytokines (IL-33, IL-25, and thymic stromal lymphopoietin) and allergic inflammation," 2015, Curr Opin Allergy Clin Immunol 15:98-103.
Enochson, L et al., "GDF5 reduces MMP13 expression in human chondrocytes via DKK1 mediated canonical Wnt signaling inhibition", Osteoarthritis and Cartilage, (20140000), vol. 22, No. 4, pp. 566-577, XP055400626 [Y] 3-4 *; p. 574, Figure 7A*.
Fahy, "Type 2 inflammation in asthma—present in most, absent in many," 2015, Nat Rev Immunol 15:57-65.
Farrar et al., "An instructive component in T helper cell type 2 (Th2) development mediated by GATA-3," 2001, J Exp Med 193:643-50.
Fukuda et al., "Canonical Wnts and BMPs cooperatively induce osteoblastic differentiation through a GSK3beta-dependent and beta-catenin-independent mechanism," 2010, Differentiation 80:46-52.
Glinka et al., "Dickkopf-1 is a member of a new family of secreted proteins and functions in head induction," 1998, Nature 391:357-62.
Gounari et al, "Loss of adenomatous *Polyposis coli* gene function disrupts thymic development," 2005, Nat Immunol 6:800-9.
Guo et al., "Beta-catenin stabilization stalls the transition from double-positive to single-positive stage and predisposes thymocytes to malignant transformation," 2007, Blood 109:5463-72.
Hebenstreit et al., "LEF-1 negatively controls interleukin-4 expression through a proximal promoter regulatory element," 2008, J Biol Chem 283:22490-22497.
Heikamp et al., "The AGC kinase SGK1 regulates TH1 and TH2 differentiation downstream of the mTORC2 complex," 2014, Nat Immunol 15:457-64.
Ho et al., "The proto-oncogene c-maf is responsible for tissue-specific expression of interleukin-4," 1996, Cell 85:973-83.
Hsu and Scott, "Leishmania mexicana infection induces impaired lymph node expansion and Th1 cell differentiation despite normal T cell proliferation," 2007, J Immunol 179:8200-7.
Huang et al., "The airway microbiome in patients with severe asthma: Associations with disease features and severity," 2015, J Allergy Clin Immunol 136:874-84.
Idzko, "Role of platelets in allergic airway inflammation," 2015, J Allergy Clin Immunol 135:1416-23.
Jenne and Kubes, "Platelets in inflammation and infection," 2015, Platelets 26:286-92.
Joiner et al., "LRP5 and LRP6 in development and disease," 2013, Trends Endocrinol Metab 24:31-39.
Kim et al., "The transcription factor c-Maf controls the production of interleukin-4 but not other Th2 cytokines," 1999, Immunity 10:745-51.
Kim et al., "Wiskott-Aldrich syndrome protein (WASp) controls the delivery of platelet transforming growth factor-β1," 2013, J Biol Chem 288:34352-63.

Koch et al., "The Wnt antagonist Dkk1 regulates intestinal epithelial homeostasis and wound repair," 2011, Gastroenterology 141:259-68.
Krause et al., "An unexpected role for a Wnt-inhibitor: Dickkopf-1 triggers a novel cancer survival mechanism through modulation of aldehyde-dehydrogenase-1 activity," 2014, Cell Death Dis 5:e1093 (12 pages).
Lavine et al., "Insect hemocytes and their role in immunity," 2002, Insect Biochem Mol Biol 32:1295-1309.
Lee et al., "Regulation of IL-4 gene expression by distal regulatory elements and GATA-3 at the chromatin level," 2001, Immunity 14:447-59.
Leon and Ardavin, "Monocyte migration to inflamed skin and lymph nodes is differentially controlled by L-selectin and PSGL-1," 2008, Blood 111:3126-30.
Ley et al., "Getting to the site of inflammation: the leukocyte adhesion cascade updated," 2007, Nat Rev Immunol 7:678-89.
Li et al., "A sensitive flow cytometric assay for circulating platelet-leucocyte aggregates," 1997, Br. J Haematol 99:808-16.
Li et al., "Crosstalk between platelets and the immune system: old systems with new discoveries," 2012, Adv Hematol 2012:384685 (15 pages).
Maier et al., "Inhibition of suppressive T cell factor 1 (TCF-1) isoforms in naive CD4+ T cells is mediated by IL-4/STAT6 signaling," 2011, J Biol Chem 286:919-28.
McGrath et al., "A mechanobiological investigation of platelets," 2011, Biomech Model Mechanobiol 10:473-84.
Moncada et al., "Pharmacologic protein kinase Cα inhibition uncouples human platelet-stimulated angiogenesis from collagen-induced aggregation," 2013, J Pharmacol Exp Ther 345:15-24.
Morrell et al., "Emerging roles for platelets as immune and inflammatory cells," 2014, Blood 123:2759-67.
Notani et al., "Global regulator SATB1 recruits beta-catenin and regulates T(H)2 differentiation in Wnt-dependent manner," 2010, PLoS Biol 8:e1000296 (23 pages).
Pelletier et al., "(1-(4-(Naphthalen-2-yl)pyrimidin-2-yl)piperidin-4-yl)methanamine: a wingless beta-catenin agonist that increases bone formation rate," 2009, J Med Chem 52:6962-5.
Pene et al., "IgE production by normal human lymphocytes is induced by interleukin 4 and suppressed by interferons gamma and alpha and prostaglandin E2," 1988, PNAS 85:6880-4.
Pitchford et al., "Platelet P-selectin is required for pulmonary eosinophil and lymphocyte recruitment in a murine model of allergic inflammation," 2005, Blood 105:2074-81.
Pulendran and Artis, "New paradigms in type 2 immunity," 2012, Science 337:431-5.
Redpath et al., "Protection and pathology during parasite infection: IL-10 strikes the balance," 2014, Parasite Immunol 36:233-52.
Reiner and Locksley, "The regulation of immunity to Leishmania major," 1995, Annu Rev Immunol 13:151-77.
Rondina and Garraud, "Emerging evidence for platelets as immune and inflammatory effector cells," 2014, Front Immunol 5:653.
Sato et al., "Wnt inhibitor Dickkopf-1 as a target for passive cancer immunotherapy," 2010, Cancer Res 70:5326-36.
Scott, "IFN-gamma modulates the early development of Th1 and Th2 responses in a murine model of cutaneous leishmaniasis," 1991, J Immunol 147:3149-55.
Semple et al., "Platelets and the immune continuum," 2011, Nat. Rev. Immunol. 11:264-74.
Shi et al., "Platelet factor 4 limits Th17 differentiation and cardiac allograft rejection," 2014, J Clin Invest 124:543-52.
Staal et al., "WNT signalling in the immune system: WNT is spreading its wings," 2008, Nat Rev Immunol 8:581-93.
Tacchini-Cottier et al., "Does T helper differentiation correlate with resistance or susceptibility to infection with L. major? Some insights from the murine model," 2012, Front Immunol 3:32 (9 pages).
Tamagawa-Mineoka et al., "The role of platelets in leukocyte recruitment in chronic contact hypersensitivity induced by repeated elicitation," 2007, Am J Pathol 170:2019-29.
Tang et al., "Glucose and collagen regulate human platelet activity through aldose reductase induction of thromboxane," 2011, J Clin Invest 121:4462-76.

(56) References Cited

OTHER PUBLICATIONS

Thornbrun et al., "Evidence that asthma is a developmental origin disease influenced by maternal diet and bacterial metabolites," 2015, Nat Commun 6:7320 (13 pages).
Tian et al., "The role of the Wnt-signaling antagonist DKK1 in the development of osteolytic lesions in multiple myeloma," 2003, NEJM 349:2483-94.
Trikalinos et al., "Lineage switch of acute lymphocyctic leukaemia with t(4;11)(q21;q23) into acute myeloid leukaemia in an adult patient after allogeneic stem cell transplantation," 2009, Br J Haematol 145:262-4.
Van Loosdregt et al., "Canonical Wnt signaling negatively modulates regulatory T cell function," 2013, Immunity 39:298-310.
Wang et al., "Aberrant activation of the WNT/β-catenin signaling pathway in lupus nephritis," 2014, PLoS One 9:e84852 (7 pages).
Whyte et al., "Wnt signaling and injury repair," 2012, Cold Spring Harb Perspect Biol 4:a008078 (14 pages).
Wood and Jacinto, "*Drosophila melanogaster* embryonic haemocytes: masters of multitasking," 2007, nat Rev Mol Cell Biol. 8:542-51.
Xie et al., "Stabilized beta-catenin extends thymocyte survival by up-regulating Bcl-xL," 2005, J Immunol 175:7981-88.
Yan et al., "Noninvasive analysis of the sputum transcriptome discriminates clinical phenotypes of asthma," 2015, Am J Respir Crit Care Med 191:1116-25.
Zarbock et al., "Complete reversal of acid-induced acute lung injury by blocking of platelet-neutrophil aggregation," 2006, J Clin Invest 116:3211-9.
Zhang et al., "Role of molecular mimicry of hepatitis C virus protein with platelet GPIIIa in hepatitis C-related immunologic thrombocytopenia," 2009, Blood 113:4086-93.

* cited by examiner

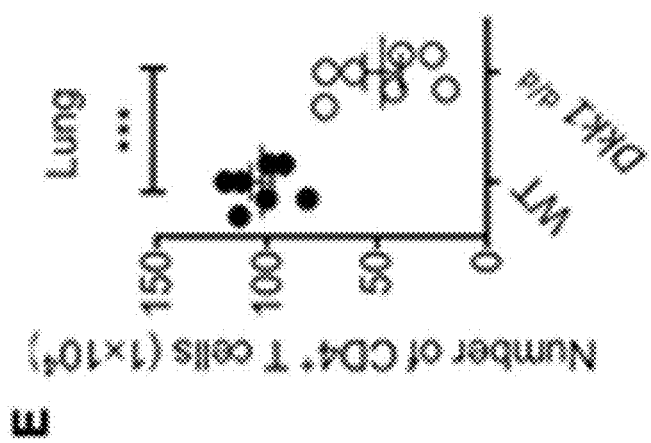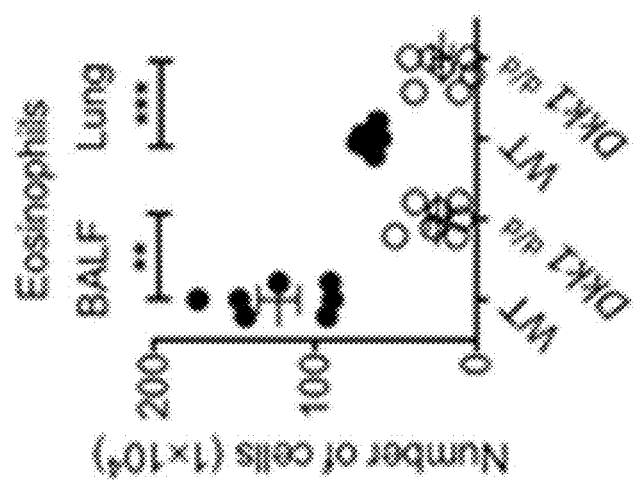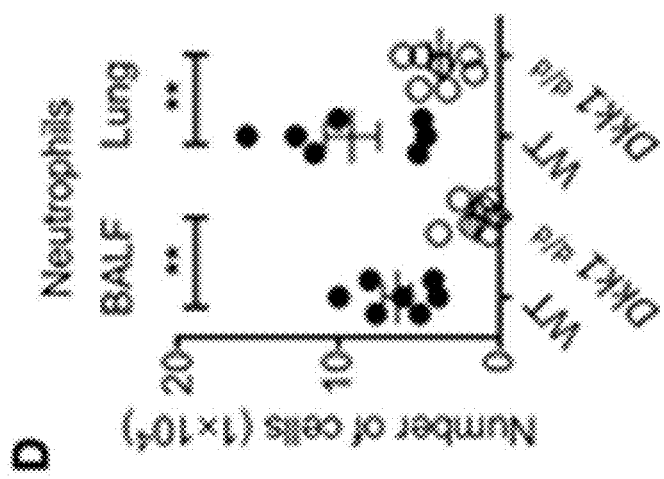
Figure 3D-3E

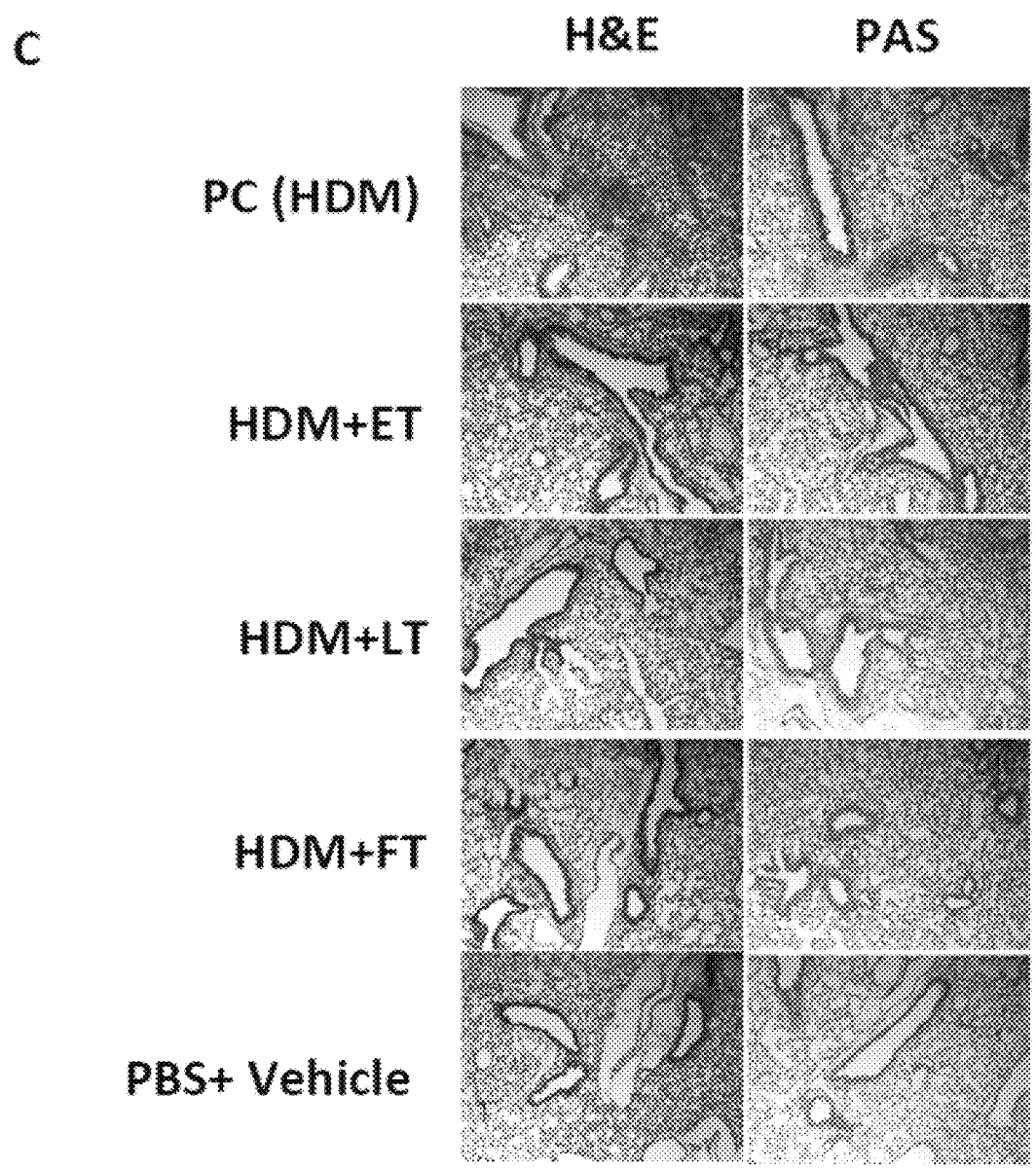

COMPOSITIONS AND METHODS FOR INHIBITING DKK-1

CROSS-REFERENCE TO RELATED APPLICATIONS

This application is a U.S. national phase application filed under 35 U.S.C. § 371 claiming benefit to PCT International Patent Application No. PCT/US2017/014374, filed on Jan. 20, 2017, which claims priority to U.S. Provisional Application No. 62/281,778, filed Jan. 22, 2016, the disclosure of which is incorporated herein by reference in its entirety.

STATEMENT REGARDING FEDERALLY SPONSORED RESEARCH OR DEVELOPMENT

This invention was made with government support under Grant Nos 1R01CA168670-01 and 1R21AI107957-01 and awarded by the National Institutes of Health. The government has certain rights in the invention.

BACKGROUND OF THE INVENTION

The primary goal of immune responses is to eliminate the main trigger of inflammation, contributing to the structural and functional repair of the affected tissue. During the process, the key roles for circulating blood leukocytes are to migrate to sites of infection or injury and to develop polarized immune responses (Abbas and Janeway, 2000, Cell 100:192-138; Ley et al., 2007, Nat Rev Immunol 7:678-89).

Asthma is the most common chronic inflammatory disease of the lung, affects close to 10% of the U.S. and its impact on society is profound (Centers for Disease Control, 2011, MMWR Morb Mortal Wkly Rep 60:547-52). 5-10% of asthmatics have severe or refractory disease making up 25-30 million individuals in the U.S. While the manifestations of asthma are universal, including wheezing and airway obstruction that are caused by airway inflammation, many factors have been hypothesized to influence the development and activity of disease. These include genetic susceptibility and environmental exposures such as diet, medications, air quality, geography, and the endogenous microbiome (Huang et al., 2015, J Allergy Clin Immunol 136:874-84; Thornbrun et al., 2015, Nat Commun 6:7320). Research investigations over the last 25 years have identified type 2 inflammation as a driving immunological response in many individuals with asthma (Fahy, 2015, Nat Rev Immunol 14:57-65). Yet, all individuals with a propensity to develop $T_H2$ immune responses do not become asthmatic. Thus, other factors modulate immunity to impact on development and persistence of allergic or Th2-driven airway disease. Indeed, many patients have low or no evidence of type 2 inflammation.

The canonical Wnt signaling pathway which induces cell proliferation is utilized for tissue repair processes, and a Wnt antagonist may inhibit or delay such events in chronic inflammatory diseases (Whyte et al., 2012, Cold Spring Harb Perspect Biol 4:a008078). Among the quintessential Wnt inhibitory ligands, Dickkopf-1 (Dkk-1) was originally found regulating head formation of Xenopus Laevis and is known to inhibit the canonical Wnt signaling pathway (Cruciat and Niehrs, 2013, Cold Spring Harb Perspect Biol 5:a015081; Glinka et al., 1998, Nature 391:357-62). The inhibition of canonical Wnt pathway activation by Dkk-1 is achieved by its competitive binding of the receptor LRP (low density lipoprotein receptor)-5/6 complex with markedly higher affinity than its counterpart agonist Wnt3a (Cheng et al., 2011, Nat Struct Mol Biol 18:1204-10; Joiner et al., 2013, Trends Endocrinol Metab 24:31-39).

Elevated Dkk-1 levels in circulating blood have been reported in various types of cancers and bone diseases that are characterized by unhealed tissue lesions (Diarra et al., 2007, Nat Med 13:156-63; Sato et al., 2010, Cancer Res 70:5326-36; Tian et al., 2003, NEJM 349:2483-94). In addition, a previous study reported that the proliferation of intestinal epithelial cells in a DSS-colitis model was enhanced in Dkk-1 hypomorphic doubleridge mice (Dkk-$1^{d/d}$), suggesting an inhibitory role of Dkk-1 in wound repair in a pro-inflammatory microenvironment (Koch et al., 2011, Gastroenterology 141:259-68). A diverse array of environmental stimuli also causes tissue damage and they commonly trigger type 2 inflammation/immune responses both in acute and chronic inflammation (Pulendran and Artis, 2012, Science 337:431-5; Whyte et al., 2012, Cold Spring Harb Perspect Biol 4:a008078). Epithelial cell-derived factors (e.g., TSLP, IL-25, and IL-33) can induce type 2 immune responses (Divekar and Kita, 2015, Curr Opin Allergy Clin Immunol 15:98-103). Cytokines such as IL-4, IL-5, IL-10 and IL-13 are the key features of type 2 immune responses following helper T ($T_H$) 2 cell differentiation (Allen and Wynn, 2011, PLoS Pathog 7:e1002003; Pulendran and Artis, 2012, Science 337:431-5).

The role of the canonical Wnt pathway in T cell biology including T cell development, CD8 memory T cell formation, and regulatory T cell function has been demonstrated in multiple experimental systems with varying results, depending on the model systems used (Ding et al., 2008, Nat Med 14:162-9; Guo et al., 2007, Blood 109:5463-72; van Loosdregt et al., 2013, Immunity 39:298-310; Xie et al., 2005, J Immunol 175:7981-88). While the role of canonical Wnt pathway components such as β-catenin or adenomatous polyposis coli (Apc) were analyzed in these studies, the role of Wnt antagonists including Dkk-1 in the course of type 2 immune responses is poorly understood.

Type 1 and type 2 immune responses describe immune responses which are regulated through specific CD4+ T cells. Type 1 immune responses are regulated by T helper 1 ($T_H1$) cells while type 2 immune responses are regulated by T helper 2 ($T_H2$) cells. While $T_H1$ cells activate an immune response through secreting interleukin-2 (IL-2), interferon-γ (IFNγ) and lymphotoxin-α, $T_H2$ cells secrete IL-4, IL-5 and IL-13 and stimulate type 2 immunity characterized by high antibody titers and eosinophilia. $T_H2$ cells in the lymph nodes and secondary lymphoid organs stimulate follicular B helper T cells ($T_{FH}$) to promote B cell allergen specific IgE production. IgE activates inflammatory pathways in the respiratory tract that lead to asthma, cause disease exacerbations and chronic airway inflammation. Moreover, type 2 immune responses may occur with parasitic infections.

Thus, there is a need in the art for compositions and methods for treating type 2 inflammation and diseases or disorders associated with type 2 inflammation. The present invention satisfies this need.

SUMMARY OF THE INVENTION

In one aspect, the invention provides a composition for treating or preventing type 2 inflammation. In one embodiment, the composition comprises an inhibitor of Dkk-1. In one embodiment, the inhibitor of Dkk-1 is a protein, a peptide, a peptidomemetic, an antibody, a ribozyme, a small molecule chemical compound, a nucleic acid, a vector, or an antisense nucleic acid molecule.

In one embodiment, the inhibitor of Dkk-1 is a small molecule chemical compound. In one embodiment, the small molecule chemical compound is

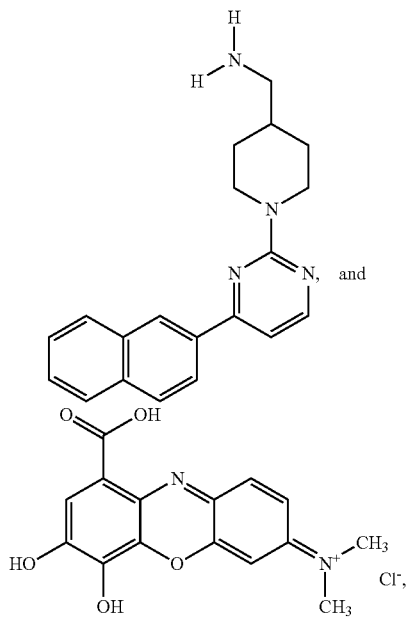

a derivative thereof, or a salt thereof.

In one embodiment, the inhibitor of Dkk-1 is an anti-Dkk-1 antibody.

In one embodiment, the composition further comprises a glucocorticoid.

In one embodiment, the type 2 inflammation is associated with a disease or disorder. In one embodiment the disease or disorder associated with the type 2 inflammation is parasite infection, cutaneous leishmaniasis, or asthma.

In another aspect, the invention provides a method for treating or preventing type 2 inflammation or a type 2 inflammation-related disease or disorder. In one embodiment, the method comprises administering a composition comprising an inhibitor of Dkk-1 to a subject in need thereof. In one embodiment, the inhibitor of Dkk-1 is a protein, a peptide, a peptidomemetic, an antibody, a ribozyme, a small molecule chemical compound, a nucleic acid, a vector, or an antisense nucleic acid molecule.

In one embodiment, the type 2 inflammation-related disease or disorder is a parasite infection, cutaneous leishmaniasis, or asthma.

In one embodiment, the method further comprises administering a second therapeutic agent. In one embodiment, the second therapeutic agent is an inhibitor of type 2 inflammation. In one embodiment, the second therapeutic agent is an asthma therapeutic, a parasite infection therapeutic or a cutaneous leishmaniasis therapeutic.

In one embodiment, the subject is a mammal. In one embodiment, the subject is a human.

BRIEF DESCRIPTION OF THE DRAWINGS

The following detailed description of embodiments of the invention will be better understood when read in conjunction with the appended drawings. It should be understood, however, that the invention is not limited to the precise arrangements and instrumentalities of the embodiments shown in the drawings.

FIG. 1, comprising FIG. 1A depicts flow cytometry analysis of single cell suspensions from spleen of six to ten week-old Dkk-$1^{d/d}$ mice (n=5) and their wildtype littermate controls (n=3). FIG. 1B depicts flow cytometry analysis of single cell suspensions from bone marrow of six to ten week-old Dkk-$1^{d/d}$ mice (n=5) and their wildtype littermate controls (n=3). FIG. 1C depicts ELISA analysis of splenic CD4 T cells isolated by MACS and stimulated with anti-CD3 and anti-CD28 mAb (2 μg/ml) for 4 days. FIG. 1C depicts percentage of cells in peripheral blood from ten to twelve week-old Dkk-$1^{d/d}$ mice (n=5) and their wildtype littermate controls (n=5) measured by HEMAVAT analyzer. WBC (White blood cells), NE (Neutrophils), LY (Lymphocytes), MO (Monocytes), EO (Eosinophils) were counted. FIG. 1D depicts cell number in peripheral blood from ten to twelve week-old Dkk-$1^{d/d}$ mice (n=5) and their wildtype littermate controls (n=5) measured by HEMAVAT analyzer. WBC (White blood cells), NE (Neutrophils), LY (Lymphocytes), MO (Monocytes), EO (Eosinophils) were counted. FIG. 1F depicts airway resistance of Dkk-$1^{d/d}$ and C57Bl/6 mice. The upper panel shows airway resistance measured at day 16 of seven week-old Dkk-$1^{d/d}$ mice (n=3) and their littermate control mice (n=4) challenged with 100 μg HDM extract/mouse on day 0, day 7 and day 14. Control group mice (n=3) were challenged with PBS. The lower panel shows airway resistance measured at day 14 of seven week old C57Bl/6 mice (n=5 each group) challenged with HDM allergen. Dkk-1 inhibitor (10 mg/kg) was injected intraperitoneally at day −1, +1, +6, +8, +10, and +12. Student's t-test was used. n.s, not significant. Small horizontal lines indicate the mean (±s.e.m.). *, p<0.05

FIG. 2, comprising FIG. 2A depicts the ploidy profile of CD41⁻ bone marrow cells assessed by propidium iodide staining (n=6 per genotype) shows no difference between WT and Dkk-$1^{d/d}$ mice. FIG. 2B depicts Total CD41+ bone marrow cellular content is also normal (n=6 per genotype). Flow cytometry of peripheral blood indicates no difference in platelet size under resting conditions. FIG. 2C depicts Dkk-$1^{d/d}$ platelets can be activated and expose surface P-selectin in response to thrombin and ADP+U-46619. FIG. 2D depicts Dkk-$1^{d/d}$ platelets can activate the αIIbβ—receptor in response to ADP. FIG. 2E depicts Dkk-$1^{d/d}$ platelets can activate the αIIbβ—receptor in response to ADP comparable levels to WT. FIG. 2F depicts Platelet cytoskeletal architecture assessed by β-tubulin and phallodin (actin) is normal in Dkk-$1^{d/d}$ mice. FIG. 2G depicts the platelet count and MPV (mean platelet volume) measured from ten to twelve week-old Dkk-$1^{d/d}$ mice (n=5) and wildtype littermate control (n=5) mice. n.s. not significant. Student's t-test was performed Small horizontal lines indicate the mean (±s.e.m.). A representative of two independent experiments are shown.

FIG. 3, comprising FIG. 3A through FIG. 3I, depicts results of experiments showing reduced expression of Dkk-1 protects the host from house dust mite (HDM)-induced asthma. FIG. 3A depicts circulating levels of Dkk-1 in eight-week-old female Dkk-$1^{d/d}$ mice (n=5) and their wildtype (WT) littermate control mice (n=5). FIG. 3B depicts a scheme of HDM challenge protocol (10 μg/mouse/time). FIG. 3C depicts quantitation of total leukocytes (CD45+), neutrophils and eosinophils from BALF (Broncho alveolar lavage fluid) in nine to twelve-week old Dkk-$1^{d/d}$ (n=7) and their littermate controls (n=7). FIG. 3D depicts quantitation of total leukocytes (CD45+), neutrophils and eosinophils from lung tissue homogenates in nine to twelve-week old Dkk-1$^{d/d}$ (n=7) and their littermate controls (n=7). FIG. 3E depicts quantitation of CD4 T cells from lung tissue homogenates. FIG. 3F depicts ELISA quantitation of supernatants from mediastinal lymph node cells that were stimulated with HDM extract for 4 days. FIG. 3G depicts the scoring of lung tissues from each mouse were scored after H&E staining. FIG. 3H depicts the scoring of lung tissues from each mouse were scored after PAS staining. FIG. 3I depicts H&E and PAS staining of lung tissues from WT+PBS mice, WT+HDM mice and Dkk-1$^{d/d}$+HDM mice.

FIG. 4, comprising FIG. 4A depicts a schematic diagram for Dkk-1 inhibitor treatment (10 µg/kg/time) in six-week-old female BALB/c mice. FIG. 4B depicts analysis of parasite burden in the infected foot from each mouse at day 42. FIG. 4C depicts the lesion size in the infected foot from each mouse at day 42. FIG. 4D depicts the cell count of macrophages in the infected hindfoot of mice two weeks after vehicle (n=5) or Dkk-1 inhibitor treatment (n=5) counted by flow cytometry and compared with infected (untreated) and uninfected BALB/c mice (n=3). FIG. 4E depicts results of draining lymph node cells from each mouse (n=5/group) that were stimulated with sLMAG (soluble leishmania antigen) 2 weeks after infection. FIG. 4F depicts results of draining lymph node cells from each mouse (n=5/group) were stimulated with sLMAG 6 weeks after infection. FIG. 4G depicts the CD4 cell percentage in draining lymph nodes from each group was determined by flow cytometry. FIG. 4H depicts CD4 T cell numbers in draining lymph nodes from each group was determined by flow cytometry. A representative of two independent experiments is shown. Student's t-test and one-way-ANOVA analysis with Dunnet's post-hoc test were performed. **, $p<0.005$, *, $p<0.05$.

FIG. 5, comprising FIG. 5A depicts lungs harvested for immunohistochemistry of CD3 (dark brown), CD41 (blue) and isotype control antibodies of lungs from Dkk-1$^{d/d}$ mice and their wildtype littermate controls challenged with HDM extract allergen. Orange arrowheads in the images indicate co-localized CD3 T cells with CD41$^+$ platelets. FIG. 5B depicts ELISA analysis of Dkk-1 from plasma samples from Dkk-1$^{d/d}$ mice (n=5) collected 24 hours after challenge with 50 µg HDM. FIG. 5C depicts ELISA analysis of splenic CD4 T cells from 6-8 week-old C57BL/6 mice were activated with anti-CD3 and anti-CD28 antibodies (Act) with or without Dkk-1 (30 ng/ml unless indicated) for 4 days. FIG. 5D depicts flow cytometry analysis of splenic CD4 T cells from 6-8 week-old C57BL/6 mice were activated with anti-CD3 and anti-CD28 antibodies (Act) with or without Dkk-1 (30 ng/ml unless indicated) for 4 days. FIG. 5E depicts ELISA analysis of naïve CD4 T cells stimulated anti-CD3 and anti-CD28 antibodies for 96 hr with or without Dkk-1.

FIG. 6, comprising FIG. 6A depicts flow cytometry and ELISA analysis of naïve CD4 T cells were stimulated under $T_H1$ polarization conditions for 96 hours with or without Dkk-1. FIG. 6B depicts flow cytometry and ELISA analysis of naïve CD4 T cells were stimulated under $T_H2$ polarization conditions for 96 hours with or without Dkk-1. FIG. 6C depicts flow cytometry analysis of Foxp3, IL-17A, and IL-10 expression in splenic naïve CD4 T cells isolated and differentiated into iTreg for 5 days with 100 U/ml IL-2 and 1.5 ng/ml TGF-β with or without 30 ng/ml and 3 ng/ml of Dkk-1 treated during the culture. FIG. 6D depicts Gata-3 expression levels of splenic naïve CD4 T cells from 8 week-old C57BL/6 mice treated with Dkk-1 with varying doses of Dkk-1 (50, 30, 7.5 ng/ml) or Wnt3a (20% v/v) for 96 hours in the presence of anti-CD3 and anti-CD28 antibody stimulation. FIG. 6E depicts qPCR results of Tcf7 and Lef1 mRNA harvested from splenic naïve CD4 T cells from 8 week-old C57BL/6 mice stimulated with or without Dkk-1 (30 ng/ml) for 96 hours. All results were statistically non-significant. All experiments are a representative of two to three independent experiments. Student's t-test or one way-ANOVA analysis with Bonferonni's post-hoc test were performed. Small horizontal lines and error bars indicate the mean (±s.e.m.). *, $p<0.0001$, , $p<0.005$, *, $p<0.05$.

FIG. 7, comprising FIG. 7A depicts flow cytometry quantitation of mediastinal lymph node cells from FIG. 3D were stimulated with HDM extract for 4 days and the percentages of Gata-3$^-$ and c-Maf$^+$ in CD4 T cells. FIG. 7B depicts flow cytometry analysis of splenic CD4 T cells from 12-week old Thy1-IL-10 reporter mice activated with or without Dkk-1 (30 ng/ml) for 84 hours. Cells were gated for Thy1$^+$ and Thy1$^-$. FIG. 7C depicts flow cytometry analysis of splenic CD4 T cells activated with or without Dkk-1 or anti-IL-4 mAb (10 µg/ml) for 4 days. FIG. 7D depicts flow cytometry analysis of naïve CD4 T cells were stimulated under $T_H2$ polarization conditions for 96 hours with or without Dkk-1. SGK-1 inhibitor (2 µM) or p38 inhibitor (10 µM) was added at 0 h. FIG. 7E depicts ELISA and flow cytometry analysis of isolated human CD4 T cells from PBMCs from healthy volunteers stimulated with human anti-CD3 mAb (OKT3) and anti-CD28 mAb for 4 days with or without Dkk-1 (30 ng/ml) and SGK-1 inhibitor GSK653094 (2 µM). A representative of three independent experiments is shown. Student's t-test was performed. *, $p<0.0001$, , $p<0.005$, *, $p<0.05$, n.s., not significant. One-way ANOVA analysis with Bonferroni's post-hoc test was performed.

FIG. 8, comprising FIG. 8A depicts ELISA analysis of naïve CD4 T cell differentiated into $T_H2$ cells with or without Dkk-1 (30 ng/ml), SGK-1 inhibitor (2 µM) or p38 inhibitor (10 µM) for 96 hours. FIG. 8B depicts flow cytometry analysis of human naïve CD4 T cells (CD4$^+$CD25$^-$CD45RA$^+$) transduced with SGK-1 shRNA and selected with puromycin (0.5 µg/ml) for 48 hours. The selected cells were stimulated with anti-CD3 mAb (OKT3) and anti-CD28 mAb with or without Dkk-1 for 96 hr. For the last 5 hr of culture, stimulation cocktail (PMA/Ionomycin/Brefeldin A/Monensin) was added. FIG. 8C depicts intracellular staining with antibodies recognizing phospho-S6 kinase of splenic CD4$^+$CD25$^-$ cells from 6 week-old C57BL/6 mice were isolated and activated with anti-CD3 and anti-CD28 mAb (2 µg/ml) with or without Dkk-1 (25 ng/ml) for indicated time points. FIG. 8D depicts intracellular staining with antibodies recognizing phospho-4E-BP1 of splenic CD4$^+$CD25$^-$ cells from 6 week-old C57BL/6 mice were isolated and activated with anti-CD3 and anti-CD28 mAb (2 µg/ml) with or without Dkk-1 (25 ng/ml) for indicated time points. FIG. 8E depicts expression levels of c-Maf and Gata-3 by flow cytometry analysis of splenic CD4 T cells naïve CD4 T cells from either 8 week-old C57Bl/6 or Stat6-deficient mice stimulated with anti-CD3 and anti-CD28 antibody with or without Dkk-1 (30 ng/ml) for 96 hours. FIG. 8F depicts expression levels of c-Maf and Gata-3 by flow cytometry analysis of naïve CD4 T cells from either 8 week-old C57Bl/6 or Stat6-deficient mice stimulated with anti-CD3 and anti-CD28 antibody with or without Dkk-1 (30 ng/ml) for 96 hours. Stat6 inhibitor (1 nM) was added for 96 hours. FIG. 8G depicts ELISA analysis of IL-13. One-Way ANOVA analysis with Dunnet's post-hoc test was performed. ***, $p<0.0005$. A representative of two independent experiments is shown.

FIG. 9, comprising FIG. 9A depicts ELISA analysis of plasma samples from female C57Bl/6 mice challenged with PBS (n=3) or HDM extract (10 μg/challenge/mouse, n=5) as in FIG. 3B. FIG. 9B depicts ELISA analysis of plasma samples from eight-week old female C57BL/6 mice challenged with HDM extract (30 μg/challenge, n=4) or PBS (n=5) for 4 and 24 hr. FIG. 9C depicts immunohistochemistry analysis of lungs harvested from Dkk-1$^{d/d}$ mice (n=7) and their wildtype littermate controls (n=7) challenged with HDM extract as in FIG. 3B. FIG. 9D depicts analysis of peripheral blood collected by cardiac puncture with or without EDTA. FIG. 9E depicts Dkk-1 plasma levels analyzed in eight-week-old female C57BL/6 mice 24 hours after injection with platelet depletion antibody (n=5) or isotype control antibody (n=4). FIG. 9F depicts Dkk-1 levels analyzed in HDM allergen challenged mice as in FIG. 3B, platelets were depleted for 12 hours. FIG. 9G depicts ELISA analysis of Dkk1 plasma levels in 6 week-old C57Bl/6 mice intranasally challenged with bacterial ds DNA from E.coli (B-ds DNA)(30 μg/mouse,n=4), LPS (3 μg/mouse, n=5), CpG-ODN 1585 (25 μg/mouse, n=4), and House Dust Mite (HDM) allergen extract (50 μg/mouse, n=4). Control (n=7) mice were given 20 μl of 0.9% NaCl saline. FIG. 9H depicts analysis of Dkk-1 levels in plasma from female BALB/c mice (6-week old) that were infected with L. major. FIG. 9I depicts analysis of Dkk-1 levels in plasma from 5-week old female BALB/c mice analyzed 72 hours after infection where platelets were depleted 4 hours prior to parasite infection. FIG. 9J depicts analysis of Dkk-1 levels in plasma from female BALB/c mice analyzed 10 weeks after infection where platelets were depleted for 12 hours prior to parasite infection. FIG. 9K depicts analysis of Dkk-1 levels in human platelets from four healthy volunteers activated with sLMAG for 1 hour. S 1-S4 designates each healthy donor. X-axis shows dilution of sLMAG in the culture. 1:50 is equivalent to $1\times10^6$ parasites. FIG. 9L depicts analysis of Dkk-1 levels in human platelets ($1\times10^8$/ml, n=5) were activated with sLMAG (1:50) in the presence of PKCα inhibitor, or PKCβ inhibitor for 1 hour. A representative of two independent experiments is shown. Small horizontal lines indicate the mean (±s.e.m.). Student's t-test, One-way ANOVA with Dunnett's post-hoc test or One-way ANOVA with Bonferroni's post-hoc test were performed. *, $p<0.0005$, , $p<0.005$, *, $p<0.05$.

FIG. 11, comprising FIG. 11A depicts flow cytometry analysis of CD45$^+$ cells in lung homogenates from nine-week old Dkk-1$^{d/d}$ mice and wildtype littermate controls (n=5-6/group) 72 hours after challenge with 30 μg HDM allergen extract. FIG. 11B depicts analysis of percentages of CD45$^+$CD41$^+$ cells in peripheral blood from nine-week old Dkk-1$^{d/d}$ mice and wildtype littermate controls collected at 4 hours and 24 hours after allergen challenge. FIG. 11C depicts flow cytometry analysis of CD45+ cells after Dkk-1 protein (300 ng/mouse) was injected intraperitoneally. FIG. 11D depicts a schematic diagram of Dkk-1 inhibitor treatment protocol for each group (n=5 for each group) in the HDM-induced asthma model. HDM allergen extract (10 μg) was challenged intranasally at the indicated time points. FIG. 11E depicts analysis of CD45$^+$ leukocytes numbers in BALF and Lung after Dkk-1 inhibitor treatment in the HDM-induced asthma model. FIG. 11F depicts analysis of neutrophils, eosinophils, and CD4 T cell numbers in the lungs after Dkk-1 inhibitor treatment in the HDM-induced asthma model. FIG. 11G depicts analysis of the number of CD4 T cells in mediastinal LNs. FIG. 11H depicts ELISA analysis of cytokines after 4 days of stimulation of med LN cells. FIG. 11I depicts scoring of H&E staining. FIG. 11J depicts scoring of PAS staining.

FIG. 12, comprising FIG. 12A depicts AMNIS analysis of peripheral blood from 6-week old C57BL/6 male mice. FIG. 12B depicts flow cytometry analysis of the basal LPA population (CD45$^+$CD41$^+$) Dkk-1$^{d/d}$ mice and their wildtype littermate controls. B-cell and CD4 T cell among CD45$^+$CD41$^+$ cells were monitored at the indicated time points in Dkk-1$^{d/d}$ mice and their wildtype littermate controls challenged with 30 μg HDM extract/mouse. FIG. 12C depicts flow cytometry analysis of LPA formation in total CD45$^+$ cells, CD4 T cells, and neutrophils, in mice injected with Dkk-1 inhibitor (n=5) or DMSO vehicle (n=5) 24 hours prior to infection with L. major. FIG. 12D depicts flow cytometry analysis of peripheral blood at given time points for LPA formation in nine-week old C57BL/6 mice (n=5) injected with 300 ng of Dkk-1. FIG. 12E depicts flow cytometry analysis of PSGL-1 expression in the CD45$^+$ leukocyte population in peripheral blood from FIG. 11B, and FIG. 11C. Mean fluorescence intensity was normalized to unchallenged C57BL/6 mice. Small horizontal lines and error bars indicate the mean (±s.e.m.). A representative of three independent experiments is shown. Student's t-test was performed. *, $p<0.0005$, , $p<0.005$. FIG. 12F depicts flow cytometry analysis of peripheral whole blood was collected and stained with CD41 and CD62P from WT mice (n=8) and Dkk-1d/d mice (n=4) challenged with HDM allergen (10 μg/time) as described in FIG. 3B. Nine-week old C57BL/6 mice (n=3) that were injected with vehicle (PBS) were used as controls. FIG. 12G depicts percentages of LFA-1 high cells in the LPA population from peripheral blood from Dkk-1$^{d/d}$ mice (open circle) and WT mice (closed circle) that were challenged with HDM allergen. Representative flow cytometry plots for ICAM-1 and LFA-1 expression in the LPA population is shown. Normalized MFI for ICAM-1 expression and the percentages of LFA-1 high cells were measured by flow cytometry following injection of 300 ng of Dkk-1 intraperitoneally. Student's t-test was used. Small horizontal lines indicate the mean (±s.e.m.). *, p<0.0005, , p<0.005, n.s., not significant. A representative of two independent experiments are shown.

FIG. 13, comprising FIG. 13A through FIG. 13C, depicts results of experiments showing pharmacological antagonism of Dkk-1 in the HDM-induced asthma model. FIG. 13A depicts neutrophils and eosinophils in BALF. FIG. 13B depicts CD4 T cell percentages in med LNs measured by flow cytometry. FIG. 13C depicts representative images H&E and PAS staining. One-way ANOVA analysis with Dunnet's post-hoc test was performed. **, p<0.005, *, p<0.05.

FIG. 17, comprising FIG. 17A depicts the number lymph node cells were in L. major infected BALB/c mice injected with a Dkk-1 monoclonal antibody or isotype control antibody. BALB/c mice were infected with L. major (2 million parasites/animal) on day 0. Dkk-1 mAb or isotype control antibody (100 μg/injection) was injected intraperitoneally into six-week-old female BALB/c mice on day −1, +1, +3, +5, +7, +9, +11, +14 (n=6). On day 14, mice were sacrificed, and their drained lymph node cells were counted. Student's t-test was performed. *,p<0.05. FIG. 17B depicts the lesion size in BALB/c mice injected with a Dkk-1 monoclonal antibody or isotype control antibody. Six-week-old female BALB/c mice were infected with L.major, and DKK-1 mAb was treated intraperitoneally on day −1, +1, +3, +5, +7, +9, +11, +14, +21 and +28. Lesion size for each mouse was measured on day 12, 22, and 32. Student's t-test was performed. *, p<0.05.

DETAILED DESCRIPTION

Figures 1A, 1B, 1C:
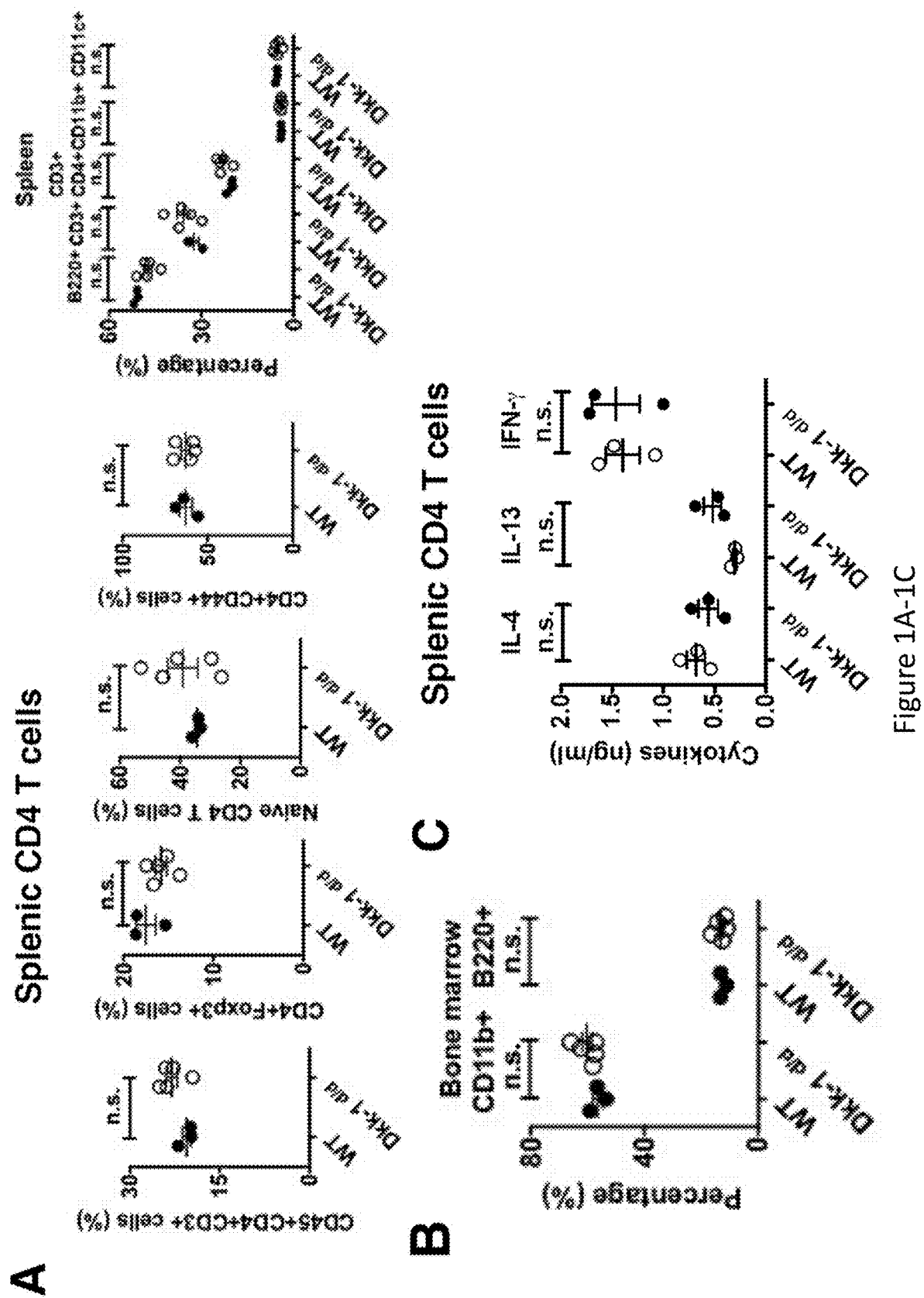
FIG. 1A through FIG. 1F, depicts results of experiments showing the characterization of Dkk-$1^{d/d}$ mice.

The present invention relates to compositions and methods for inhibiting Dkk-1 for inhibiting type 2 inflammation or treating diseases or disorders associated with type 2 inflammation. The invention is based, in part, on the unexpected discovery that Dkk-1 induces $T_H2$ cell polarization in physiologic models of type 2 inflammation or immune responses, and utilizes MAPK and mTOR pathway components to achieve potent $T_H2$ cytokine production. Moreover, platelets are primarily responsible for the circulating Dkk-1 and the level of Dkk-1 is elevated by allergen or non-healing parasite challenge. Dkk-1 promotes interaction between leukocytes and platelets, facilitating the migration of leukocytes to the affected tissue.

In one embodiment, the composition of the invention comprises an inhibitor of Dkk-1. For example, in one embodiment, the inhibitor of Dkk-1 inhibits the expression, activity, or both of Dkk-1.

In one embodiment, the method of the present invention comprises treating or preventing type 2 inflammation. In one embodiment, the method comprises administering to a subject an effective amount of a composition comprising an inhibitor of Dkk-1.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Generally, the nomenclature used herein and the laboratory procedures in cell culture, molecular genetics, organic chemistry, and nucleic acid chemistry and hybridization are those well-known and commonly employed in the art. Standard techniques or modifications thereof are used for chemical syntheses and chemical analyses.

Standard techniques are used for nucleic acid and peptide synthesis. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of a compound which is sufficient to provide a beneficial effect to the subject to which the compound is administered.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

The terms "patient," "subject," "individual," and the like are used interchangeably herein, and refer to any animal, or cells thereof whether in vitro or in vivo, amenable to the methods described herein. In certain non-limiting embodiments, the patient, subject or individual is a human.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "DNA" as used herein is defined as deoxyribonucleic acid.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "fusion polypeptide" refers to a chimeric protein containing a protein of interest (e.g., luciferase) joined to a heterologous sequence (e.g., a non-luciferase amino acid or protein).

The term "homology" refers to a degree of complementarity. There may be partial homology or complete homology (i.e., identity). Homology is often measured using sequence analysis software (e.g., Sequence Analysis Software Package of the Genetics Computer Group. University of Wisconsin Biotechnology Center. 1710 University Avenue. Madison, Wis. 53705). Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

The term "operably linked" as used herein refers to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

An "inducible" promoter is a nucleotide sequence which, when operably linked with a polynucleotide which encodes or specifies a gene product, causes the gene product to be produced substantially only when an inducer which corresponds to the promoter is present.

A "constitutive" promoter is a nucleotide sequence which, when operably linked with a polynucleotide which encodes or specifies a gene product, causes the gene product to be produced in a cell under most or all physiological conditions of the cell.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, a "peptidomimetic" is a compound containing non-peptidic structural elements that is capable of mimicking the biological action of a parent peptide. A peptidomimetic may or may not comprise peptide bonds.

The term "RNA" as used herein is defined as ribonucleic acid.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

The term "recombinant polypeptide" as used herein is defined as a polypeptide produced by using recombinant DNA methods.

As used herein, "conjugated" refers to covalent attachment of one molecule to a second molecule.

As used herein, the term "transdominant negative mutant gene" refers to a gene encoding a polypeptide or protein product that prevents other copies of the same gene or gene product, which have not been mutated (i.e., which have the wild-type sequence) from functioning properly (e.g., by inhibiting wild type protein function). The product of a transdominant negative mutant gene is referred to herein as "dominant negative" or "DN" (e.g., a dominant negative protein, or a DN protein).

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the term "inflammatory" means relating to inflammation. The term "inflammation" refers to the process by which vascular tissues responds to harmful stimuli, such as pathogens, damaged cells, or irritants. "Inflammation includes, but is not limited to secretion of and response to inflammatory factors, e.g., inflammatory cytokines.

The term "antibody," as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from a subject with heavy chain disease, or prepared by the cloning and expression of VH (variable heavy chain immunoglobulin) genes from a subject.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its complementarity-determining regions (CDRs) derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

The term "type 2 inflammation," as used herein means inflammation caused by a type 2 immune response.

The phrase "asthma therapeutic," as used herein means a compound or composition useful in treating asthma and allergic pulmonary inflammation.

The phrase "parasite infection therapeutic," as used herein means a compound or composition useful in treating a parasite infection.

The phrase "cutaneous leishmaniasis therapeutic," as used herein means a compound or composition useful in treating cutaneous leishmaniasis.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for treating type 2 inflammation or a type 2 inflammation-associated disease or disorder.

In one aspect, the present invention provides a composition for treating type 2 inflammation, the composition comprising an inhibitor of Dkk-1.

In one embodiment, the inhibitor of Dkk-1 is selected from a protein, a peptide, a peptidomemetic, an antibody, a ribozyme, a small molecule chemical compound, a nucleic acid, a vector, an antisense nucleic acid molecule.

In one embodiment, the inhibitor of Dkk-1 is a small molecule chemical compound. In another embodiment, the small molecule chemical compound is selected from

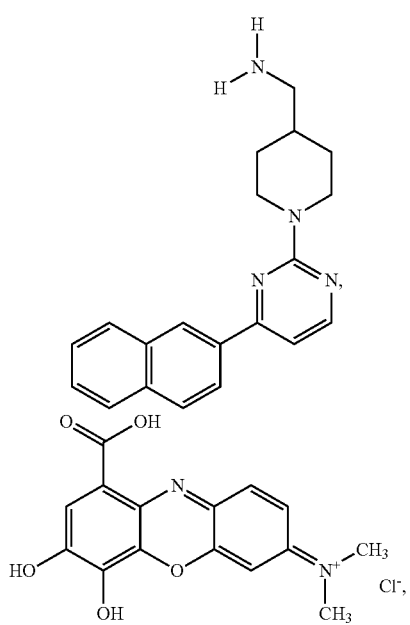

derivatives thereof, and salts thereof.

In one embodiment, the composition further comprises a glucocorticoid.

In one embodiment, the type 2 inflammation is associated with a disease or disorder. In another embodiment, the disease or disorder is selected from the group consisting of a parasite infection, cutaneous leishmaniasis, and asthma.

In another aspect, the invention provides a method for treating or preventing type 2 inflammation or a type 2 inflammation-related disease or disorder. In one embodiment, the method comprises administering a composition comprising an inhibitor of Dkk-1 to a subject in need thereof.

In one embodiment, the inhibitor of Dkk-1 is at least one of the group consisting of a chemical compound, a protein, a peptide, a peptidomemetic, an antibody, a ribozyme, a small molecule chemical compound, a nucleic acid, a vector, an antisense nucleic acid molecule.

In one embodiment, the type 2 inflammation-related disease or disorder is selected from the group consisting of a parasite infection, cutaneous leishmaniasis, and asthma.

In one embodiment method further comprises administering a second therapeutic agent. In certain embodiments, the second therapeutic agent is an inhibitor of type 2 inflammation. In one embodiment the inhibitor of type 2 inflammation is a glucocorticoid. In another embodiment, the second therapeutic agent is an asthma therapeutic, a parasite infection therapeutic and a cutaneous leishmaniasis therapeutic.

In one embodiment, the subject is a mammal. In another embodiment, the mammal is a human.

Inhibitors

In one embodiment, the present invention provides a composition for treating or preventing a disease or disorder associated with type 2 inflammation. In various embodiments, the composition inhibits the expression, activity, or both of Dkk-1 in a subject.

In one embodiment, the composition of the invention comprises an inhibitor of Dkk-1. An inhibitor of Dkk-1 is any compound, molecule, or agent that reduces, inhibits, or prevents the function of Dkk-1. For example, an inhibitor of Dkk-1 is any compound, molecule, or agent that reduces Dkk-1 expression, activity, or both. In one embodiment, an inhibitor of Dkk-1 comprises a nucleic acid, a peptide, a small molecule chemical compound, a siRNA, a ribozyme, an antisense nucleic acid, an antagonist, an aptamer, an antibody, a peptidomimetic, or any combination thereof.

In one embodiment, the composition further comprises a second inhibitor of type 2 inflammation. In one embodiment, the second inhibitor of type 2 inflammation, includes but is not limited to a glucocorticoid, a leukotriene modifier, and a bronchodilator.

Small Molecule Inhibitors

In various embodiments, the inhibitor is a small molecule. In one embodiment, the small molecule chemical compound includes, but is not limited to

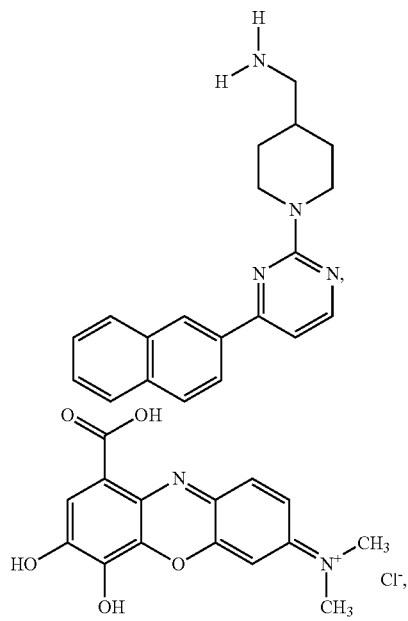

derivatives thereof and salts thereof.

When the inhibitor is a small molecule, a small molecule may be obtained using standard methods known to the skilled artisan. Such methods include chemical organic synthesis or biological means. Biological means include purification from a biological source, recombinant synthesis and in vitro translation systems, using methods well known in the art. In one embodiment, a small molecule inhibitor of the invention comprises an organic molecule, inorganic molecule, biomolecule, synthetic molecule, and the like.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

The small molecule and small molecule compounds described herein may be present as salts even if salts are not depicted and it is understood that the invention embraces all salts and solvates of the inhibitors depicted here, as well as the non-salt and non-solvate form of the inhibitors, as is well understood by the skilled artisan. In some embodiments, the salts of the inhibitors of the invention are pharmaceutically acceptable salts.

Where tautomeric forms may be present for any of the inhibitors described herein, each and every tautomeric form is intended to be included in the present invention, even though only one or some of the tautomeric forms may be explicitly depicted. For example, when a 2-hydroxypyridyl moiety is depicted, the corresponding 2-pyridone tautomer is also intended.

The invention also includes any or all of the stereochemical forms, including any enantiomeric or diasteriomeric forms of the inhibitors described. The recitation of the structure or name herein is intended to embrace all possible stereoisomers of inhibitors depicted. All forms of the inhibitors are also embraced by the invention, such as crystalline or non-crystalline forms of the inhibitors. Compositions comprising an inhibitor of the invention are also intended, such as a composition of substantially pure inhibitor, including a specific stereochemical form thereof, or a composition comprising mixtures of inhibitors of the invention in any ratio, including two or more stereochemical forms, such as in a racemic or non-racemic mixture.

In one embodiment, the small molecule inhibitor of the invention comprises an analog or derivative of an inhibitor described herein.

In one embodiment, the small molecules described herein are candidates for derivatization. As such, in certain instances, the analogs of the small molecules described herein that have modulated potency, selectivity, and solubility are included herein and provide useful leads for drug discovery and drug development. Thus, in certain instances, during optimization new analogs are designed considering issues of drug delivery, metabolism, novelty, and safety.

In some instances, small molecule inhibitors described herein are derivatized/analoged as is well known in the art of combinatorial and medicinal chemistry. The analogs or derivatives can be prepared by adding and/or substituting functional groups at various locations. As such, the small molecules described herein can be converted into derivatives/analogs using well known chemical synthesis procedures. For example, all of the hydrogen atoms or substituents can be selectively modified to generate new analogs. Also, the linking atoms or groups can be modified into longer or shorter linkers with carbon backbones or hetero atoms. Also, the ring groups can be changed so as to have a different number of atoms in the ring and/or to include hetero atoms. Moreover, aromatics can be converted to cyclic rings, and vice versa. For example, the rings may be from 5-7 atoms, and may be homocycles or heterocycles.

As used herein, the term "analog," "analogue," or "derivative" is meant to refer to a chemical compound or molecule made from a parent compound or molecule by one or more chemical reactions. As such, an analog can be a structure having a structure similar to that of the small molecule inhibitors described herein or can be based on a scaffold of a small molecule inhibitor described herein, but differing from it in respect to certain components or structural makeup, which may have a similar or opposite action metabolically. An analog or derivative of any of a small molecule inhibitor in accordance with the present invention can be used to treat type 2 inflammation or a type 2 inflammation-related disease or disorder.

In one embodiment, the small molecule inhibitors described herein can independently be derivatized/analoged by modifying hydrogen groups independently from each other into other substituents. That is, each atom on each molecule can be independently modified with respect to the other atoms on the same molecule. Any traditional modification for producing a derivative/analog can be used. For example, the atoms and substituents can be independently comprised of hydrogen, an alkyl, aliphatic, straight chain aliphatic, aliphatic having a chain hetero atom, branched aliphatic, substituted aliphatic, cyclic aliphatic, heterocyclic aliphatic having one or more hetero atoms, aromatic, heteroaromatic, polyaromatic, polyamino acids, peptides, polypeptides, combinations thereof, halogens, halo-substituted aliphatics, and the like. Additionally, any ring group on a compound can be derivatized to increase and/or decrease ring size as well as change the backbone atoms to carbon atoms or hetero atoms.

Nucleic Acid Inhibitors

In other related aspects, the invention includes an isolated nucleic acid. In some instances the inhibitor is an siRNA, miRNA, or antisense molecule, which inhibits Dkk-1. In one embodiment, the nucleic acid comprises a promoter/regulatory sequence such that the nucleic acid is preferably capable of directing expression of the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York) and as described elsewhere herein.

In another aspect of the invention, Dkk-1 can be inhibited by way of inactivating and/or sequestering Dkk-1. As such, inhibiting the activity of Dkk-1 can be accomplished by using a transdominant negative mutant.

In one embodiment, siRNA is used to decrease the level of Dkk-1 protein. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, Pa. (2003); and Gregory J. Hannon, Ed., RNAi A Guide to Gene Silencing, Cold Spring Harbor Laboratory Press, Cold Spring Harbor, N.Y. (2003). Soutschek et al. (2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of Dkk-1 using RNAi technology.

In another aspect, the invention includes a vector comprising an siRNA or antisense polynucleotide. Preferably, the siRNA or antisense polynucleotide is capable of inhibiting the expression of a target polypeptide, wherein the target polypeptide is selected from the group consisting of Dkk-1. The incorporation of a desired polynucleotide into a vector and the choice of vectors is well-known in the art as described in, for example, Sambrook et al. (2012), and in Ausubel et al. (1997), and elsewhere herein.

In certain embodiments, the expression vectors described herein encode a short hairpin RNA (shRNA) inhibitor. shRNA inhibitors are well known in the art and are directed against the mRNA of a target, thereby decreasing the expression of the target. In certain embodiments, the encoded shRNA is expressed by a cell, and is then processed into siRNA. For example, in certain instances, the cell possesses native enzymes (e.g., dicer) that cleaves the shRNA to form siRNA.

The siRNA, shRNA, or antisense polynucleotide can be cloned into a number of types of vectors as described elsewhere herein. For expression of the siRNA or antisense polynucleotide, at least one module in each promoter functions to position the start site for RNA synthesis.

In order to assess the expression of the siRNA, shRNA, or antisense polynucleotide, the expression vector to be introduced into a cell can also contain either a selectable marker gene or a reporter gene or both to facilitate identification and selection of expressing cells from the population of cells sought to be transfected or infected using a viral vector. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Therefore, in another aspect, the invention relates to a vector, comprising the nucleotide sequence of the invention or the construct of the invention. The choice of the vector will depend on the host cell in which it is to be subsequently introduced. In a particular embodiment, the vector of the invention is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with the present invention to produce polynucleotides, or their cognate polypeptides. Many such systems are commercially and widely available.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence of the invention or the gene construct of the invention can be inserted include a tet-on inducible vector for expression in eukaryote cells.

The vector may be obtained by conventional methods known by persons skilled in the art (Sambrook et al., 2012). In a particular embodiment, the vector is a vector useful for transforming animal cells.

In one embodiment, the recombinant expression vectors may also contain nucleic acid molecules which encode a peptide or peptidomimetic inhibitor of invention, described elsewhere herein.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCRTM, in connection with the compositions disclosed herein (U.S. Pat. Nos. 4,683,202, and 5,928,906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Following the generation of the siRNA polynucleotide, a skilled artisan will understand that the siRNA polynucleotide will have certain characteristics that can be modified to improve the siRNA as a therapeutic compound. Therefore, the siRNA polynucleotide may be further designed to resist degradation by modifying it to include phosphorothioate, or other linkages, methylphosphonate, sulfone, sulfate, ketyl, phosphorodithioate, phosphoramidate, phosphate esters, and the like (see, e.g., Agrwal et al., 1987, Tetrahedron Lett. 28:3539-3542; Stec et al., 1985 Tetrahedron Lett. 26:2191-2194; Moody et al., 1989 Nucleic Acids Res. 12:4769-4782; Eckstein, 1989 Trends Biol. Sci. 14:97-100; Stein, In: Oligodeoxynucleotides. Antisense Inhibitors of Gene Expression, Cohen, ed., Macmillan Press, London, pp. 97-117 (1989)).

Any polynucleotide may be further modified to increase its stability in vivo. Possible modifications include, but are not limited to, the addition of flanking sequences at the 5' and/or 3' ends; the use of phosphorothioate or 2' O-methyl rather than phosphodiester linkages in the backbone; and/or the inclusion of nontraditional bases such as inosine, queuosine, and wybutosine and the like, as well as acetyl-methyl-, thio- and other modified forms of adenine, cytidine, guanine, thymine, and uridine.

In one embodiment of the invention, an antisense nucleic acid sequence which is expressed by a plasmid vector is used to inhibit Dkk-1 protein expression. The antisense expressing vector is used to transfect a mammalian cell or the mammal itself, thereby causing reduced endogenous expression of Dkk-1.

Antisense molecules and their use for inhibiting gene expression are well known in the art (see, e.g., Cohen, 1989, In: Oligodeoxyribonucleotides, Antisense Inhibitors of Gene Expression, CRC Press). Antisense nucleic acids are DNA or RNA molecules that are complementary, as that term is defined elsewhere herein, to at least a portion of a specific mRNA molecule (Weintraub, 1990, Scientific American 262:40). In the cell, antisense nucleic acids hybridize to the corresponding mRNA, forming a double-stranded molecule thereby inhibiting the translation of genes.

The use of antisense methods to inhibit the translation of genes is known in the art, and is described, for example, in Marcus-Sakura (1988, Anal. Biochem. 172:289). Such antisense molecules may be provided to the cell via genetic expression using DNA encoding the antisense molecule as taught by Inoue, 1993, U.S. Pat. No. 5,190,931.

Alternatively, antisense molecules of the invention may be made synthetically and then provided to the cell. Antisense oligomers of between about 10 to about 30, and more preferably about 15 nucleotides, are preferred, since they are easily synthesized and introduced into a target cell. Synthetic antisense molecules contemplated by the invention include oligonucleotide derivatives known in the art which have improved biological activity compared to unmodified oligonucleotides (see U.S. Pat. No. 5,023,243).

In one embodiment of the invention, a ribozyme is used to inhibit Dkk-1 protein expression. Ribozymes useful for inhibiting the expression of a target molecule may be designed by incorporating target sequences into the basic ribozyme structure which are complementary, for example, to the mRNA sequence encoding Dkk-1. Ribozymes targeting Dkk-1 may be synthesized using commercially available reagents (Applied Biosystems, Inc., Foster City, Calif.) or they may be genetically expressed from DNA encoding them.

In one embodiment, the inhibitor of Dkk-1 may comprise one or more components of a CRISPR-Cas system, where a guide RNA (gRNA) targeted to a gene encoding Dkk-1, and a CRISPR-associated (Cas) peptide form a complex to induce mutations within the targeted gene. In one embodiment, the inhibitor comprises a gRNA or a nucleic acid molecule encoding a gRNA. In one embodiment, the inhibitor comprises a Cas peptide or a nucleic acid molecule encoding a Cas peptide.

Polypeptide Inhibitors

In other related aspects, the invention includes an isolated peptide inhibitor that inhibits Dkk-1. For example, in one embodiment, the peptide inhibitor of the invention inhibits Dkk-1 directly by binding to Dkk-1 thereby preventing the normal functional activity of Dkk-1. In another embodiment, the peptide inhibitor of the invention inhibits Dkk-1 by competing with endogenous Dkk-1. In yet another embodiment, the peptide inhibitor of the invention inhibits the activity of Dkk-1 by acting as a transdominant negative mutant.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (v) one in which the polypeptide is fused with another polypeptide, such as a leader or secretory sequence or a sequence which is employed for purification (for example, His-tag) or for detection (for example, Sv5 epitope tag). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

Antibody Inhibitors

The invention also contemplates an inhibitor of Dkk-1 comprising an antibody, or antibody fragment, specific for Dkk-1. That is, can inhibit Dkk-1 to provide a beneficial effect. In one embodiment, the antibody specifically binds to Dkk-1. In one embodiment, the anti-Dkk-1 antibody is a polyclonal antibody. In another embodiment, the anti-Dkk-1 antibody is a monoclonal antibody. In some embodiments, the anti-Dkk-1 antibody is a chimeric antibody. In further embodiments, the anti-Dkk-1 antibody is a humanized antibody. In some embodiments, the antibody is an antibody fragment.

In some embodiments, the antibody is an intact monoclonal or polyclonal antibody, or immunologically portion or active fragment thereof. Thus, in various embodiments, the antibody of invention is a polyclonal antibody, monoclonal antibody, intracellular antibody ("intrabody"), Fv, Fab, Fab', F(ab)2 and F(ab')2, single chain antibody (scFv), heavy chain antibody (e.g., such as a camelid antibody), synthetic antibody, chimeric antibody, or humanized antibodies (see, for example, Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y; Houston et al., 1988, Proc. Natl. Acad. Sci. USA 85:5879-5883; Bird et al., 1988, Science 242:423-426). Antibodies can be prepared using intact polypeptides or fragments containing an immunizing antigen of interest. The polypeptide or oligopeptide used to immunize an animal may be obtained from the translation of RNA or synthesized chemically and can be conjugated to a carrier protein, if desired. Suitable carriers that may be chemically coupled to peptides include bovine serum albumin and thyroglobulin, keyhole limpet hemocyanin. The coupled polypeptide may then be used to immunize the animal (e.g., a mouse, a rat, or a rabbit).

Combinations

Treatments for type 2 inflammation includes glucocorticoids. However, new, specific, type 2 inflammation inhibitors have recently emerged including Omalizumab, Mepolizumab, Benralizumab, Reslizumab, Lebrikizumab, GSK679586, Tralokinumab, and Dupilumab. However, these therapeutics have limited effects.

In one embodiment, the composition of the present invention comprises a combination of a Dkk-1 inhibitor and second therapeutic agent. For example, in one embodiment the second therapeutic agents include, but are not limited to an asthma therapeutic, a parasite infection therapeutic and a cutaneous leishmaniasis therapeutic. In another embodiment, the second therapeutic is an inhibitor of type 2 inflammation. In yet another embodiment, the inhibitor of type 2 inflammation includes, but is not limited to, glucocorticoid, Omalizumab, Mepolizumab, Benralizumab, Reslizumab, Lebrikizumab, GSK679586, Tralokinumab, and Dupilumab.

Exemplary asthma therapeutics include, but are not limited to, corticosteroids such as, Budesonide, Flunisolide, Triamcinolone, Beclomethasone, Fluticasone, Mometasone, Dexamethasone, Hydrocortisone, Methylprednisolone, Prednisone, Cortisone, Betamethasone, or the like. Some other suitable drugs are bronchodilators such as Terbutaline, Albuterol, Ipratropium, Pirbuterol, Epinephrine, Salmeterol, Levalbuterol, Formoterol, Acrivastine, Cetirizine, Loratadine, and Brompheniramine.

Exemplary parasite infection therapeutics include, but are not limited to, Mebendazole, Pyrantel pamoate, Thiabendazole, Diethylcarbamazine, Ivermectin, Niclosamide, Praziquantel, Albendazole Praziquantel, Rifampin, Amphotericin B, Melarsoprol, Eflornithine, Metronidazole Tinidazole, and Miltefosine.

Exemplary cutaneous leishmaniasis therapeutics include, but are not limited to, Amphotericin B, Pentamidine isethionate, paromomycin, and Allopurinol.

In certain embodiments, a composition comprising a combination of inhibitors described herein has an additive effect, wherein the overall effect of the combination is approximately equal to the sum of the effects of each individual inhibitor. In other embodiments, a composition comprising a combination of inhibitors described herein has a synergistic effect, wherein the overall effect of the combination is greater than the sum of the effects of each individual inhibitor.

A composition comprising a combination of inhibitors comprises individual inhibitors in any suitable ratio. For example, in one embodiment, the composition comprises a 1:1 ratio of two individual inhibitors. However, the combination is not limited to any particular ratio. Rather any ratio that is shown to be effective is encompassed.

Therapeutic Methods

The present invention also provides methods of treating or preventing an inflammatory disease or disorder in a subject. In one embodiment, the inflammatory disease or disorder is a type 2 inflammatory disease or disorder. In another embodiment the type 2 inflammatory disease or disorder includes, but is not limited to parasite infection, cutaneous leishmaniasis, asthma, and allergic rhinitis.

It will be appreciated by one of skill in the art, when armed with the present disclosure including the methods detailed herein, that the invention is not limited to treatment of type 2 inflammation that is already established. Particularly, the disease or disorder need not have manifested to the point of detriment to the subject; indeed, the disease or disorder need not be detected in a subject before treatment is administered. That is, significant signs or symptoms of type 2 inflammation do not have to occur before the present invention may provide benefit. Therefore, the present invention includes a method for preventing type 2 inflammation, in that a composition, as discussed previously elsewhere herein, can be administered to a subject prior to the onset of type 2 inflammation, thereby preventing type 2 inflammation.

One of skill in the art, when armed with the disclosure herein, would appreciate that the prevention of type 2 inflammation, encompasses administering to a subject a composition as a preventative measure against the development of, or progression of type 2 inflammation. As more fully discussed elsewhere herein, methods of modulating the level or activity of a gene, or gene product, encompass a wide plethora of techniques for modulating not only the level and activity of polypeptide gene products, but also for modulating expression of a nucleic acid, including either transcription, translation, or both.

The invention encompasses administration of an inhibitor of Dkk-1. To practice the methods of the invention; the skilled artisan would understand, based on the disclosure provided herein, how to formulate and administer the appropriate modulator composition to a subject. The present invention is not limited to any particular method of administration or treatment regimen.

In one embodiment, the method comprises administering to the subject in need an effective amount of a composition that reduces or inhibits the expression or activity of Dkk-1.

One of skill in the art will appreciate that the inhibitors of the invention can be administered singly or in any combination. Further, the inhibitors of the invention can be administered singly or in any combination in a temporal sense, in that they may be administered concurrently, or before, and/or after each other. One of ordinary skill in the art will appreciate, based on the disclosure provided herein, that the inhibitor compositions of the invention can be used to prevent or to type 2 inflammation, and that an inhibitor composition can be used alone or in any combination with another modulator to effect a therapeutic result. In various embodiments, any of the inhibitor compositions of the invention described herein can be administered alone or in combination with other modulators of other molecules associated with type 2 inflammation.

In one embodiment, the invention includes a method comprising administering a combination of inhibitors described herein. In certain embodiments, the method has an additive effect, wherein the overall effect of the administering a combination of inhibitors is approximately equal to the sum of the effects of administering each individual inhibitor. In other embodiments, the method has a synergistic effect, wherein the overall effect of administering a combination of inhibitors is greater than the sum of the effects of administering each individual inhibitor.

The method comprises administering a combination of inhibitors in any suitable ratio. For example, in one embodiment, the method comprises administering two individual inhibitors at a 1:1 ratio. However, the method is not limited to any particular ratio. Rather any ratio that is shown to be effective is encompassed.

Pharmaceutical Compositions and Formulations

The invention also encompasses the use of pharmaceutical compositions of the invention or salts thereof to practice the methods of the invention. Such a pharmaceutical composition may consist of at least one modulator composition of the invention or a salt thereof in a form suitable for administration to a subject, or the pharmaceutical composition may comprise at least one modulator composition of the invention or a salt thereof, and one or more pharmaceutically acceptable carriers, one or more additional ingredients, or some combination of these. The compound or conjugate of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, vagina or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist may design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin. In one embodiment, the pharmaceutically acceptable carrier is not DMSO alone.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an anti-oxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

The regimen of administration may affect what constitutes an effective amount. The therapeutic formulations may be administered to the subject either prior to or after a diagnosis of disease. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to prevent or treat disease. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound;

the state of the disease or disorder, age, sex, weight, condition, general health and prior medical history of the subject being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

The compound may be administered to a subject as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose will be readily apparent to the skilled artisan and will depend upon any number of factors, such as, but not limited to, the type and severity of the disease being treated, the type and age of the animal, etc.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease in a subject.

In one embodiment, the compositions of the invention are administered to the subject in dosages that range from one to five times per day or more. In another embodiment, the compositions of the invention are administered to the subject in range of dosages that include, but are not limited to, once every day, every two, days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any subject will be determined by the attending physical taking all other factors about the subject into account.

Compounds of the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating the same or another disease as that treated by the compositions of the invention) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound or conjugate of the invention, alone or in combination with a second pharmaceutical agent; and instructions for using the compound or conjugate to treat, prevent, or reduce one or more symptoms of a disease in a subject.

The term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating or preventing a disease in a subject, or delivering an imaging or diagnostic agent to a subject.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, are not to be construed as limiting in any way the remainder of the disclosure.

Example 1

The Wnt Antagonist Dickkopf-1 Promotes Pathological Type 2 Inflammation

The data presented herein demonstrates that the Wnt antagonist Dkk-1 induces $T_H2$ cell polarization in physiologic models of type 2 inflammation/immune responses, and utilizes MAPK and mTOR pathway components to achieve potent $T_H2$ cytokine production. Interestingly, platelets were primarily responsible for the circulating Dkk-1 and its level was elevated by allergen or non-healing parasite challenge. Dkk-1 promoted interaction between leukocytes and platelets, facilitating the migration of leukocytes to the affected tissue.

The materials and methods employed in these experiments are now described.

Mice

Mice used in these experiments were C57BL/6J mice (Jackson Laboratory), BALB/c, Doubleridge mice (Dkk-1$^{d/d}$), Foxp3-IRES-RFP mice, Stat6-deficient mice, Thy1-IRES-IL-10 reporter mice, and IL-4-GFP reporter (4Get) mice. were kindly provided by Asma Nusrat (Emory University Thy1-IRES-IL-10 reporter mice were provided by Casey Weaver (University of Alabama). The animals were kept under normal light/dark cycle (12/12).

Antibodies and Reagents

Antibodies used in these experiments were anti-mouse CD4 (clone RM4-5), anti-mouse CD8β (clone eBIOH35-17.2), anti-mouse CD11c (clone N418), anti-mouse CD19 (clone eBio1D3), anti-mouse CD3 (clone eBio500A2), anti-mouse CD11b (clone M1/70), anti-mouse F4/80 (clone BM8), anti-mouse Ly6G (clone 1A8), anti-mouse B220 (clone RA3-6B2), anti-mouse Foxp3 (clone FJK-16s), anti-human/mouse GATA-3 (clone TWAJ), anti-human/mouse c-Maf (clone sym0F1), anti-IL-17A (clone eBio 17B7), anti-IFN-γ (clone XMG1.2), anti-IL-4 (clone 11B11), anti-IL-10 (clone JES5-16E3), anti-CD62L (clone Mel-14), anti-CD69 (clone H12F3), anti-CD25 (clone 7D4), anti-CD44 (clone IM7), Rag IgG2a isotype control (clone eBR2a), anti-CD3 (clone 145-2C11) and anti-CD28 (clone 37.51), anti-mouse CD45 (clone 30-F11), anti-mouse CD41 (clone eBioMWReg30), anti-mouse CD42d (clone 1C2), anti-human/mouse CD62P (clone P.Sel.K02.3), and anti-siglecF (clone ES22-10D8). Inhibitors used in these experiments were SGK1, Dkk1, p38 inhibitor SB203528 and Stat6 inhibitor.

Flow Cytometry, Cell Culture, Cytokine ELISA, Immunohistochemistry

For CD4 T cell differentiation, naïve CD4 T cells (CD4$^+$CD62L$^{hi}$CD44$^{lo}$Foxp3(RFP)-) were isolated from 6-7 week-old Foxp3-IRES-RFP mice. For $T_H1$ differentiation, cells were activated with plate bound anti-CD3 (2 μg/ml), anti-CD28 (2 μg/ml) in the presence of IL-2 (25 U/ml), and IL-12 (20 ng/ml) for 96 hrs in RPMI-1640 media (5% FBS, 1% penicillin/streptomycin and 10 mM HEPES). For $T_H2$ differentiation, cells were activated with plate bound anti-CD3 (2 μg/ml), anti-CD28 (2 μg/ml) in the presence of IL-2 (25 U/ml), anti-IFN-γ (XMG1.2) mAb (10 μg/ml), and IL-4 (100 U/ml) for 96 hrs. For the isolation of CD4 T cells, spleens from 6-7 week-old male Foxp3-IRES-RFP mice were prepared as single cell suspensions. After RBC (red blood cell) lysis, cells were stained with CD16/CD32 FcR (Fc Receptor) blocking antibody (clone 2.4G2). For intracellular staining, cells were stimulated with cell stimulation cocktail with protein transport inhibitors (eBioscience) for 5 hr. Intracellular staining was performed as described in the manufacturer's protocol (eBioscience). A FACS Calibur (BD Biosciences) was used for flow cytometry and data were analyzed by FlowJo software (Treestar).

Cell Lines and Plasmids

Dkk-1 cDNA was cloned into pFRSV-SRα expression vector. Briefly, CHO (Chinese Hamster Ovary) cells were transfected with Dkk-1-pFRSV-SRα and then Dkk-1 expression was amplified by methotrexate (MTX) treatment. Before harvest, MTX was removed and cells were washed. As a control, pFRSV-SRα expression vector was transfected and then the supernatant was also harvested and used in the experiment as a control. The amount of Dkk-1 in the culture supernatant was determined by Dkk-1 ELISA. To determine the biological activity of Dkk-1, Tcf reporter (TOP FLASH) luciferase and Renilla reporter plasmids were cotransfected in HEK 293T cells with Lipofectamine 2000, and then luciferase activity was measured by luciferase assay kit (Promega) after 24 hr of Wnt3a-conditioned media treatment. 10 mM LiCl (Lithium Chloride) was also used to activate Wnt pathway in HEK 293T cells. Luciferase activity was measured using a fluorometer with GEN5 software (Biotek). Dkk-1 was added to inhibit Wnt pathway and relative luciferase activity was measured. A GSK-3β inhibitor BIO was purchased from Sigma. HEK 293T cells were maintained in 10% FBS, 100 U/ml penicillin/streptomycin, 2 mM L-glutamine DMEM media.

Immunohistochemistry

These sections were de-paraffinized by immersion in xylene and re-hydrated. Antigen retrieval was performed using 10 mM sodium citrate buffer. Endogenous peroxidase activity was inhibited by immersion in 3% $H_2O_2$PBS. The sections were blocked for 30 min at room temperature followed by overnight incubation with the specific primary antibody at 4° C. The primary antibodies used were: anti-mouse DKK-1 antibody (R&D Systems), anti-mouse CD41 antibody (clone: MWReg30, Abcam) and anti-CD3c antibody (clone: SP7, Pierce). The sections were rinsed in PBS and incubated with the biotinylated-secondary antibody (Vector Laboratories) for 30 min at room temperature. Sections were washed in PBS and ABC reagent (Vector Laboratories) was added for 30 min at room temperature. Sections were again washed in PBS and bound peroxidase detected by adding DAB substrate (Vector Laboratories) for 15 min at room temperature. Counterstaining was performed using Mayer's haematoxylin for 5 min in Dkk-1 staining.

For double staining, Vectastain-ABC-AP kit (Vector Laboratories) was added for 30 min at room temperature for the second staining. Sections were washed in PBS and incubated with Vector Blue substrate (Vector Laboratories) for 30 min at room temperature in a humid chamber. No counterstaining was used on the double stained slides.

Ploidy/DNA Content Analysis

DNA content analysis was performed as previously described with minor modifications. Briefly, whole bone marrow was stained with FITC-CD41 antibody (BD Biosciences), then fixed with 70% ethanol overnight. Samples were digested for four hours on ice with 200 µg/ml RNase (Sigma-Aldrich), then stained with 10 µg/ml propidium iodide (Sigma-Aldrich). Data was collected on a FACSCalibur (BD Biosciences) and analyzed using FlowJo software (Tree Star).

Platelet Immunofluorescence

Platelet immunofluorescence was performed as previously described with modifications. Blood was collected via the retro-orbital sinus into tubes containing 3.2% sodium citrate (Medicago, Sweden). Platelet-rich plasma was obtained by centrifugation of whole blood at 200×g for 8 min. Platelet-rich plasma was washed (140 mM NaCl, 5 mM KCl, 12 mM Na3C6H5O7, 10 mM dextrose, 12.5 mM sucrose [pH 6.0]) and platelets were isolated at 900 g and resuspended (10 mM HEPES, 140 mM NaCl, 3 mM KCl, 0.5 mM MgCl2, 5 mM NaHCO3, 10 mM dextrose [pH 7.4]). Resting platelets were centrifuged onto poly-L-lysine coated coverslips, fixed (15 min, 4% paraformaldehyde), permeabilized (15 min, 0.5% Triton X-100), and blocked overnight. Coverslips were incubated with anti β-tubulin (1:250; Sigma-Aldrich) for 2-3 hours at room temperature, followed by incubation with secondary antibody (1:500; Life Technologies) and Texas Red-X Phalloidin (Life Technologies) for one hour. After washing, coverslips were mounted with Aqua Poly/Mount (Polysciences, Inc.). Images were captured using an Olympus BX51 microscope with a SensicamQE CCD camera (Cooke) and analyzed using IPLab software (BD, V 4.0.8).

Platelet Activation Flow Cytometry

Peripheral blood was collected from the retro-orbital sinus into tubes coated with lithium heparin (BD). Whole blood was washed three times in Tyrodes-HEPES (1 mM MgCl2, 5 mM HEPES, 140 mM NaCl, 2.7 mM KCl, 5.5 mM dextrose, 0.42 mM Na2HPO4, 12 mM NaHCO3 [pH 7.4]), spinning at 2800 rpm to discard the supernatant. For staining, washed blood was resuspended in Tyrodes-HEPES with 2 mM CaCl2. Platelets were stimulated with 10 µM adenosine 5'-diphosphate (ADP; CHRONO-LOG), 3 µM U-46619 (Cayman Chemical), or 0.1 U/ml Thrombin (Roche), and activation was assessed by CD41/61, JON/A, and Pselectin/CD62P expression (Emfret Analytics). Data was collected on a FACSCalibur (BD Biosciences) and analyzed using FlowJo software (Tree Star).

Human PBMC, HUVEC and Lentiviral Transduction

Healthy frozen human PBMCs were prepared by a Ficoll-Hypaque method. Human CD4 T cells were isolated using a CD4 T cell isolation kit (Miltenyi Biotec) from four independent donors. CD4 T cells were further sorted for naïve and effector T cells. Naïve CD4 T cells were activated for 24 hr with T cell expander kit (Dynalbeads). Lentivirus particles were packaged using HEK 293T cells. At 48 hr T cells were infected with shRNA lentivirus particles (MOI=5). shRNA vector for SGK-1 was purchased from Addgene. Cells were selected with puromycin at 0.3 µg/ml. Selected T cells were further stimulated with anti-CD3 and anti-CD28. IL-10 and Gata-3 were measured by intracellular cytokine staining after stimulating cells with cell stimulation cocktail with protein transport inhibitors (eBioscience) for 5 hr. For Dkk-1 measurement by ELISA, $2 \times 10^6$ frozen PBMCs were thawed and stimulated with soluble leishmania antigen (equivalent to $5 \times 10^6$ parasites/ml) or HDM extract (20 µg/ml) for 24 and 48 hrs. HUVECs (passage 2 to 9) were kindly provided by Jordan Pober (Yale University). Briefly, $2 \times 10^4$ HUVECs were stimulated with sLMAG or HDM for 24 hrs. HUVECs were maintained with M199 media with 20% FCS and ECGS (15 µg/ml).

Human Platelet Isolation and Stimulation

Human platelets were isolated as described from healthy volunteers (Tang et al., 2011). All volunteers consented to donate their blood. Briefly, 3.2% citrate buffer was used to prevent coagulation. Blood was centrifuged at 250 g for 15 min. The upper layer was taken as platelet rich plasma (PRP). The Hemavet 950FS (Drew Scientific) was used to count platelet numbers. Platelets were washed twice with wash buffer and resuspended in Tyrode's buffer. 100 million platelets/ml were used for activation. House dust mite extract (50 µg) added for activation of platelets for 1 hr. For soluble leishmania antigen (sLMAG), L.major parasites were prepared in $5 \times 10^8$ parasites/ml Schneider's culture medium. sLMAG was prepared by repeated freeze and thaw cycles. This stock was added to platelet culture indicated ratio for 1 hr. Platelets were resuspended in Tyrode's buffer. Supernatant was collected for human Dkk-1 ELISA House Dust Mite Asthma Model House dust mite extract (*Dermatophagoides pteronyssinus*; Greer Labs) (10 µg) was dissolved in 20 µl of PBS for each mouse per intranasal challenge. 6-10 week old doubleridge mice and their littermate controls were challenged intranasally on day 0, 7, 8, 9, 10, and 11. Mice were sacrificed on day 14. Broncho-alveolar lavage (BAL) fluid was collected and BAL cells were counted and analyzed by flow cytometry. Mediastinal lymph nodes (medLNs) were harvested and a single cell suspension was prepared. Subsequently, med LNs cells were stimulated with 15 µg/ml of HDM extract for 96 hr. Supernatant was harvested for ELISA assays and cells were analyzed for flow cytometry. Lung homogenate was prepared by collagenase digestion. Cells were counted and lymphocytes were analyzed by flow cytometry. Lymphocytes were gated on CD45⁻ cells. Neutrophils (CD45⁺CD11b⁺Ly6G⁺) and Eosinophils (CD45⁺CD11c⁻SiglecF⁻) in lung tissue homogenates and BAL fluid were measured by flow cytometry. For histological analysis, lungs were fixed with 10% formalin at least for 24 hr, embedded in paraffin and stained with hematoxylin and eosin (H&E), or periodic acid-Schiff (PAS) reagent and were assigned scores by established methods. Peribronchiolar and perivascular inflammation was determined by a semiquantitatively graded scale as follows: 0, no detectable airway inflammation; 1, less than 25% bronchials and surrounding vasculature were found to have either perivascular or peribronchial inflammatory cell infiltration; 2, approximately 25-50% of bronchials and surrounding vasculature were affected; 3, approximately 50-75% bronchials and surrounding vasculature were affected; 4, more than 75% of bronchials and surrounding vasculature were affected. Histology scoring was performed in a double-blinded manner by a certified pathologist.

For lymphocyte-platelet aggregation assay, 50 µg of HDM extract was dissolved in 25 µl PBS and then intranasal challenge was performed. Lymphocyte-platelet aggregation was measured at 4 h and 24 h after the challenge. At 72 h, lung homogenate was prepared by collagenase digestion. Cells were counted and lymphocytes were analyzed by flow cytometry as described above. To assess the effect of Dkk-1 inhibitor, 10 mg/kg/of WAY-262611, in 50 µl vehicle (DMSO) was injected intraperitoneally as described in FIG. 15. For invasive measurement of airway dynamic resistance, mice were anesthetized with urethane, paralyzed using d-tubocurarine, tracheotomized, and intubated with an 18-G catheter, followed by mechanical ventilation with a Flexivent apparatus (SCIREQ). AHR was analyzed using a flexivent apparatus (SCIREQ) seventy-two hours after the final HDM challenge. Mice were analyzed for airway hyperresponsiveness using the mechanical ventilator apparatus in response to PBS or increasing doses of aerosolized methacholine. Relative respiratory system resistance (Rrs) values (cm/H20/ml) were calculated by setting 0 mg/ml (PBS) as 100%.

*Leishmania* Infection Model

*L. major* WR309 strain (MHOM/IL/79/LRC-L251) was originally isolated from a human case of cutaneous leishmaniasis in Israel and has been maintained through culture and frequent passages in mice to maintain virulence. BALB/c mice were infected with 2×10⁶ late stationary promastigotes isolated from a Percoll gradient. For monitoring 2 week and 6 week experiments, Dkk-1 inhibitor (10 mg/kg) or vehicle (50 µl DMSO) was injected on day −1, +1, +3, +5, +7, +9, +11 and weekly afterwards till harvest. Draining lymph nodes, nondraining lymph nodes, and plasma were collected. For ex vivo analysis, soluble Leishmania major antigen (sLMAg) was employed. Single cell suspension of draining and non-draining lymph node cells was incubated with sLMAg (equivalent to 5×10⁶ organisms/ml final) for 96 hr. Supernatants were harvested and analyzed by ELISA assays. For depleting platelets, 80 µg of anti-CD42 mAb (Emfret Analytical) was injected intravenously in 100 µl PBS. Equal amounts of isotype-matched control Ab (eBioscience) was used for control group animals. Tissues from mice were harvested on day 3 post-infection for analysis.

Human/Mouse Platelet Isolation and Functional Characterization, Lymphocyte Platelet Aggregate Assay Human platelets were isolated as described from healthy volunteers (Tang et al., 2011, J Clin Invest 121:4462-76). Lymphocyte-platelet aggregate detection was performed as described previously with minor modifications (Li et al., 2012, Adv Hematol 384685; Pitchford et al., 2005, Blood 105:2074-81). Briefly, 90 µl blood was collected via the retro-orbital sinus into tubes containing 10 µl 0.5 M EDTA (pH 8.0) at 4 and 24 hours after house dust mite extract challenge, *L. major* infection, or recombinant Dkk1 injection. Peripheral blood (8 µl) was stained with anti-CD16/32 antibody for 15 min at room temperature. The peripheral blood was further incubated with each antibody to detect each subset of lymphocyte subset and platelets for 15 min at room temperature in the dark. Fix/red blood cell lysis buffer (Biolegend) (450 µl) was added and incubated for 15 min in the dark. Samples were analyzed by flow cytometry within 4 to 6 hours. Live gating was performed on leukocyte-sized events to exclude single platelets. Leukocytes were identified by their forward and side scatter characteristics and also CD45 expression. Lymphocyte-platelet aggregates were identified by the CD41⁺ population. Each subset of lymphocyte was further gated based on this CD45⁺CD41⁺ population.

Statistical Significance

Statistically significant differences were determined by One-way ANOVA with Bonferroni's post-hoc test, Dunnet's post-hoc test, or student t-test with Graph Pad Prism software (GraphPad Software).

The results of the experiments are now described.

Figures 1D, 1E, 1F:
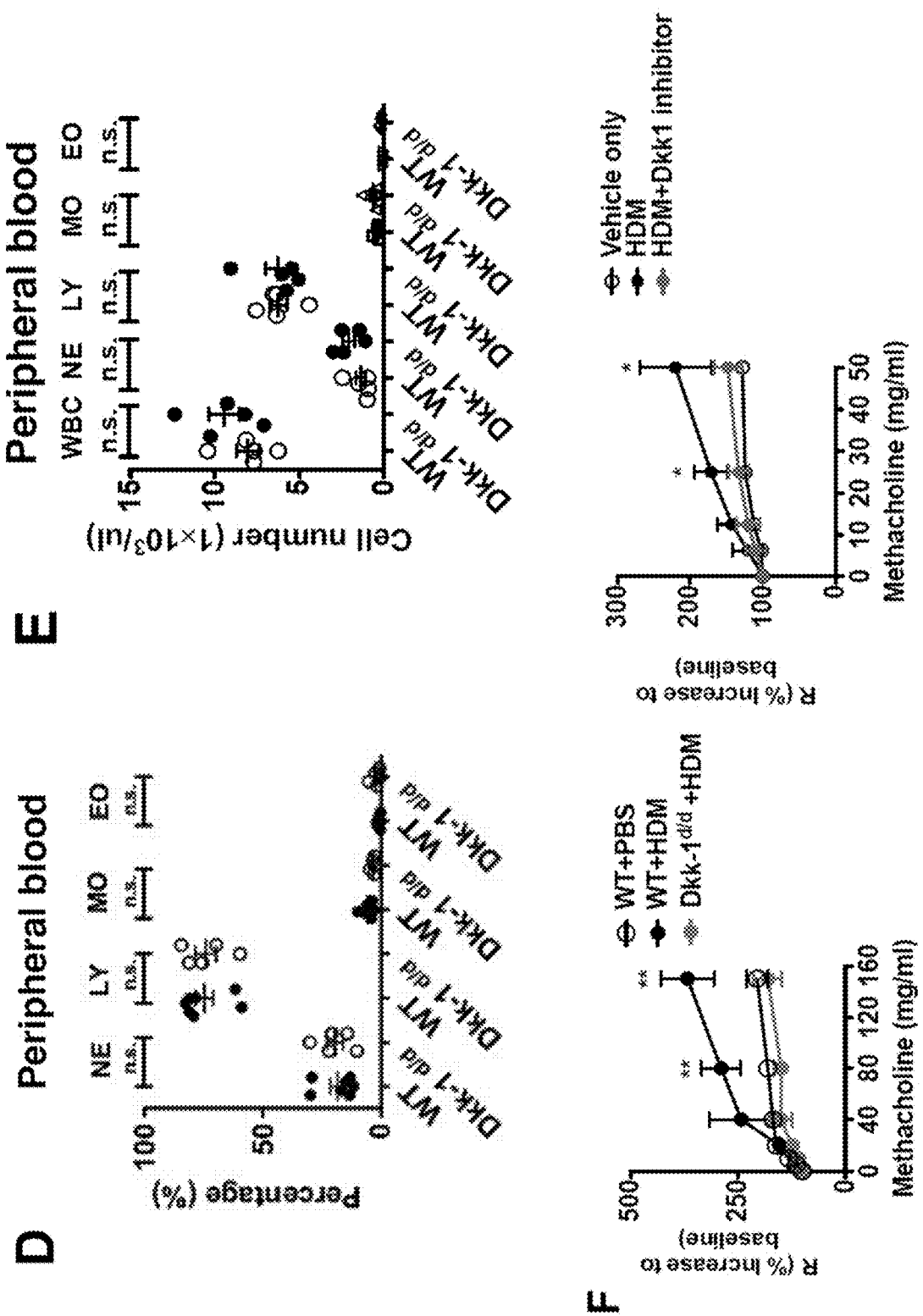
Figures 2A, 2B, 2C, 2D, 2E:
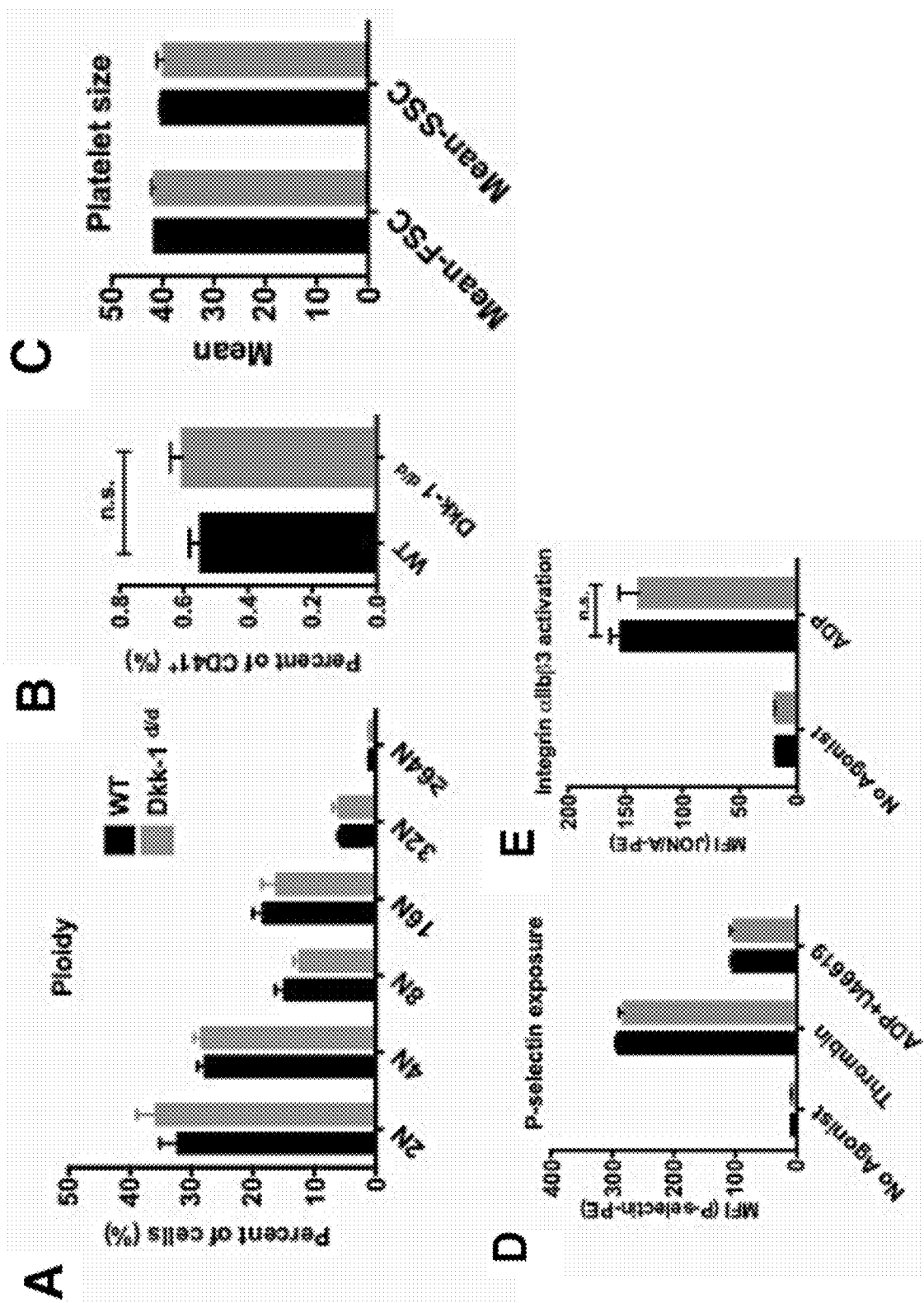
FIG. 2A through FIG. 2G, depicts results of experiments showing Dkk-$1^{d/d}$ mice have normal megakaryocyte ploidy, platelet size and platelet activation.
Figures 2F, 2G:
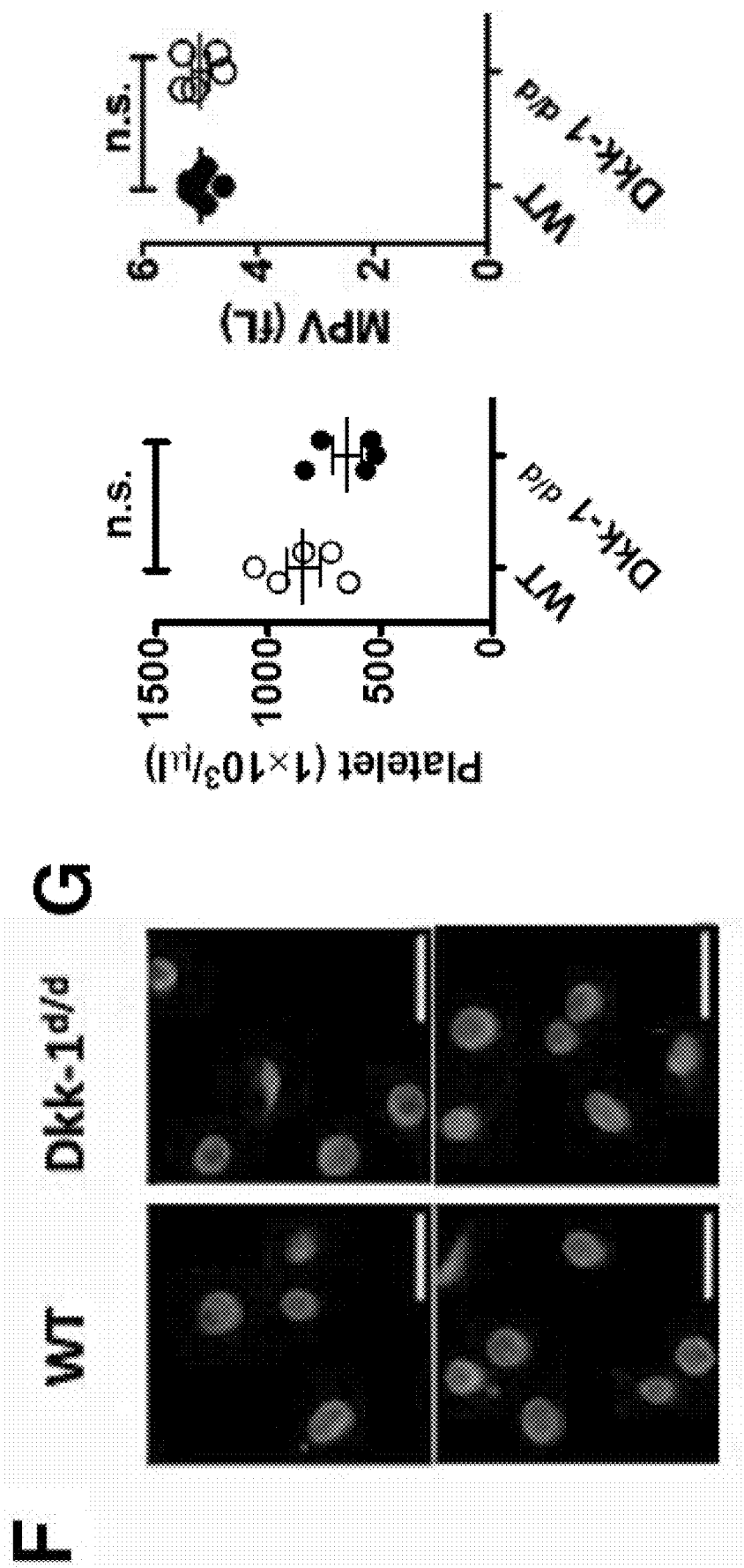
Figures 3A, 3B, 3C:
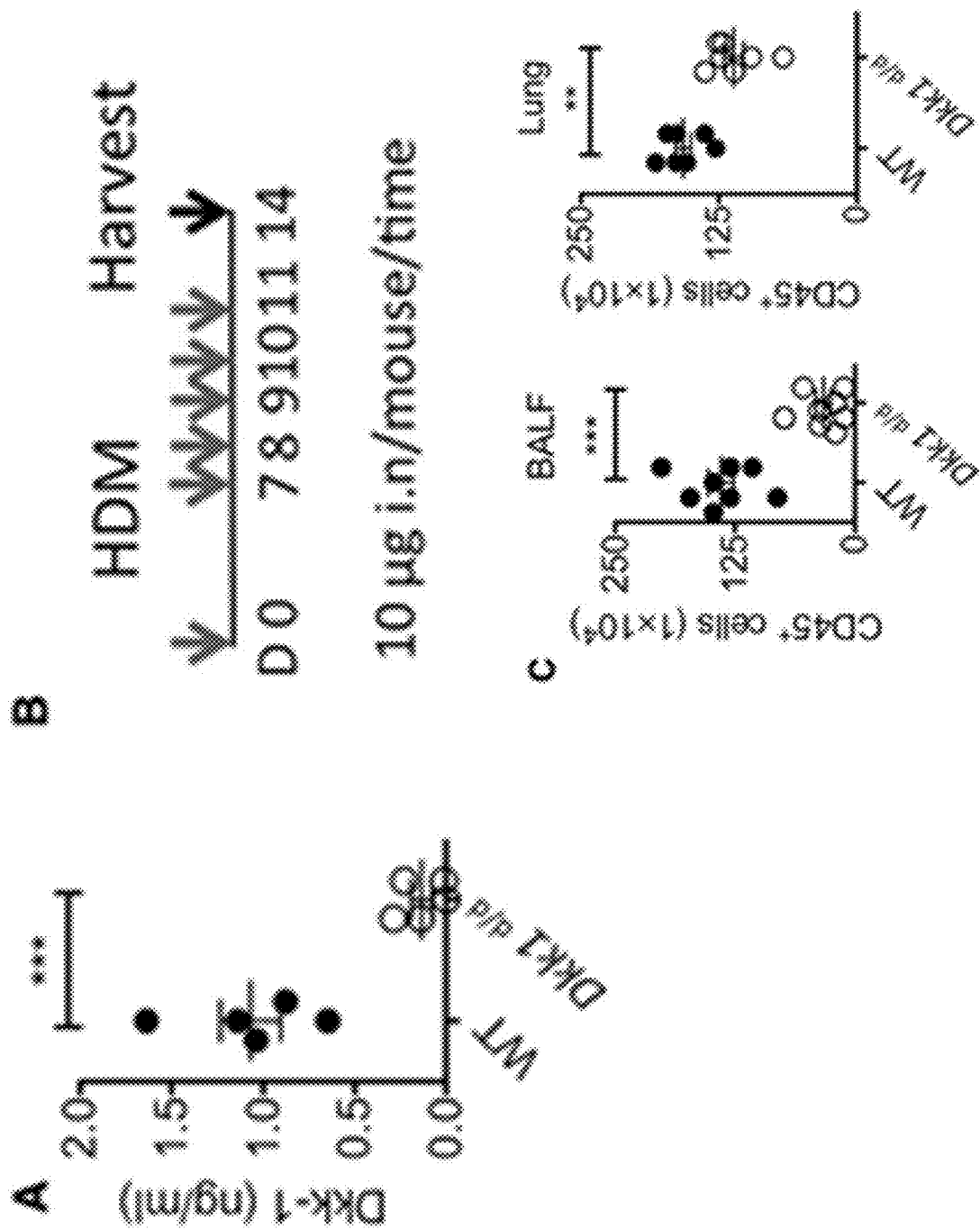
Figures 3F, 3G, 3H:
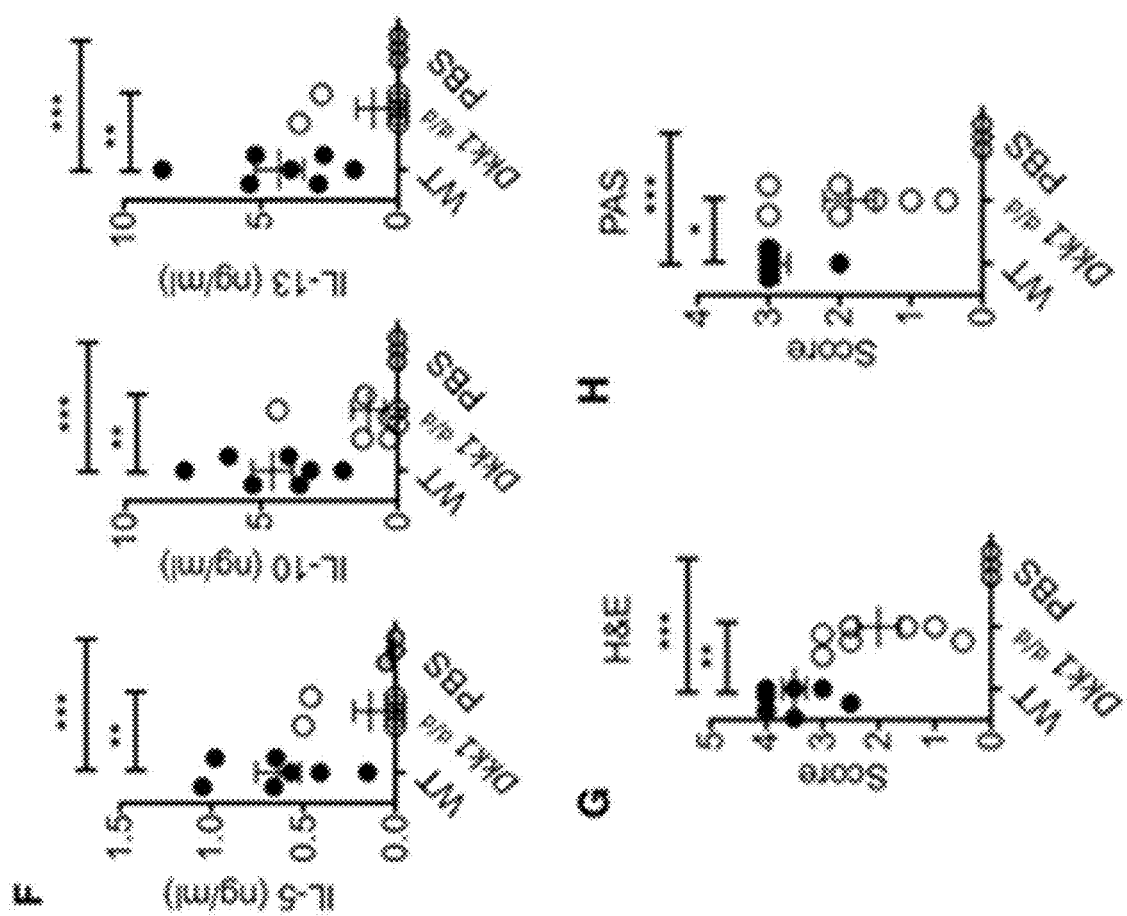
Figure 3I:
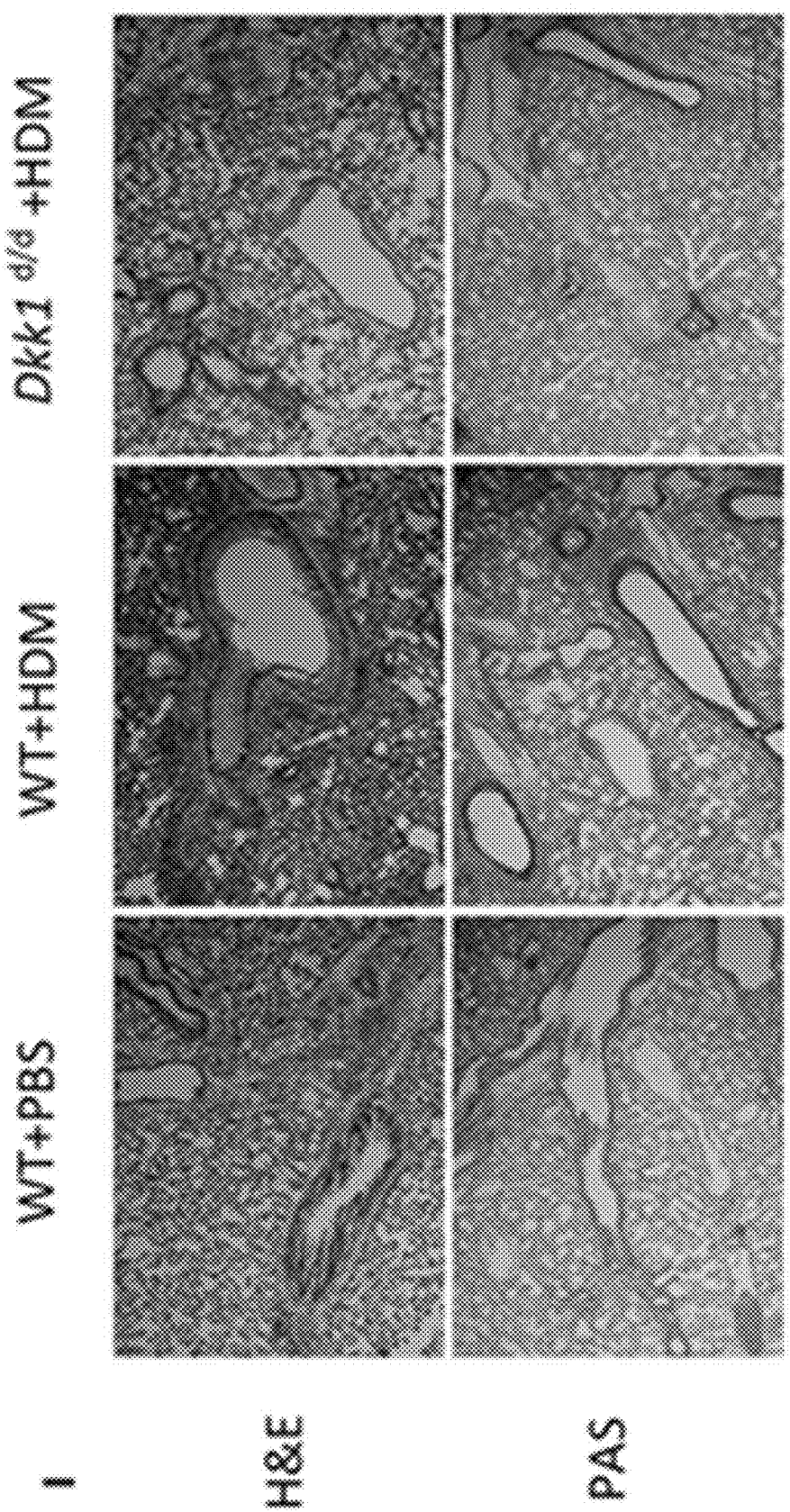

Dkk-1 Hypomorphic Mice are Protected from House Dust Mite-Induced Asthma $T_H2$-cell-mediated immune responses typically involve tissue damage and repair that requires the regulation of Wnt signaling (Pulendran and Artis, 2012, Science 337:431-5; Whyte et al., 2012, Cold Spring Harb Perspect Biol 4:a008078). To explore the possibility that Dkk-1 functions as an immunomodulatory ligand in a standard model of house dust mite (HDM) extract allergen challenge, the Dkk-1 hypomorphic doubleridge (Dkk-1$^{d/d}$) mouse strain was used in which Dkk-1 expression is reduced by 90%. First, the hematological features of doubleridge mice were characterized. Of note, CD4 T cells from doubleridge mice showed comparable cytokine production upon activation to those from WT littermate controls and the splenic CD4 T cell population did not show significant differences in their cell surface markers of activation (FIG. 1). Platelets from Dkk-1$^{d/d}$ mice and WT mice were characterized and it was determined that platelets from Dkk-1$^{d/d}$ mice were functionally comparable to WT platelets (FIG. 2). The reduced level of Dkk-1 in plasma from doubleridge mice was confirmed (FIG. 3A) and the doubleridge mice with HDM extract (FIG. 3B). CD45⁺ leukocytes including neutrophils, eosinophils, and CD4 T cells were significantly increased in the lung and broncho-alveolar lavage (BAL) fluid of WT mice but this was substantially decreased in Dkk-1$^{d/d}$ mice, suggesting that the reduced expression of Dkk-1 following allergen challenge inhibited the infiltration of leukocytes to the lung (FIGS. 3C, 3D, 3E). $T_H2$ cytokines (IL-5, IL-10 and IL-13) were markedly induced in WT mice but notably decreased in Dkk-1$^{d/d}$ mice in ex vivo stimulation of mediastinal lymph node (medLNs) cells with HDM allergen extract (FIG. 3F). Hematoxylin and eosin (H&E) and periodic acid-Schiff base (PAS) staining and scoring of lung tissues also showed that Dkk-1$^{d/d}$ mice had reduced inflammation and leukocyte infiltration compared to WT mice (FIGS. 3G, 3H and 3I). Moreover, airway resistance increase by HDM was notably decreased by using Dkk-1 inhibitor, (1-(4-(naphthalen-2-yl)pyrimidin-2-yl)piperidin-4-yl)methanamine) (Pelletier et al., 2009, J Med Chem 52:6962-5) (WAY-262611) or in Dkk-1$^{d/d}$ mice (FIG. 1F). Taken together, these results demonstrated that lack of Dkk-1 protects the host from chronic type 2 immune responses in the HDM-induced asthma model.

Figures 4A, 4B, 4C, 4D:
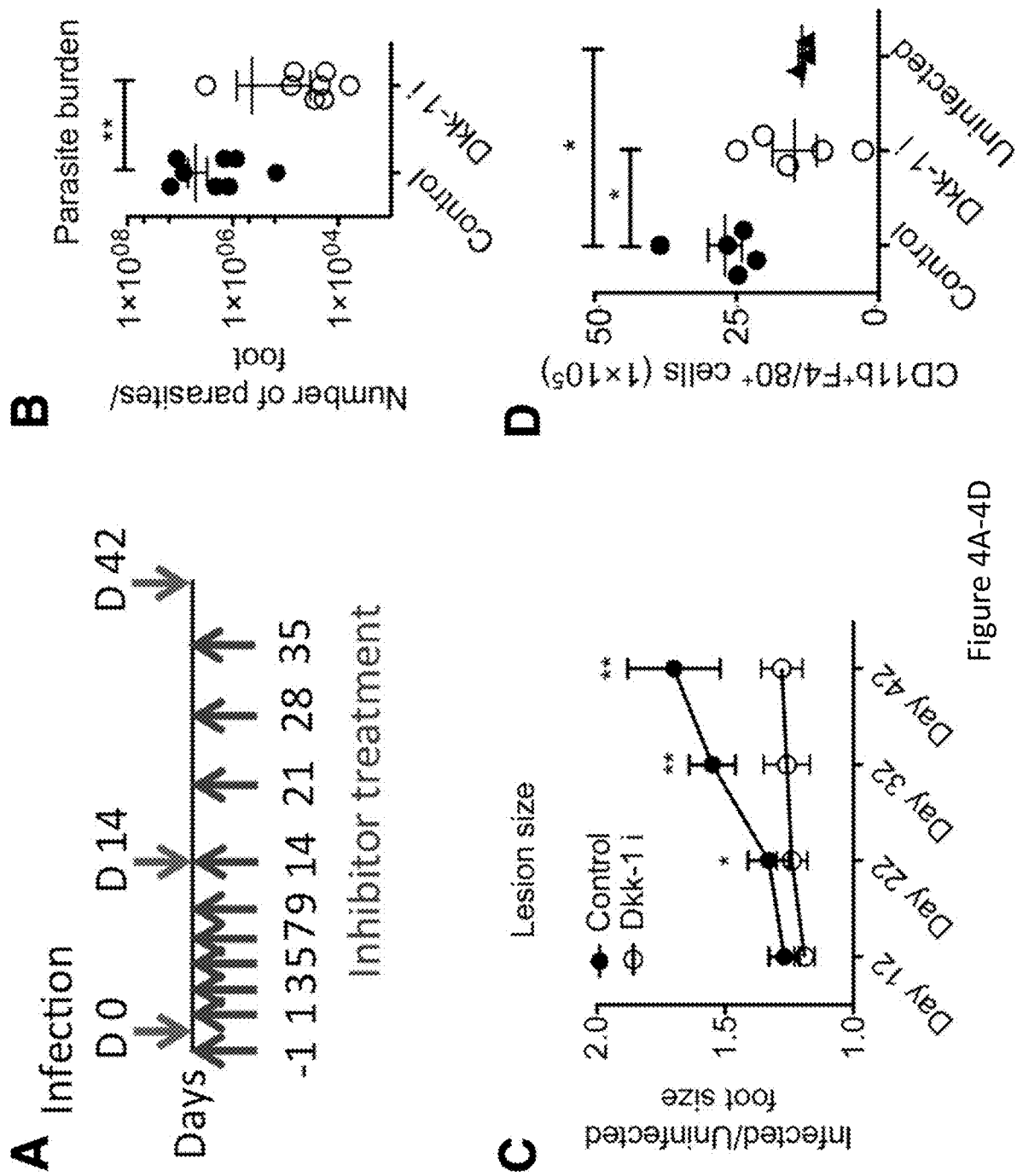
FIG. 4A through FIG. 4H, depicts results of experiments showing functional inhibition of Dkk-1 protects the host from chronic inflammation caused by *L. major*.
Figures 4E, 4F, 4G, 4H:
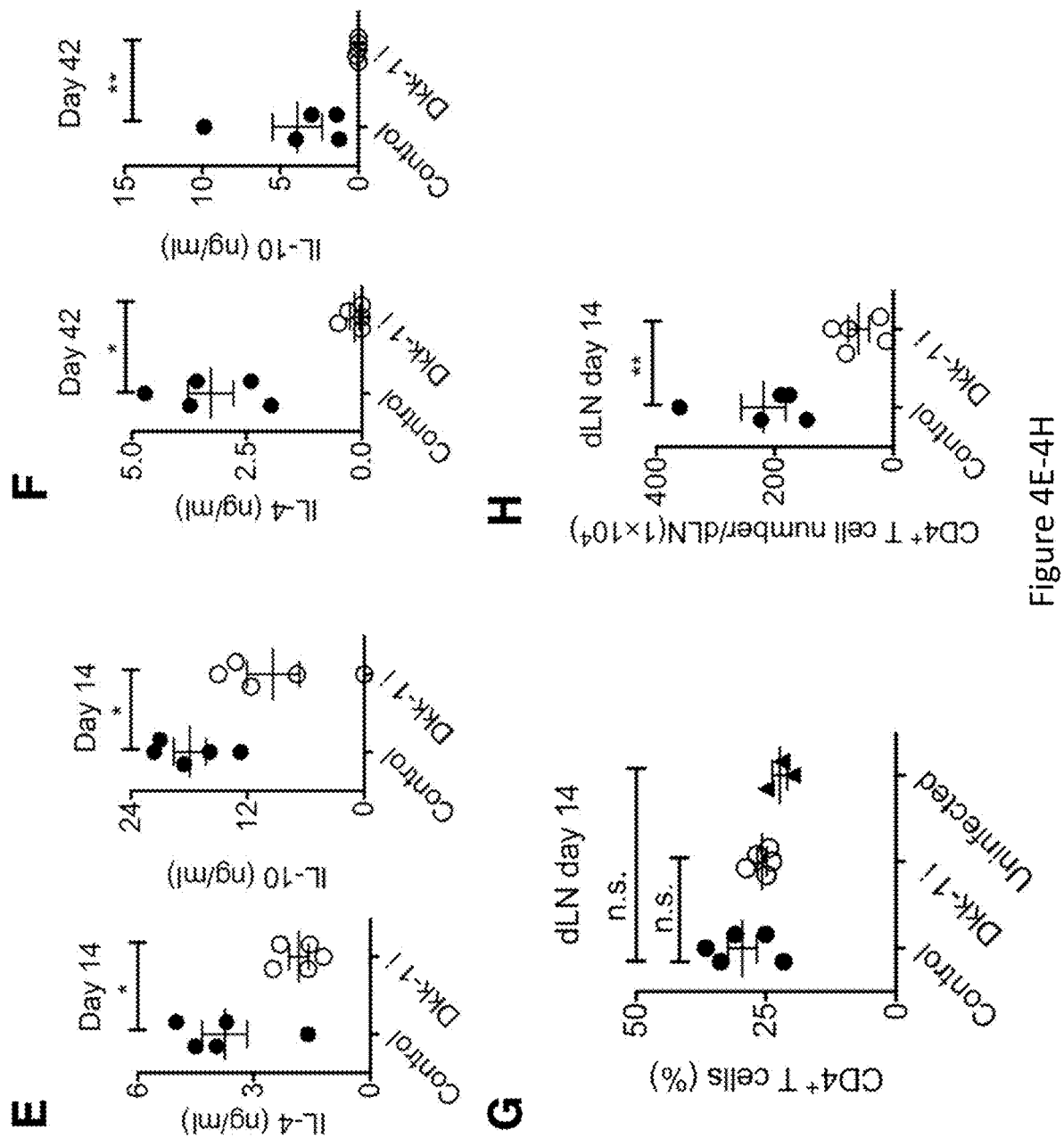

Functional Inhibition of Dkk-1 Protects Mice from *Leishmania (L.) major* Infection It was further questioned whether functional inhibition of Dkk-1 could impair chronic inflammation by different types of environmental pathogens via a different route of challenge such as skin. Parasite infections challenge the immune system to temper its activity with highly evolved immune evasion strategies (Redpath et al., 2014, Parasite Immunol 36:233-52). Infection with the parasite *Leishmania (L.) major* causes chronic skin lesion formation with unresolved inflammation by T$_H$2 immune responses in a murine model (Belkaid et al., 2001, J Exp Med 194:1497-506; Tacchini-Cottier et al., 2012, Front Immunol 3:32). Many inbred mouse strains such as C57BL/6, C3H, and CBA/J are genetically resistant to *L. major* and spontaneously resolve infection because they mount a protective T$_H$1-type response. In contrast, susceptible BALB/c mice develop large nonhealing chronic lesions and mount a T$_H$2 response that is associated with the production of the cytokines IL-4 and IL-10 (Reiner and Locksley, 1995, Annu Rev Immunol 13:151-77; Scott, 1991, J Immunol 147:3149-55). It was assessed whether the inhibition of Dkk-1 function impairs T$_H$2 cell polarization, ameliorating the development of cutaneous leishmaniasis. A Dkk-1 inhibitor, WAY-262611 was administered intraperitoneally during the course of *L. major* infection (FIG. 4A). Both lesion size and parasite burden were greatly reduced at 42 days post-infection, showing an 11.5-fold reduction of parasite survival in the Dkk-1 inhibitor-treated group (FIGS. 4B and 4C). Macrophage accumulation following parasite infection was also diminished by 14 days after infection (FIG. 4D). IL-4 and IL-10 production was notably reduced by Dkk-1 inhibitor treatment at days 14 and 42 post-infection following ex vivo stimulation of draining lymph node cells from the infected mice with soluble leishmania antigen (sLMAG), suggesting that type 2 cytokine production was promoted by Dkk-1 (FIGS. 4E and 4F). It has been known that *L.major* infection induces CD4 T cell recruitment and proliferation with lymph node expansion as well as T$_H$2 cell differentiation (Carvalho et al., 2012, J Immunol 188:1394-401; Hsu and Scott, 2007, J Immunol 179:8200-7). Dkk-1 inhibitor treatment did not reduce the percentage of CD4 T cells in draining lymph nodes (dLN) but reduced the number of CD4 T cells in the dLN (FIGS. 4G and 4H), indicating that CD4 T cell proliferation/recruitment is markedly reduced by Dkk-1 inhibition and this is concomitantly associated with reduced IL-4 and IL-10 production in draining lymph nodes. Taken together, these results suggest that different types and routes of environmental challenges induced elevation of circulating Dkk-1 to promote chronic tissue inflammation with robust type 2 cytokine production.

Dkk-1 Polarizes CD4 T Cells to T$_H$2 Cell Lineage

Figures 5A, 5B:
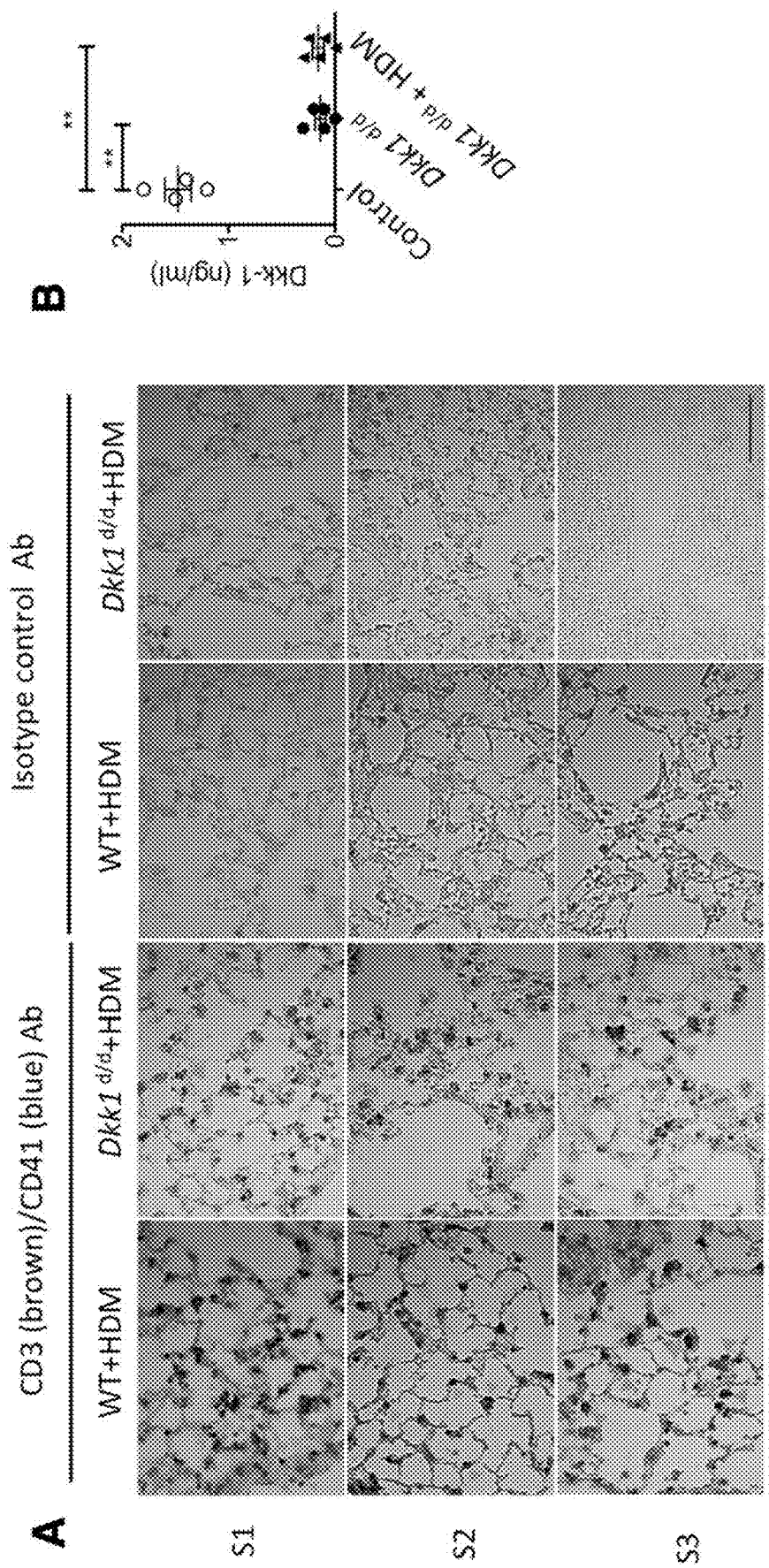
FIG. 5A through FIG. 5E, depicts results of experiments showing Dkk-1 induces $T_H2$ cell polarization.
Figure 5C:
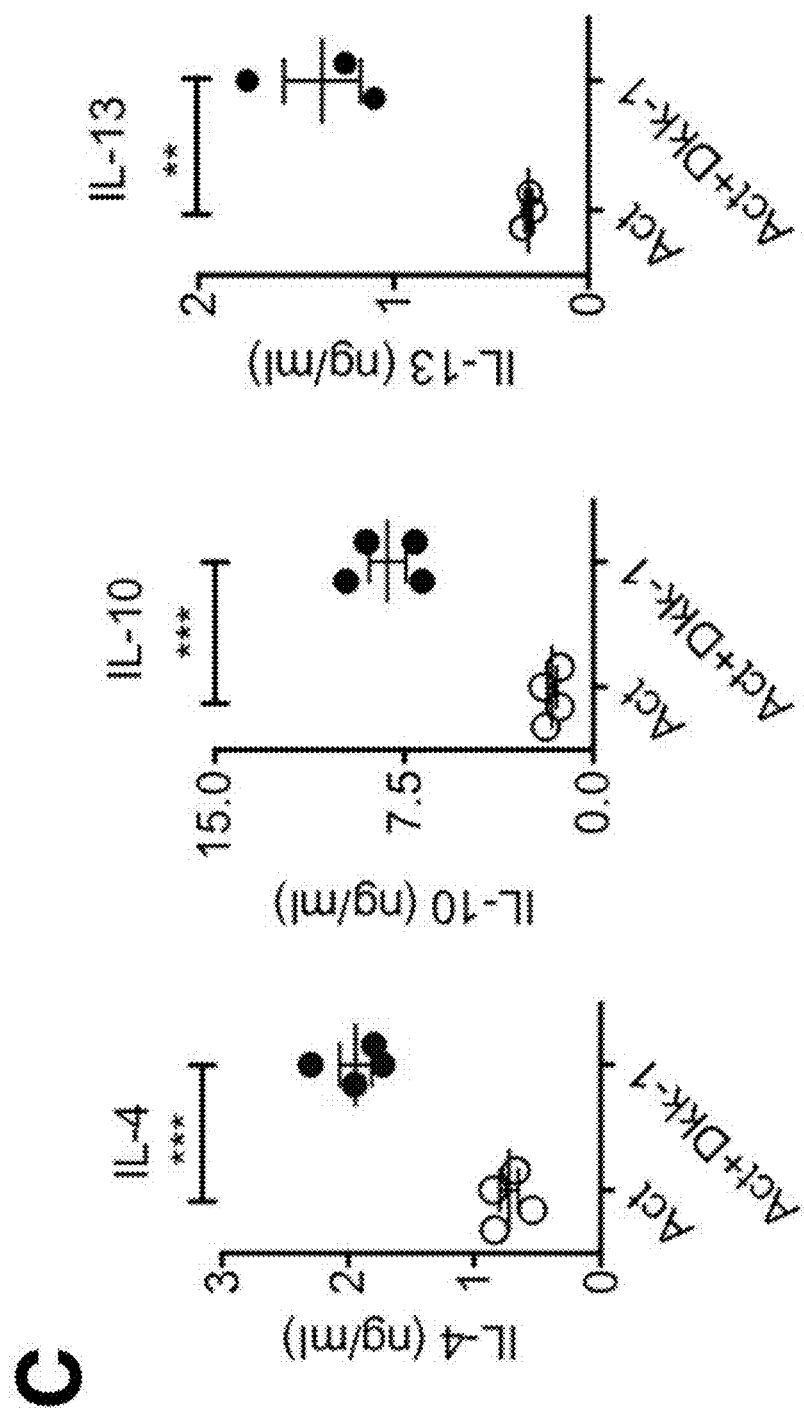
Figure 5D:
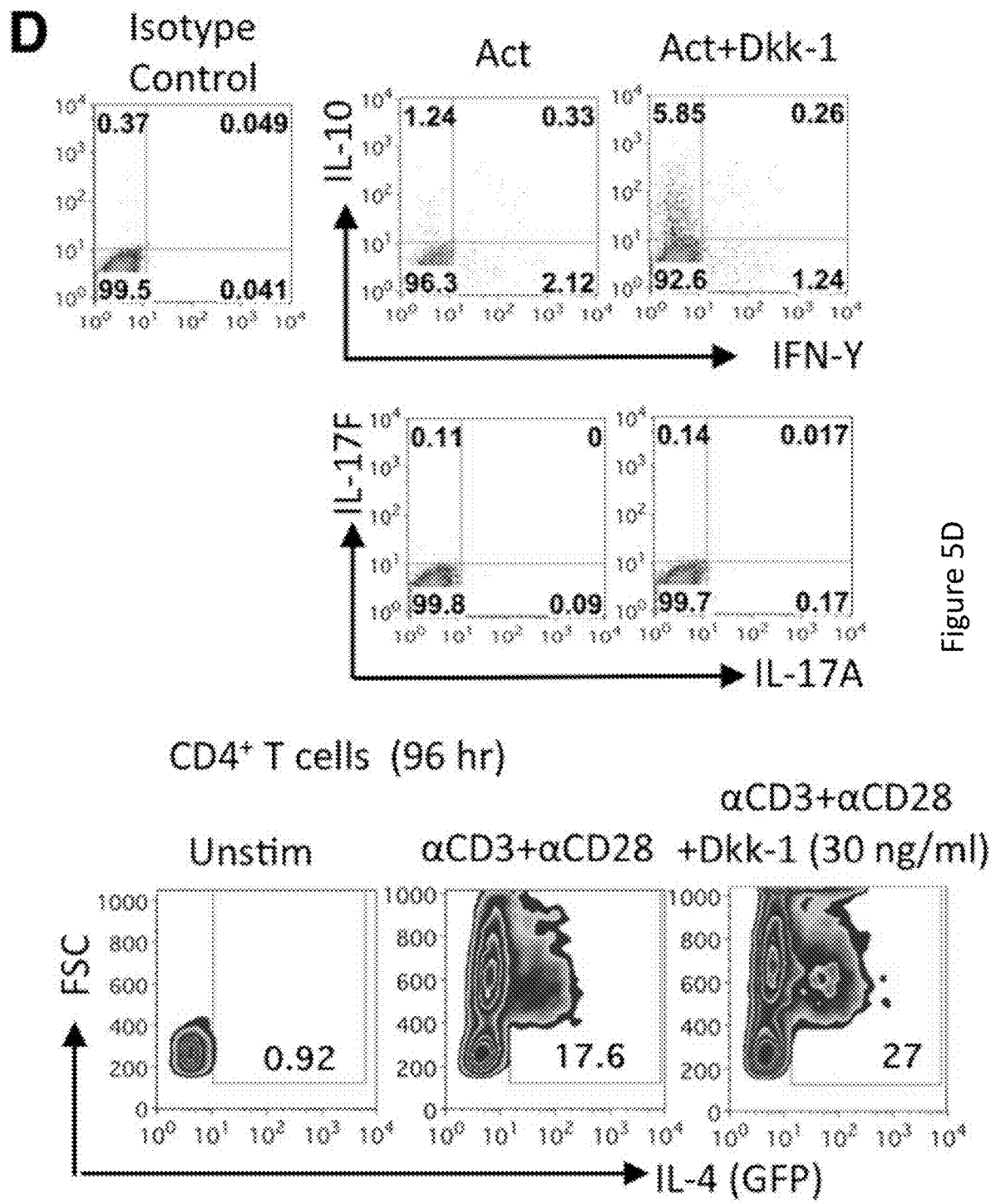
Figure 5E:
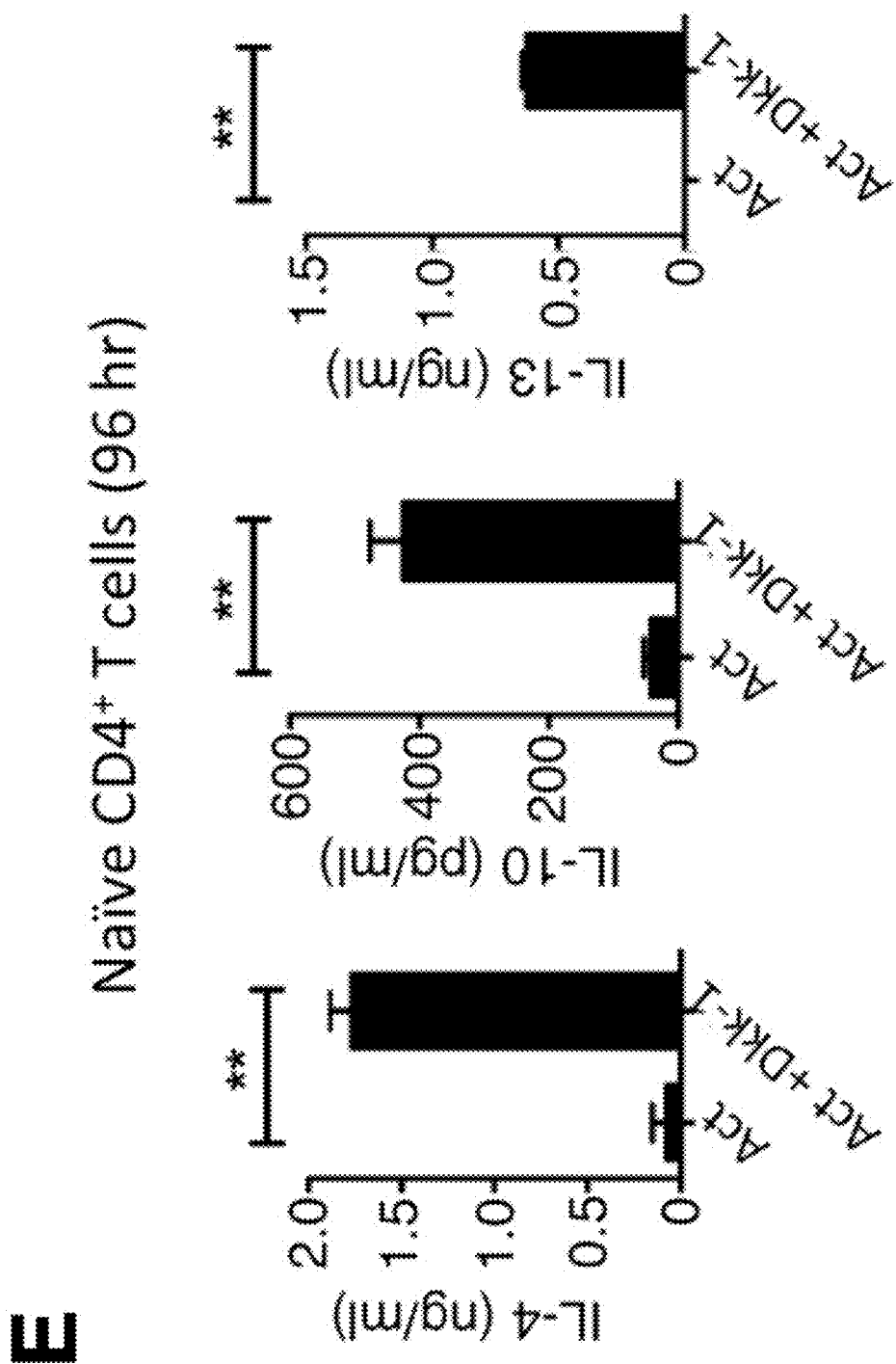

From the allergen exposure model, it was observed that platelets and T cells were co-localized in the lung in WT mice after recurrent allergen challenges but this was reduced in Dkk-1$^{d/d}$ mice (FIG. 5A). This increased T cell infiltration in the lung in WT mice compared to Dkk-1$^{d/d}$ mice was consistent with the increased CD4 T cell numbers and the H&E score in the lung (FIGS. 3E and 3G). It was assessed whether any residual Dkk-1 might be induced in Dkk-1$^{d/d}$ mice, but no elevation of Dkk-1 after HDM challenge in Dkk-1$^{d/d}$ mice was detected (FIG. 5B). Next, it was determined if Dkk-1 induces T$_H$2 cytokines from CD4 T cells; Dkk-1 induced IL-4, IL-10 and IL-13 in total CD4 T cell activation in vitro (FIG. 5C). Other important effector T cell cytokines including T$_H$1 and T$_H$17-associated cytokines (e.g. IFN-γ, IL-17A and IL-17F) were not induced by Dkk-1, suggesting that Dkk-1 preferentially induces T$_H$2 cytokines (FIG. 5D). This induction of T$_H$2 cytokines was also observed when naïve CD4 T cells were activated with Dkk-1 in vitro (FIG. 5E).

Figure 6A:
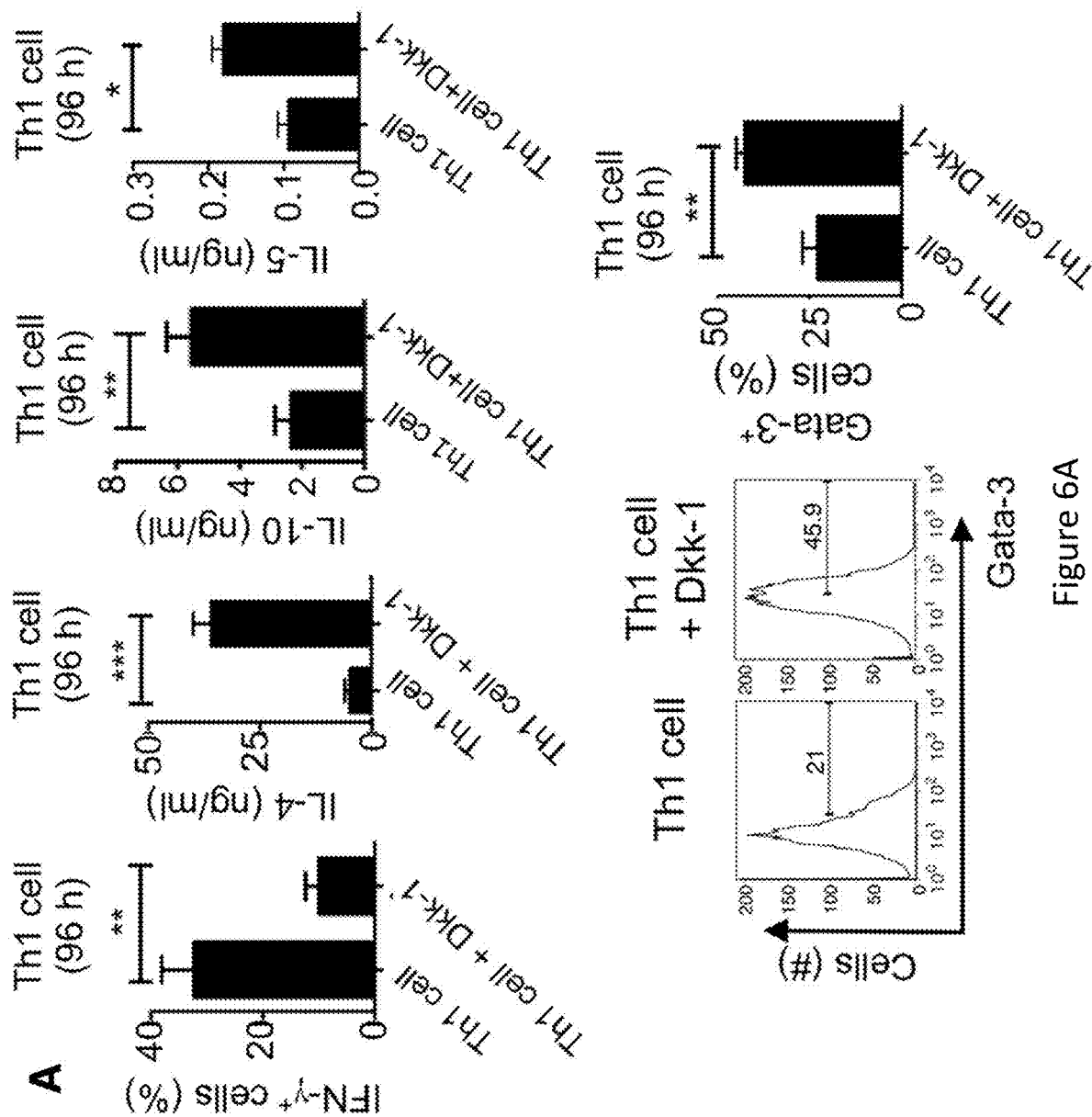
FIG. 6A through FIG. 6E, depicts results of experiments showing Dkk-1 induces $T_H2$ cytokines in various T cell differentiation conditions.
Figure 6B:
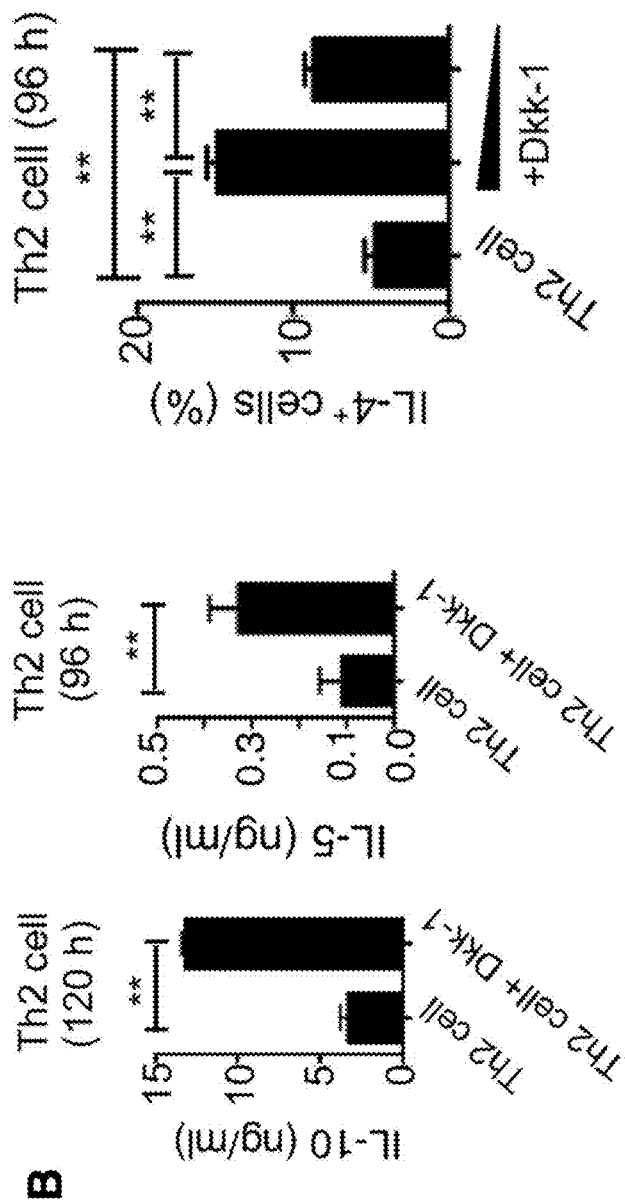
Figure 6B:
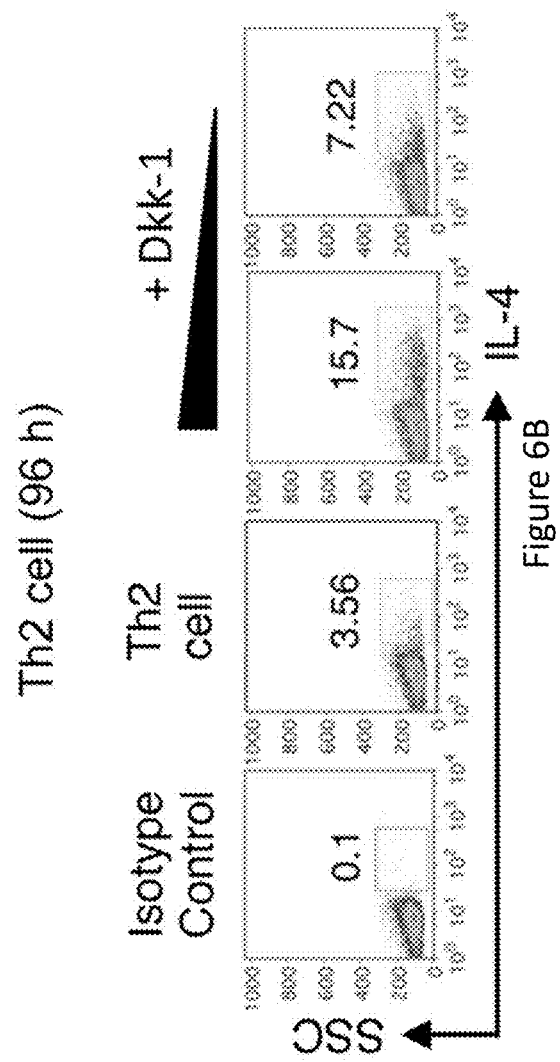
Figure 6C:
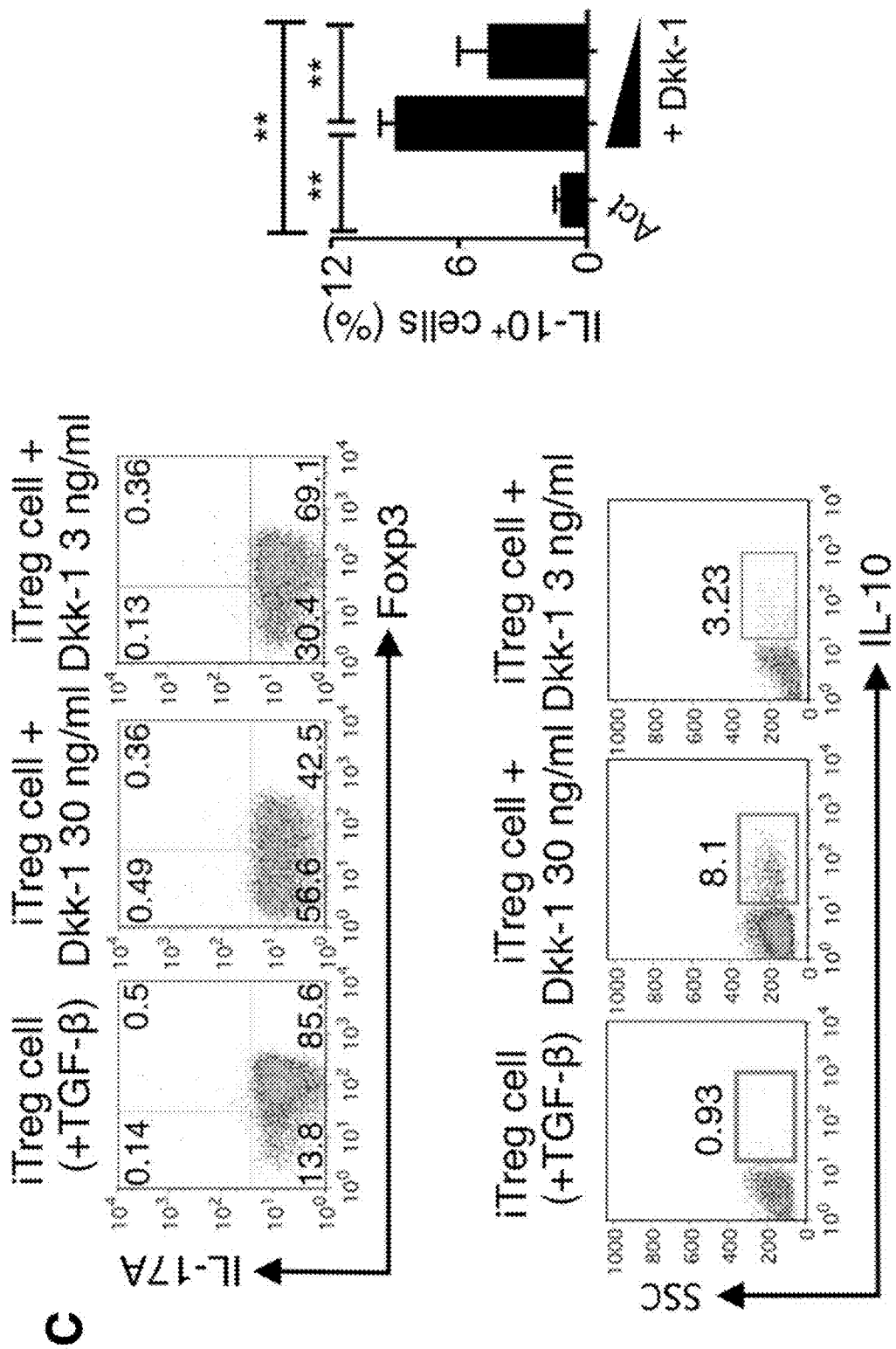
Figure 6D:
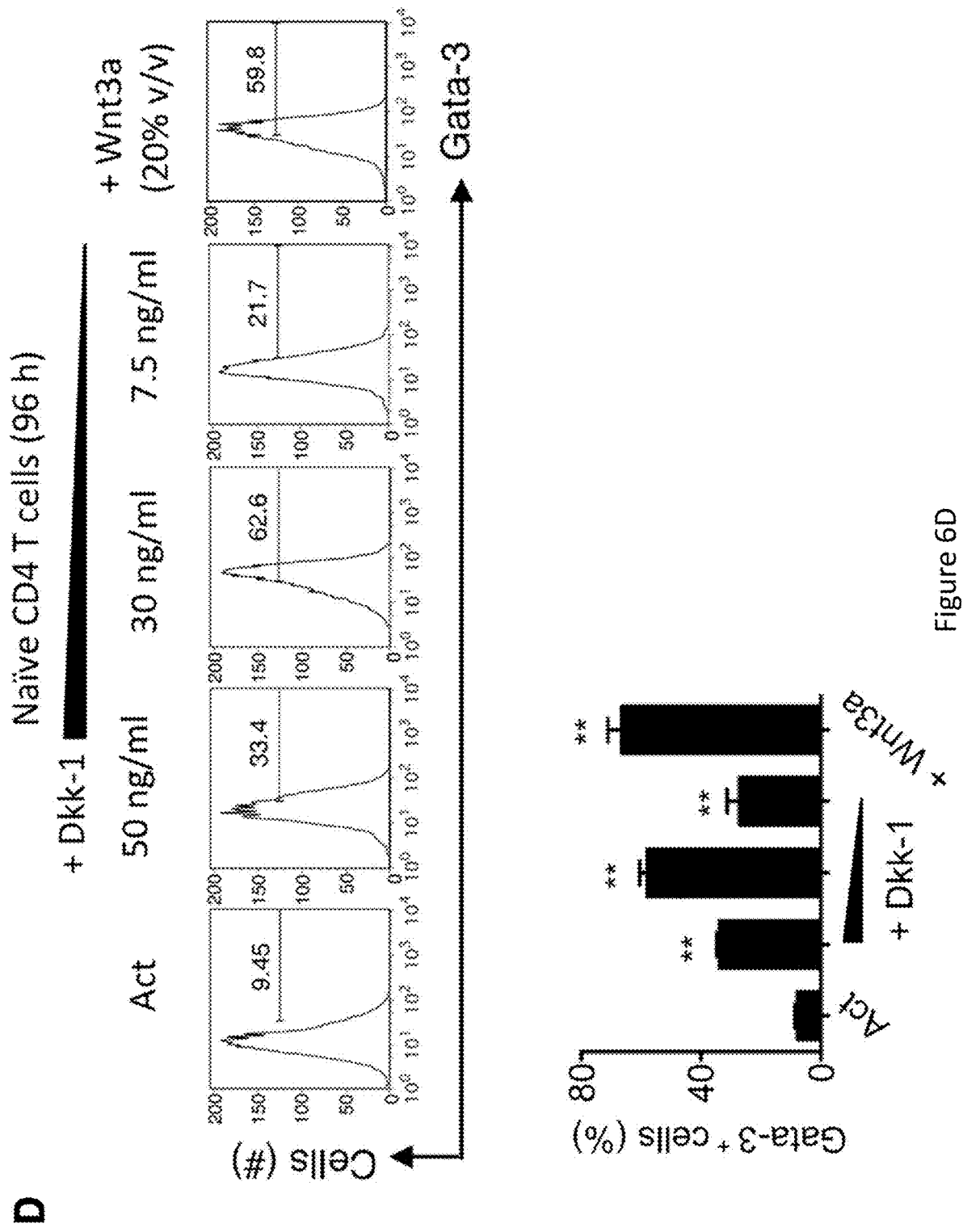
Figure 6E:
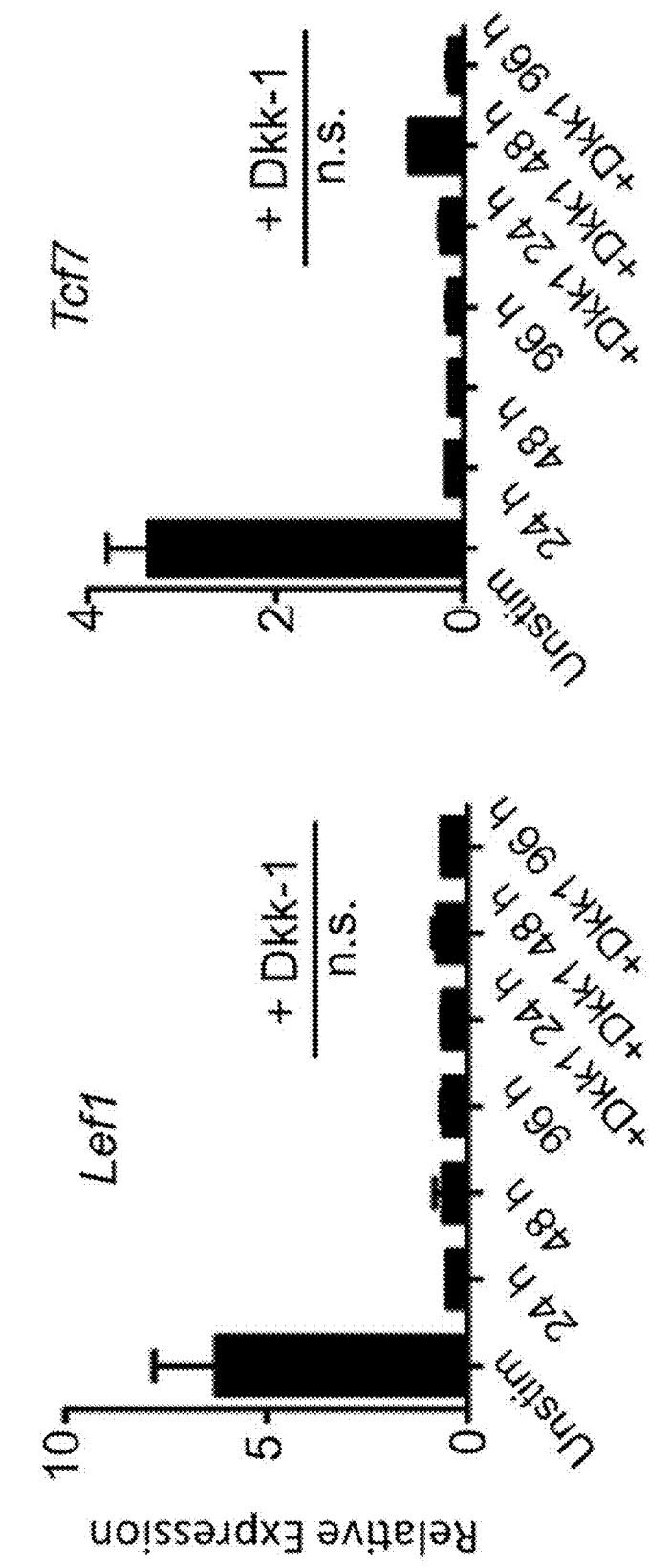

It was further examined whether Dkk-1 could antagonize T$_H$1 cell polarization. Dkk-1 suppressed IFN-γ expression under T$_H$1 polarization conditions while still elevating Gata-3 expression and IL-4, IL-5, IL-10, IL-13 secretion, suggesting its strong ability to drive T$_H$2 cell polarization (FIG. 6A). Finally, Dkk-1 enhanced IL-4 expression in a dose-dependent manner and also potentiated IL-4, IL-5 and IL-10 production from cells undergoing T$_H$2 cell differentiation (FIG. 46B). It was also observed that Dkk-1 could induce IL-10 in the presence of TGF-β while inhibiting TGF-β-mediated Foxp3 expression (FIG. 6C). Of note, the dose dependent response of Dkk-1 on Gata-3 expression was tested and compared with Wnt3a. Interestingly, up to 30 ng/ml of Dkk-1 could induce Gata-3 expression similar to Wnt3a; however at higher amounts, Dkk-1 inhibited Gata-3 expression (FIG. 6D). It has been shown that the canonical Wnt pathway transcription factors such as Lef and TCF-1 (also known as Tcf7) act as repressors of Gata-3 transcription in naïve CD4 T cells, and IL-4 inhibits TCF-1 expression (Hebenstreit et al., 2008, J Biol Chem 283:22490-22497; Maier et al., 2011, J Biol Chem 286:919-28). As previously reported, naïve CD4 T cell activation downregulated Lef and T cell factor-1 (TCF-1) expression. Dkk-1 did not induce TCF-1 or Lef expression (FIG. 6E). Collectively, these results showed that Dkk-1 induced T$_H$2 cell polarization and potentiated T$_H$2 type cytokine expression.

Dkk-1 Utilizes SGK-1 and p38 MAPK to Potentiate T$_H$2 Cytokine Production

The T$_H$2 differentiation program is mediated by Gata-3 and c-Maf (Farrar et al., 2001, J Exp Med 193:643-50; Ho et al., 1996, Cell 85:973-83; Lee et al., 2001, Immunity 14:447-59). Since FIG. 6D showed that Dkk-1 could induce Gata-3 expression from naïve CD4 T cells in a dose-dependent manner and hence T$_H$2 cytokines, it was further investigated how Dkk-1 potentiated T$_H$2 cytokine production. Recent studies showed that helper T cell differentiation signaling is mediated by mTOR (mammalian/mechanistic target of rapamycin) and MAPK signaling pathways in response to diverse extracellular cues including Wnts (Chi, 2012, Nat Rev Immunol 12:325-38; Heikamp et al., 2014, Nat Immunol 15:457-64). In vivo, a CD4 T cell population in medLN that concomitantly expressed T$_H$2 cell polarization transcription factors Gata-3 and c-Maf was significantly increased after ex vivo stimulation in WT mice after 2 weeks of recurrent allergen challenges. However, this population was only minimally present in Dkk-1$^{d/d}$ mice (FIG. 7A), suggesting the role of Dkk-1 in inducing c-Maf. The decrease of T$_H$2 cytokines and the Gata-3$^+$c-Maf$^+$ CD4 T cell population in Dkk-1$^{d/d}$ mice was not related to a decreased percentage of CD4 T cells in the medLNs (FIG. 7A, right panel).

Figures 7A, 7B:
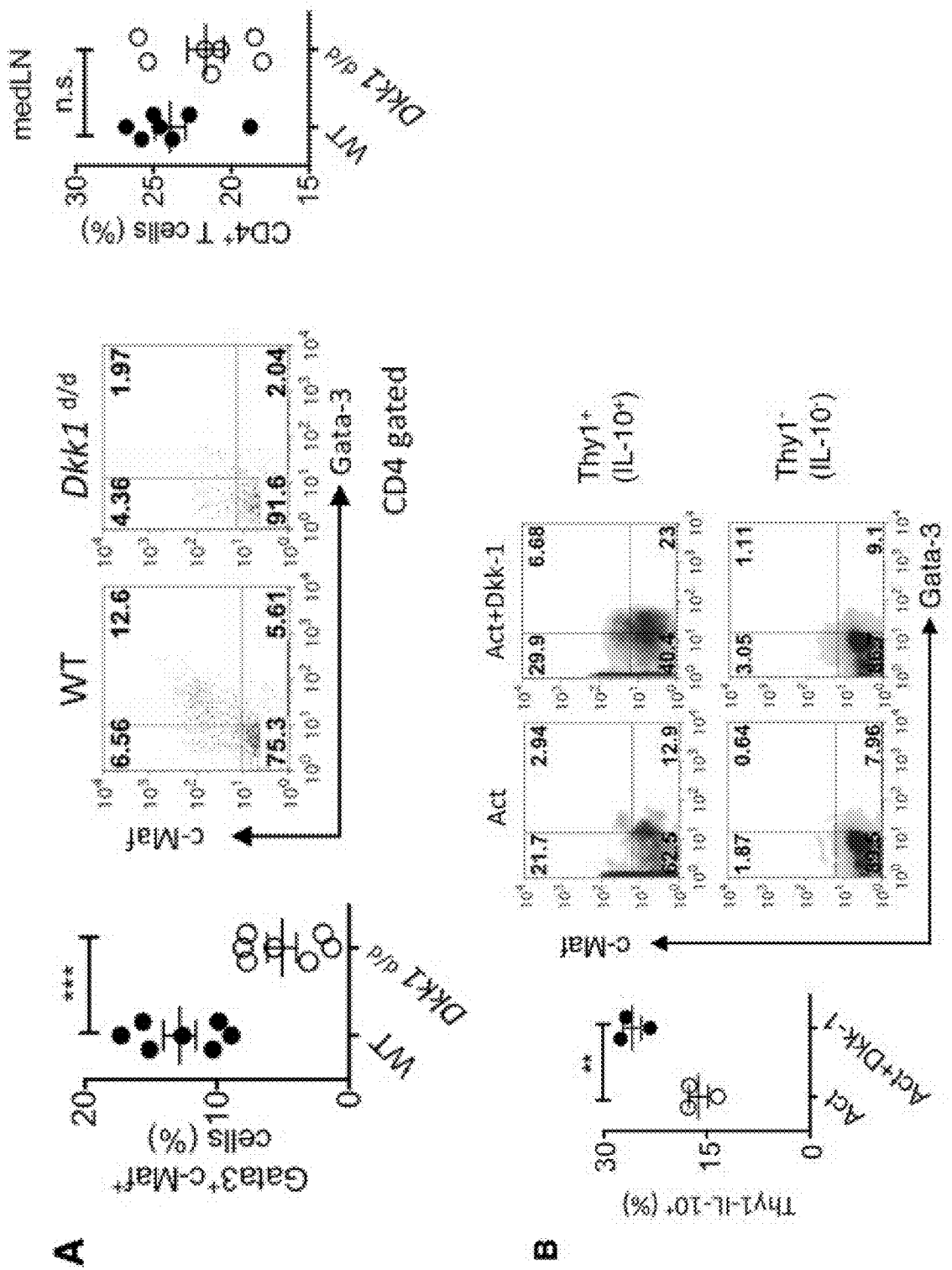
FIG. 7A through FIG. 7E, depicts results of experiments showing Dkk-1 directs $T_H2$ cell polarization by p38 MAPK and SGK-1 to induce c-Maf and Gata-3.
Figure 7C:
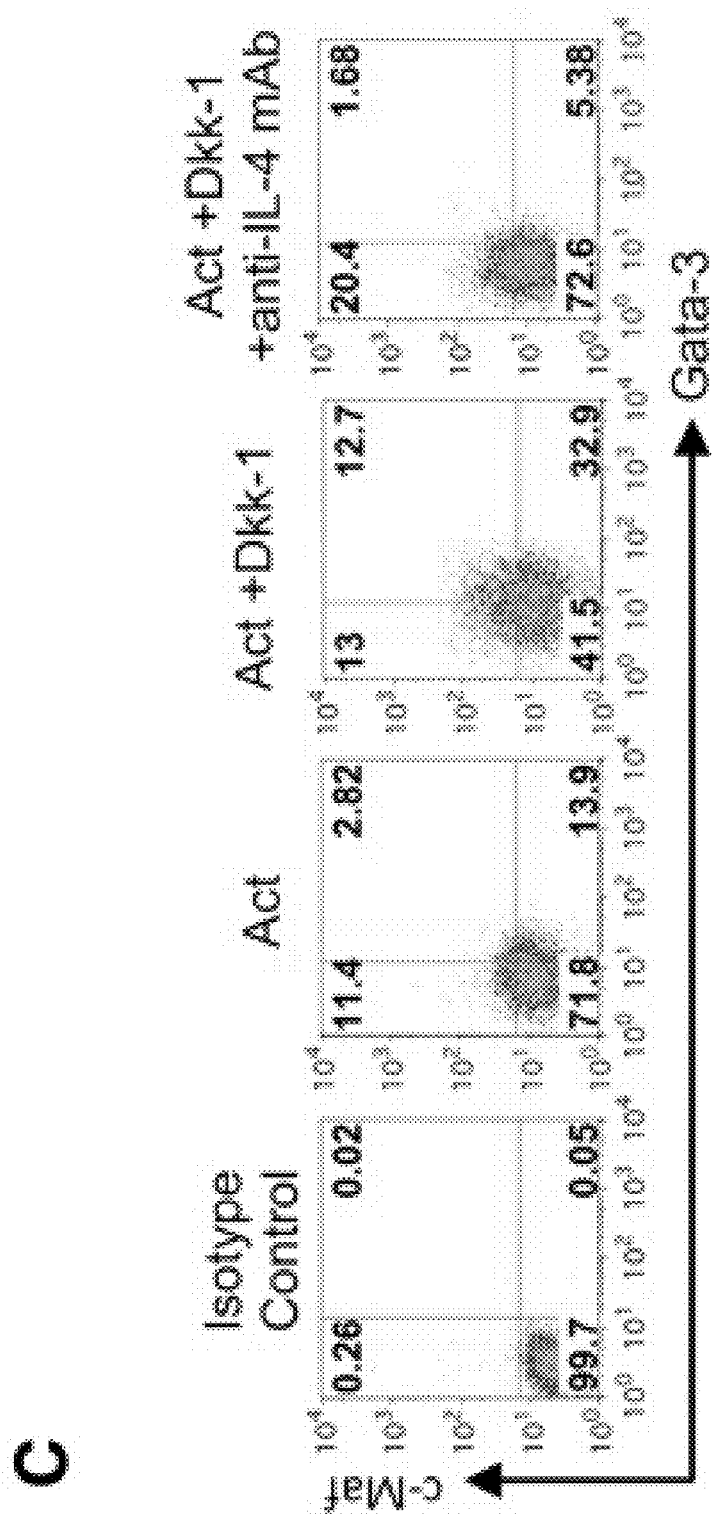
Figure 7D:
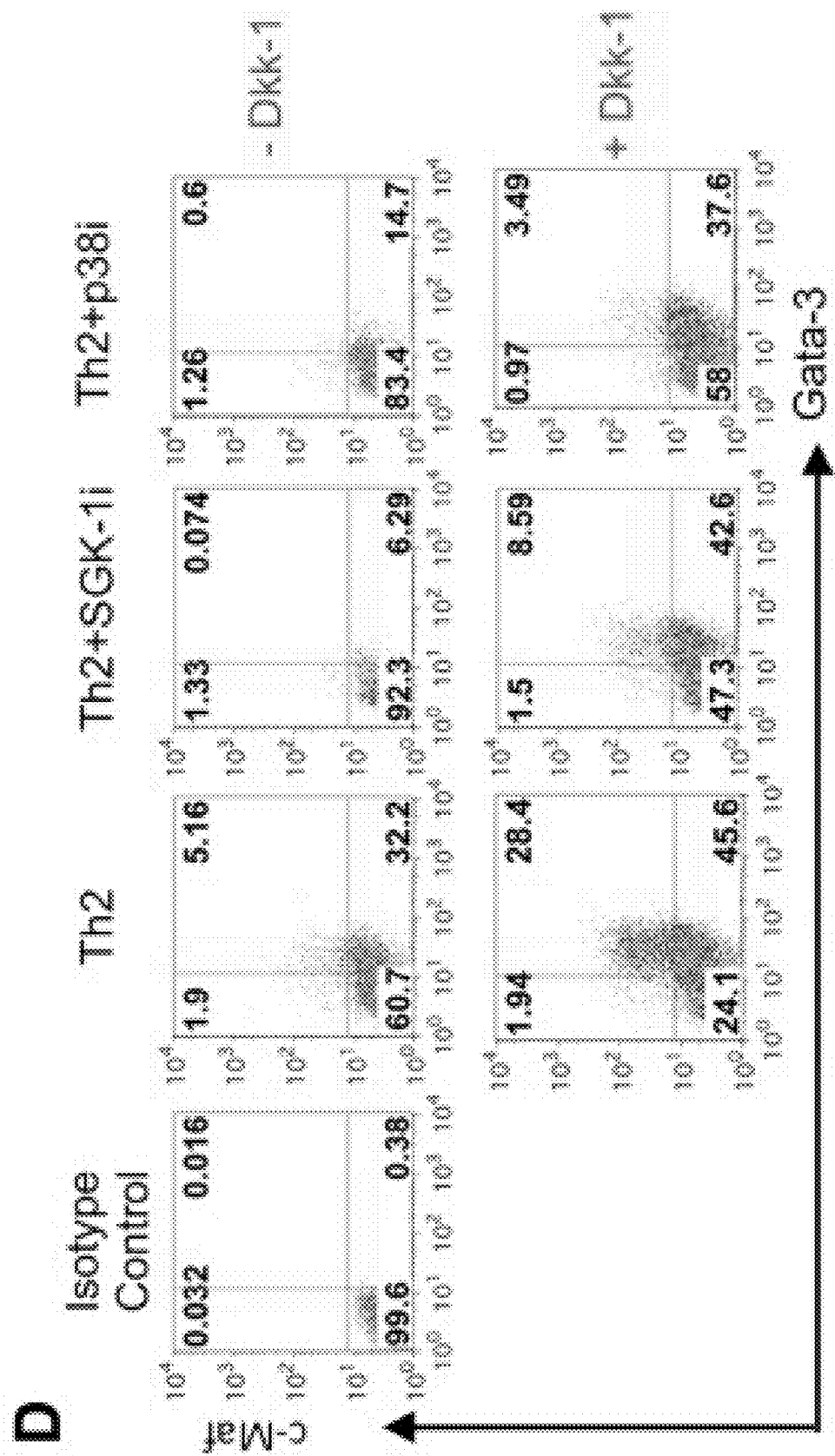
Figure 7E:
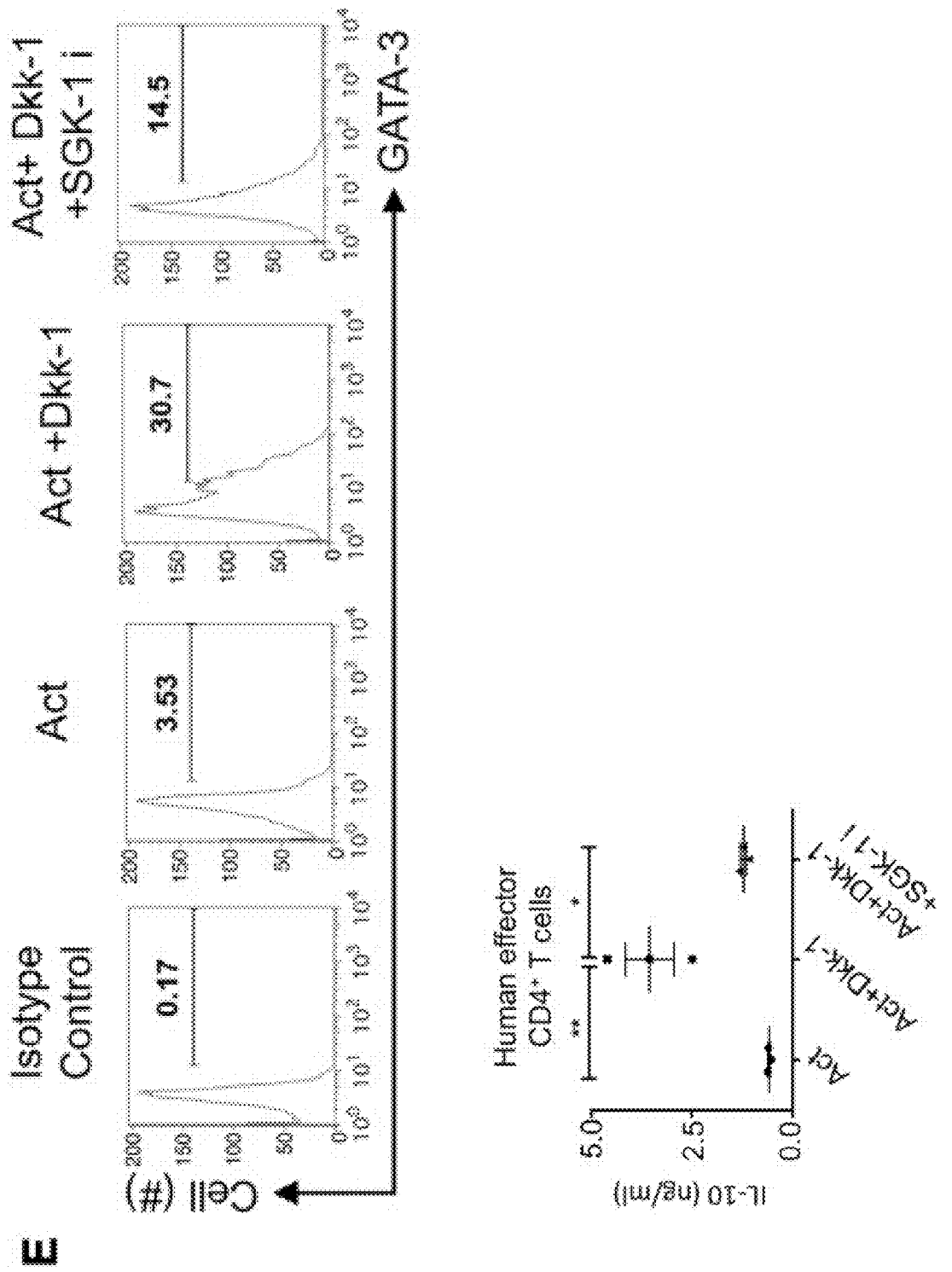
Figure 8A:
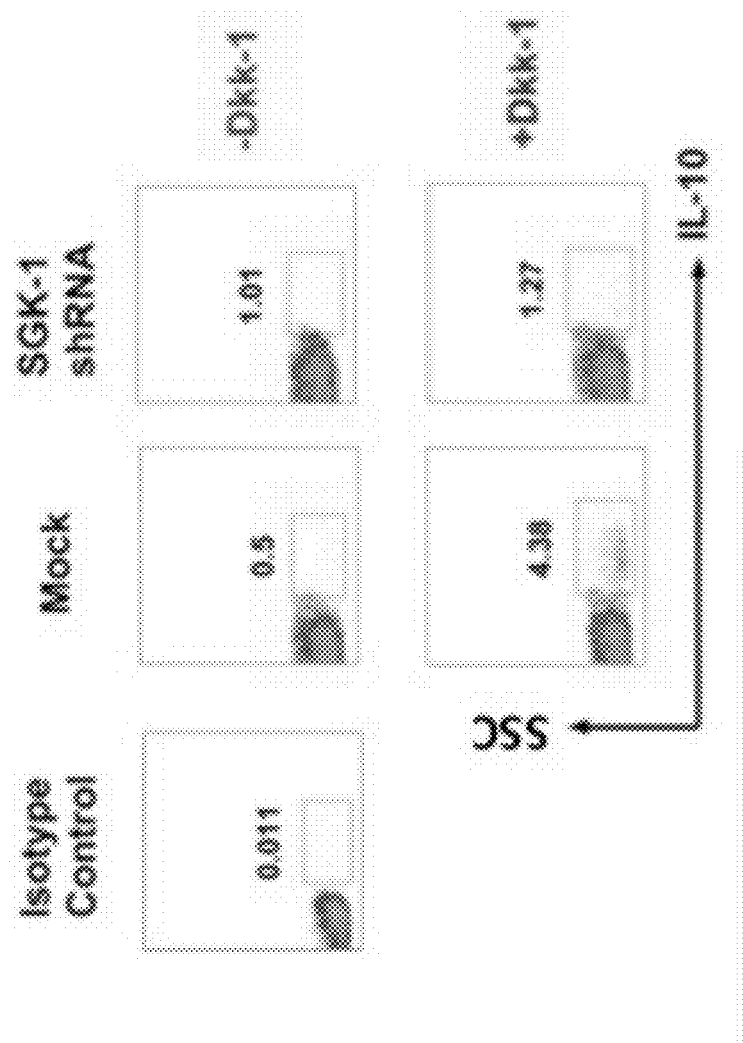
FIG. 8A through FIG. 8G, depicts results of experiments showing Dkk-1 induces IL-10 in CD4 T cells via SGK-1 and p38 MAPK.
Figure 8B:
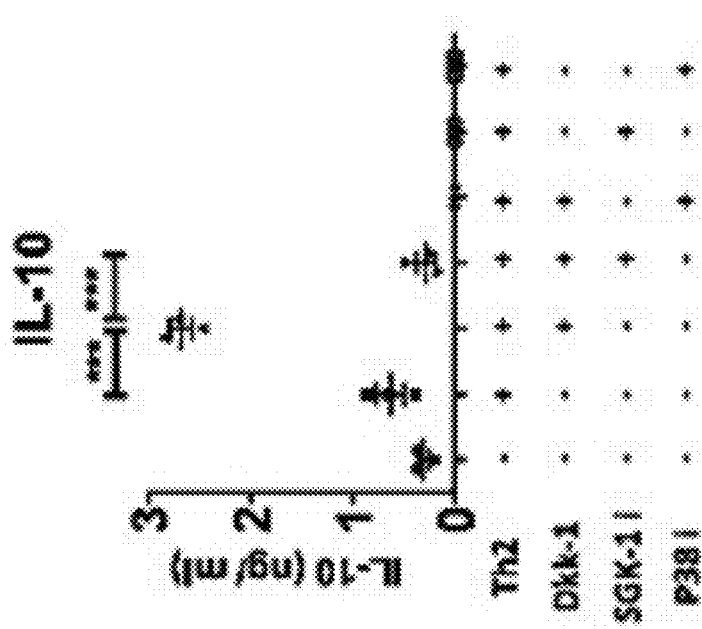
Figure 8C:
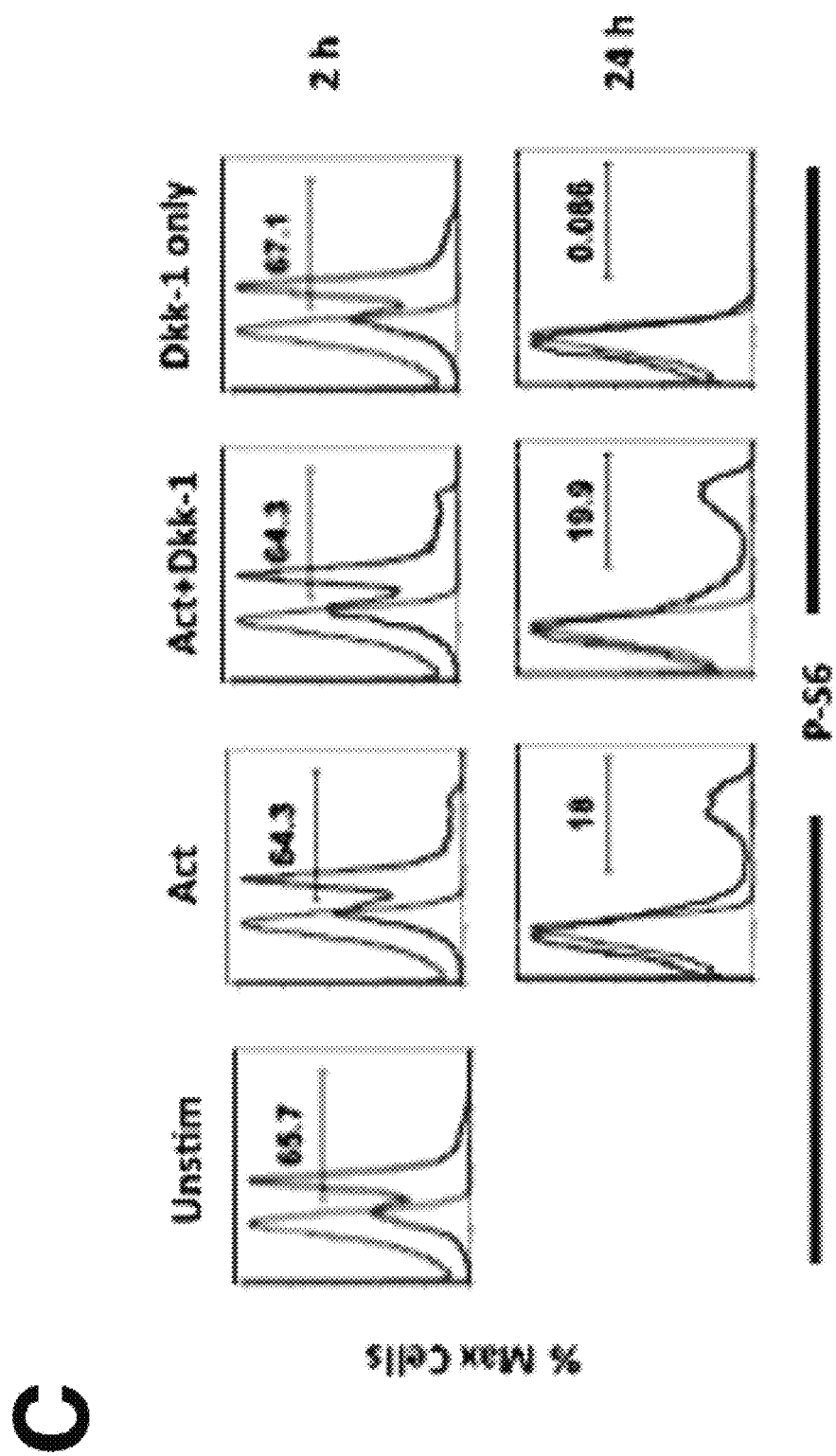
Figure 8D:
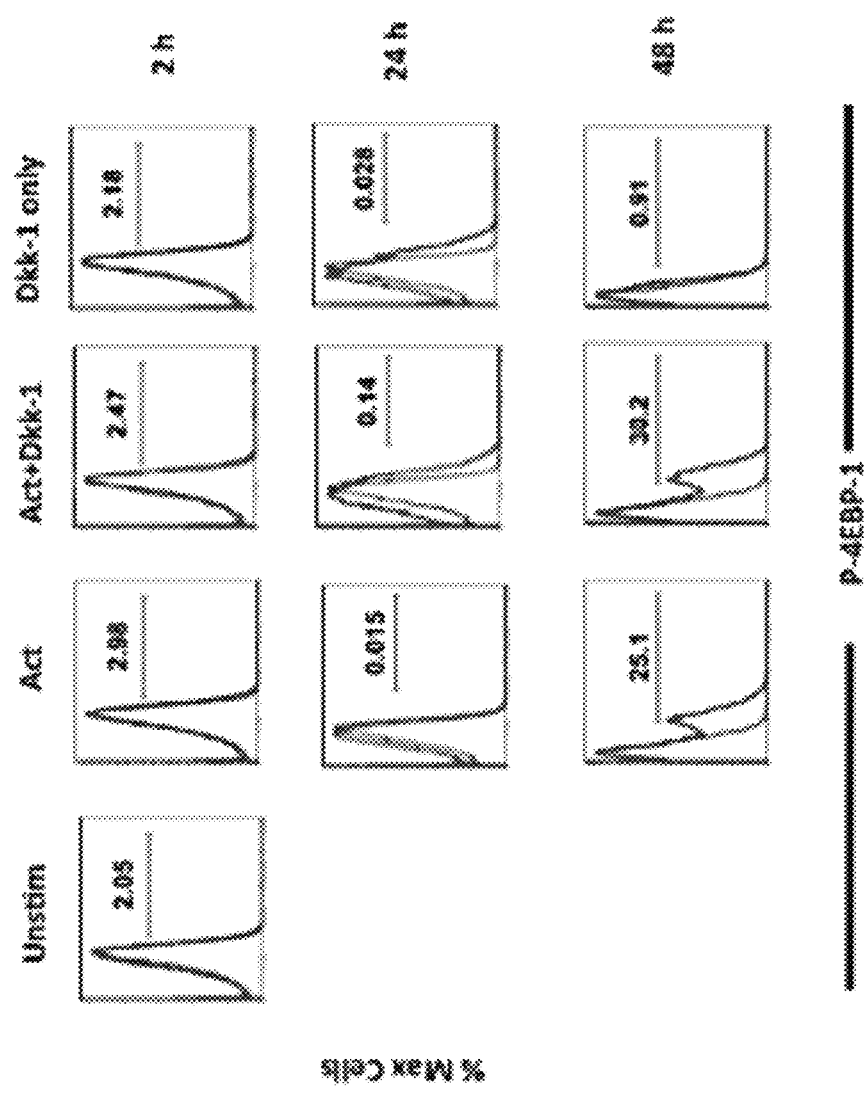
Figures 8E, 8F, 8G:
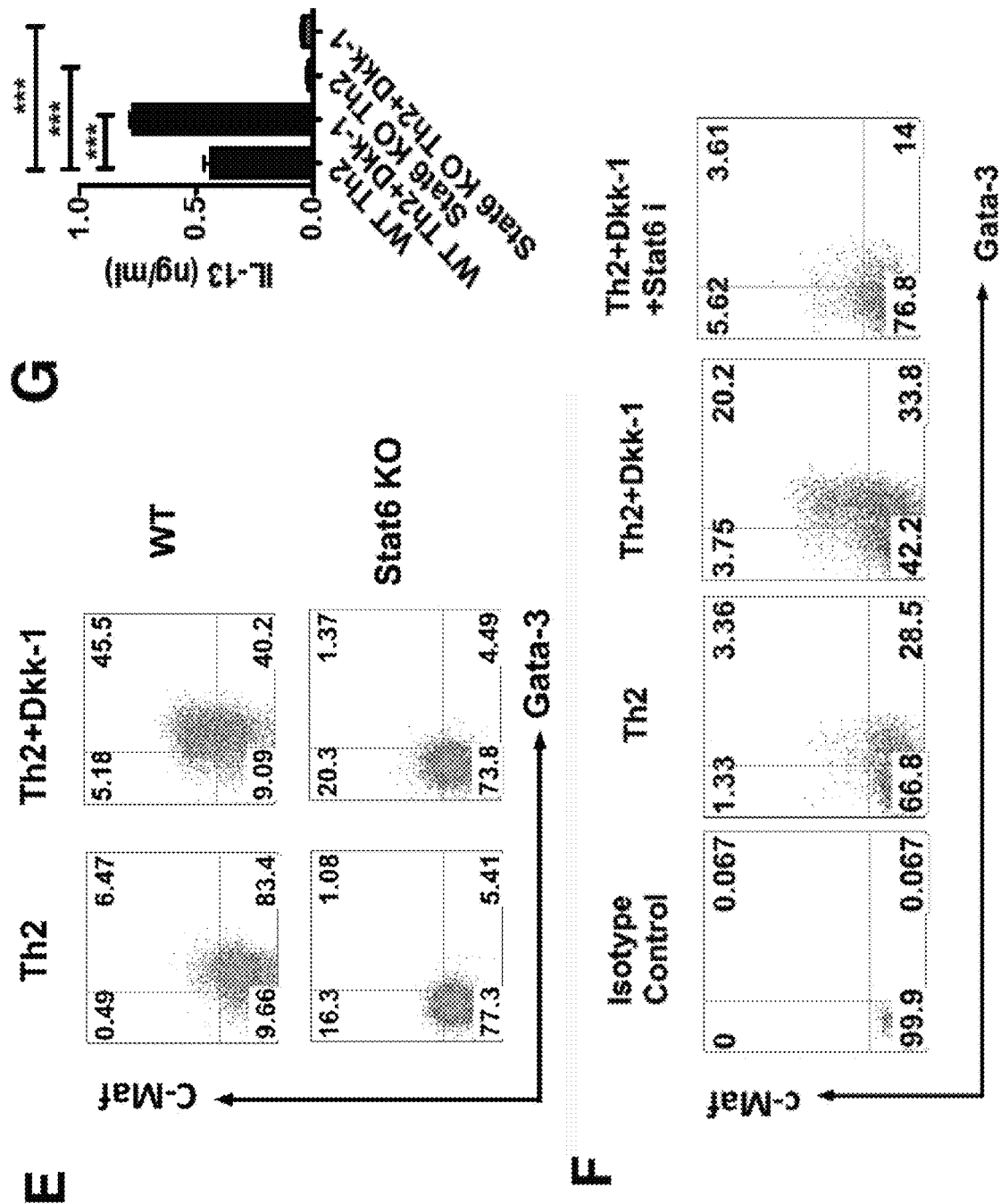

Dkk-1 increased the Gata-3$^+$ and c-Maf$^+$ CD4 T cell population in vitro, and it increased the expression of IL-10 (FIG. 7B). Blockade of IL-4R inhibited the expression of Gata-3 but not c-Maf, revealing that Dkk-1 can induce c-Maf independently of IL-4 signaling (FIG. 7C). In the absence of Dkk-1, T$_H$2 polarization with exogenous IL-4 was mainly induced by Gata-3, and both p38 MAPK and SGK-1 inhibition reduced Gata-3 expression (FIG. 7D, upper panels). The addition of Dkk-1 induced both Gata-3 and c-Maf expressions were markedly. The Inhibition of p38 MAPK regulated c-Maf induction, while SGK (serum glucocorticoid kinase)-1 inhibition primarily reduced the Gata-3 expression in c-Maf$^+$Gata-3$^+$ population (FIG. 7D, lower panels). The marked potentiation of IL-10 secretion by Dkk-1 in T$_H$2 cell polarization conditions was blocked either by SGK-1 or p38 MAPK inhibition, confirming that both kinases are required for Dkk-1-mediated T$_H$2 cytokine secretion (FIG. 8A). Although c-Maf has been known to be predominantly involved in IL-4 expression (Kim et al., 1999, Immunity 10:745-51), these results suggest that Dkk-1 could potentiate other T$_H$2 type cytokines such as IL-10 production in a c-Maf-dependent manner. Based on high homology of the Dkk-1 amino acid sequence (>90%) between mice and humans, human CD4 T cells were treated with mouse Dkk-1 with or without SGK-1 inhibitor. The inhibition of SGK-1 substantially reduced Gata-3 and IL-10 secretion (FIG. 7E). Inhibition of SGK-1 expression by lentiviral shRNA transduction also diminished IL-10 induction by Dkk-1 in human CD4 T cells (Supplementary FIG. 8B). Unlike the SGK-1 inhibition, the phosphorylation of S6 kinase or 4E-BP-1 was not altered by Dkk-1, indicating that the mTORC1 pathway was not affected by Dkk-1 (Supplementary FIGS. 8C and 8D). In addition, Stat6 is also required in Dkk-1-driven T$_H$2 cell polarization (Supplementary FIGS. 8E, 8F and 8G). These data, together with inhibition of Gata-3 expression (by IL-4R blocking antibody) demonstrated in FIG. 4C, suggested that Dkk-1 promotes IL-4 induction, and IL-4 from activated naïve CD4 T cells suppresses TCF-1 and/or Lef expression. Thus, these results showed that Dkk-1 utilized p38 MAPK and SGK-1 to potentiate T$_H$2 cell polarization by increasing expression of c-Maf and Gata-3, respectively.

Figures 9A, 9B, 9C:
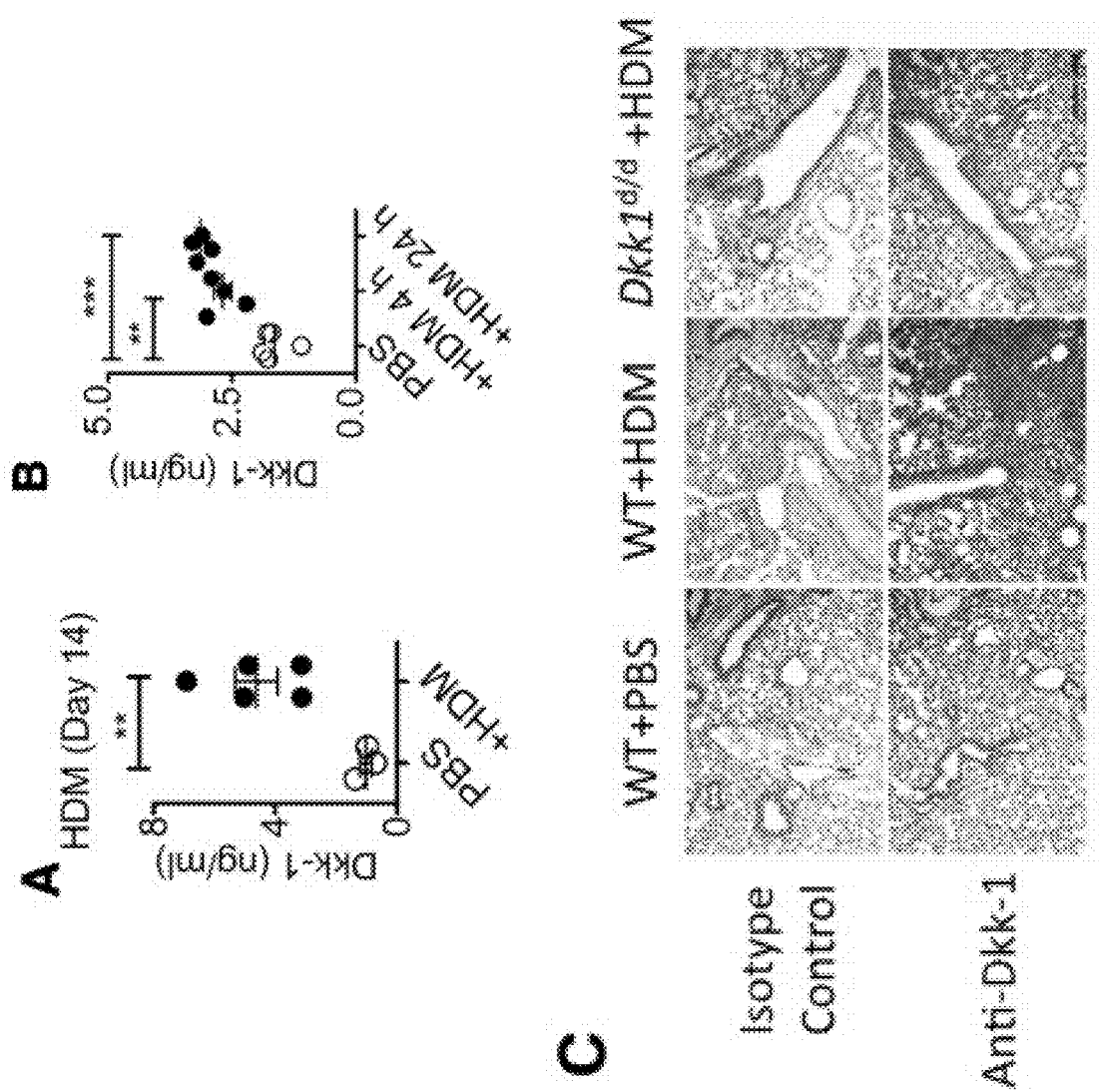
FIG. 9A through FIG. 9L, depicts results of experiments showing circulating Dkk-1 is from platelets upon allergen challenge or parasitic infection.
Figures 9D, 9E, 9F, 9G, 9H:
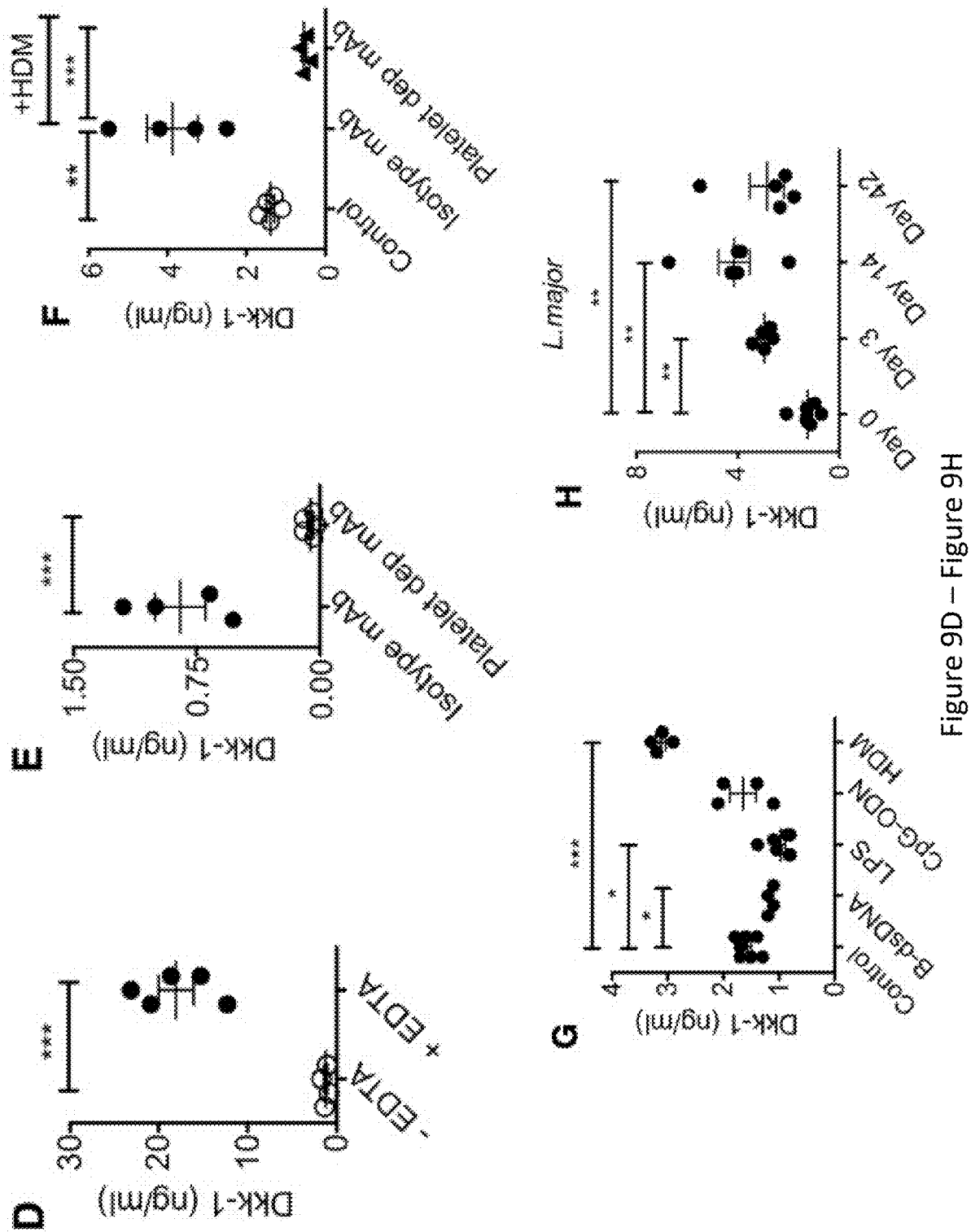

Dkk-1 is Selectively Secreted from Platelets Upon Allergen Challenge or Parasite Infection Based on the pro-inflammatory effect of Dkk-1 in the HDM-induced asthma and the *L. major* infection model, the primary source of Dkk-1 in HDM-induced asthma was investigated. Initially, a marked increase of circulating levels of Dkk-1 following recurrent allergen challenges was found (FIG. 9A). It was further tested whether a single intranasal allergen challenge could induce the elevation of circulating Dkk-1. Dkk-1 was readily elevated in plasma of C57BL/6 mice (FIG. 9B). This increase of Dkk-1 was also detected in the infiltrated lungs from WT littermate control mice while it was markedly reduced in Dkk-1$^{d/d}$ mice, suggesting that the elevation of Dkk-1 does occur both locally and systemically (FIG. 9C). It has been implied that an increase of circulating Dkk-1 in multiple myeloma might be due to platelets (Trikalinos et al., 2009, Br J Haematol 145:262-4). During collection of plasma from C57BL/6 mice, a high Dkk-1 levels were observed even in the homeostatic conditions when samples were collected without anti-coagulant by cardiac puncture (FIG. 9D). Since platelets sense mechanical shear stress by aggregating to form clots and release soluble mediators (Butler, 1995, Lancet 346:841; McGrath et al., 2011, Biomech Model Mechanobiol 10:473-84), it was questioned whether the elevated amounts of Dkk-1 are released from platelets. Platelets were depleted in intact C57BL/6 mice, and it was observed that depletion of platelets abolished circulating levels of Dkk-1 in 12 hours (FIG. 9E). This marked reduction of Dkk-1 by platelet depletion was also observed with HDM allergen challenge (as in FIG. 3B), suggesting that the primary circulating source of Dkk-1 in during both homeostatic and allergen-challenged conditions is platelets (FIG. 9F). Next, it was investigated whether the elevation of Dkk-1 by HDM is a specific response to the allergen. To this end, various types of compounds known as Pattern-Associated Molecular Patterns (PAMPs) were challenged intranasally. Unlike the PAMPs that were tested, HDM could uniquely increase Dkk-1 in circulating blood (FIG. 9G).

Figures 9I, 9J, 9K, 9L:
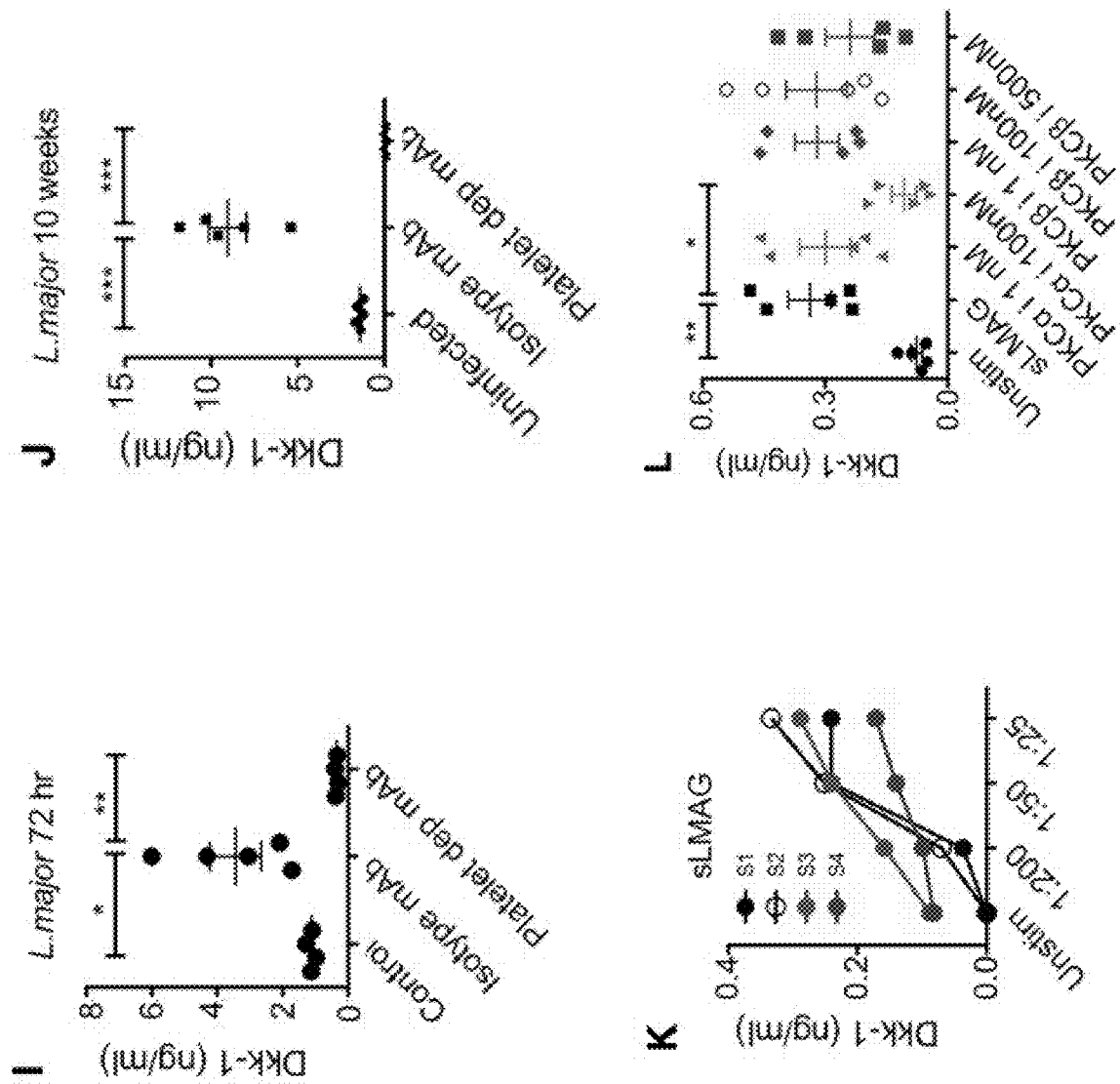
Figure 10:
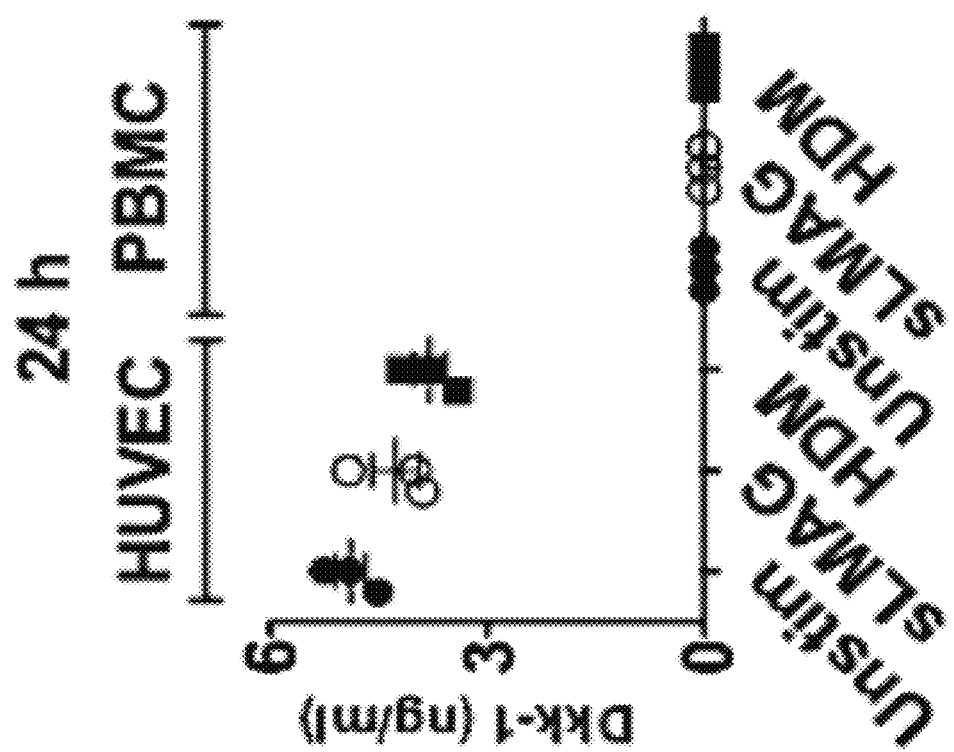
FIG. 10 depicts results of experiments showing Dkk-1 is not induced by sLMAG or HDM in HUVECs or PBMCs. HUVECs ($2\times10^5$/ml) (n=2) or human PBMCs (n=3) ($2\times10^6$/ml) were stimulated with either HDM extract (15 μg/ml) or sLMAG (1:50) for 24 hours in triplicate. Supernatants were harvested and measured by ELISA. A representative of two independent experiments is shown. One-Way ANOVA with Bonferroni's post-hoc test was performed. All results were statistically not significant.

It was further checked whether systemic levels of Dkk-1 are increased by different types of environmental pathogens via skin to promote T$_H$2 responses. The subcutaneous infection of the parasite, *L. major*, in the hindfoot of BALB/c mice increased circulating levels of Dkk-1 which persisted 42 days post-infection (FIG. 9H). Upon parasitic infection, depletion of platelets using platelet-specific anti-mouse GPIbα (CD42b) antibody markedly ablated elevation of circulating Dkk-1 levels, even below homeostatic levels of Dkk-1 in 72 hours (FIG. 9I). At 10 weeks after infection, Dkk-1 is still maintained at a high level, and platelet depletion resulted in the complete loss of Dkk-1 in 12 hours, suggesting that platelets are continuously secreting Dkk-1 (FIG. 9J). Activation of human platelets with sLMAG induced Dkk-1 within 1 hour in a dose-dependent manner (FIG. 9K). Inhibition of PKCα (FIG. 9L) blocked secretion of Dkk-1 upon sLMAG stimulation of human platelets, confirming that activated platelets secrete Dkk-1 from α-granules (Moncada de la Rosa et al., 2013). In contrast, stimulation of human peripheral blood mononuclear cells (PBMCs) or vascular endothelial cells with sLMAG or HDM extract failed to induce secretion of Dkk-1 (FIG. 10). Taken together, these results suggest that Dkk-1 is primarily secreted from platelets upon allergen challenge or non-healing parasite infection, promoting type 2 immune responses.

Figures 11A, 11B, 11C, 11D:
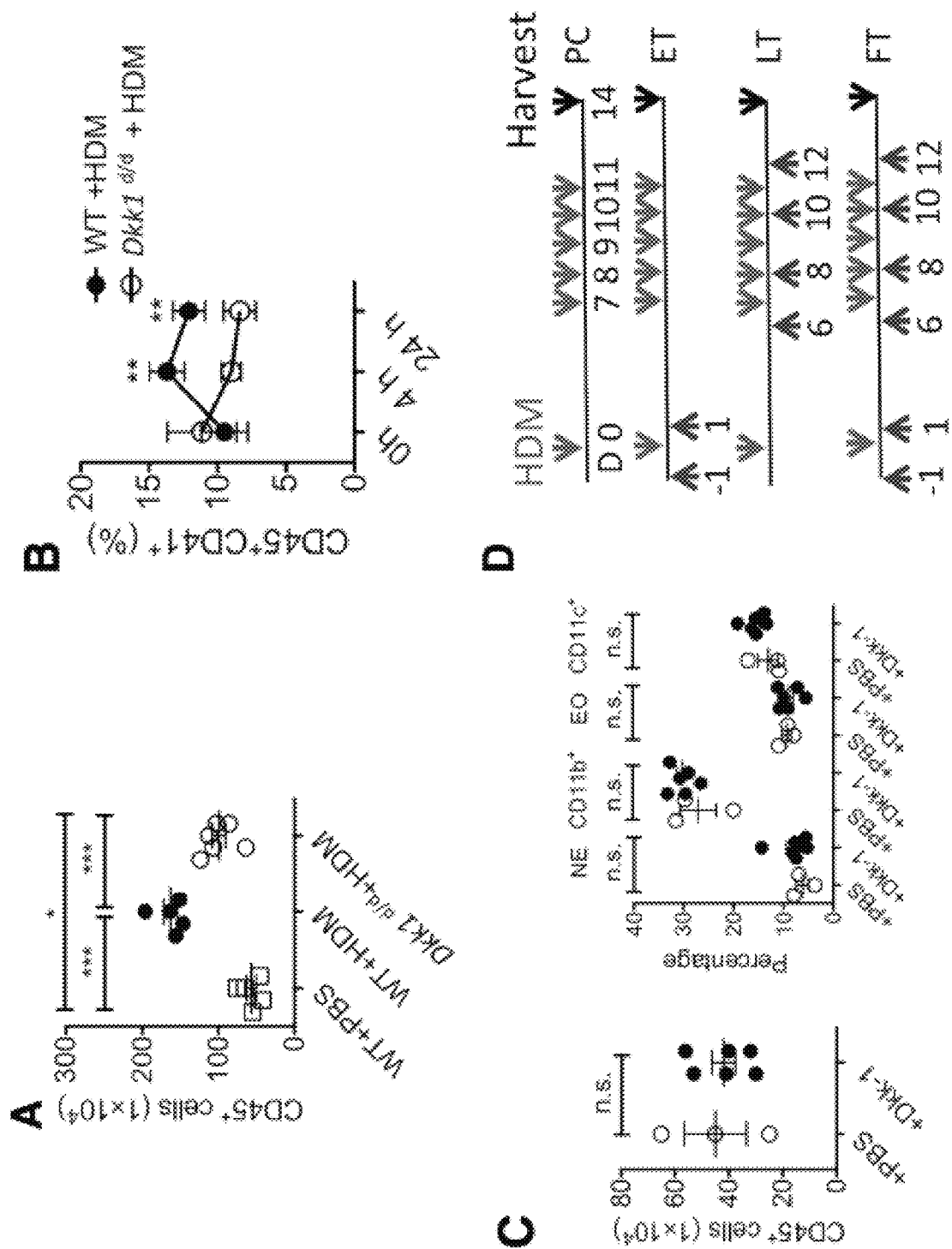
FIG. 11A through FIG. 11J, depicts results of experiments showing Dkk-1 facilitates leukocyte migration and regulates leukocyte-platelet aggregate formation in type 2 inflammation.
Figure 12A:
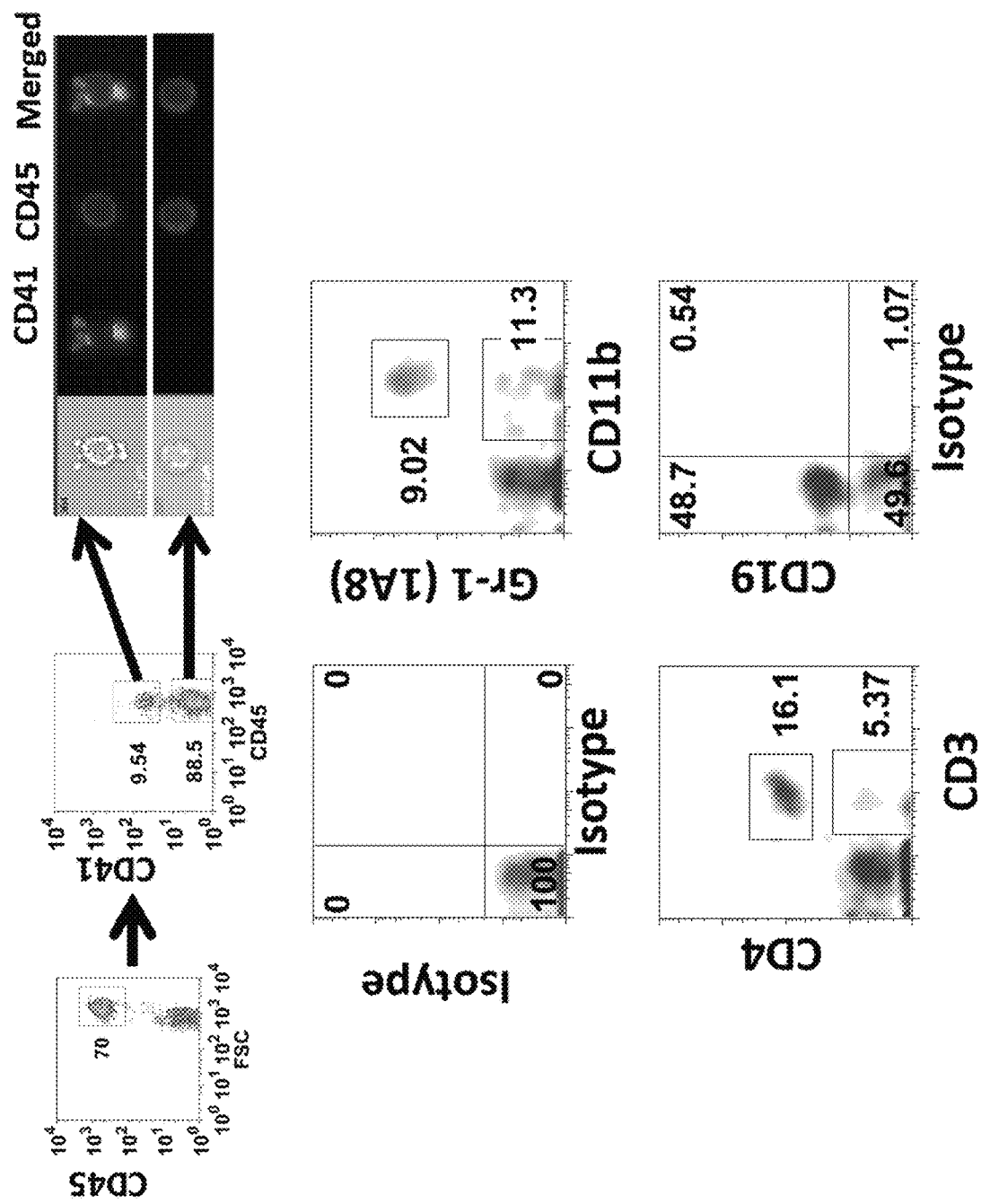
FIG. 12A through FIG. 12G, depicts results of experiments showing regulation of LPA formation by Dkk-1.
Figure 12B:
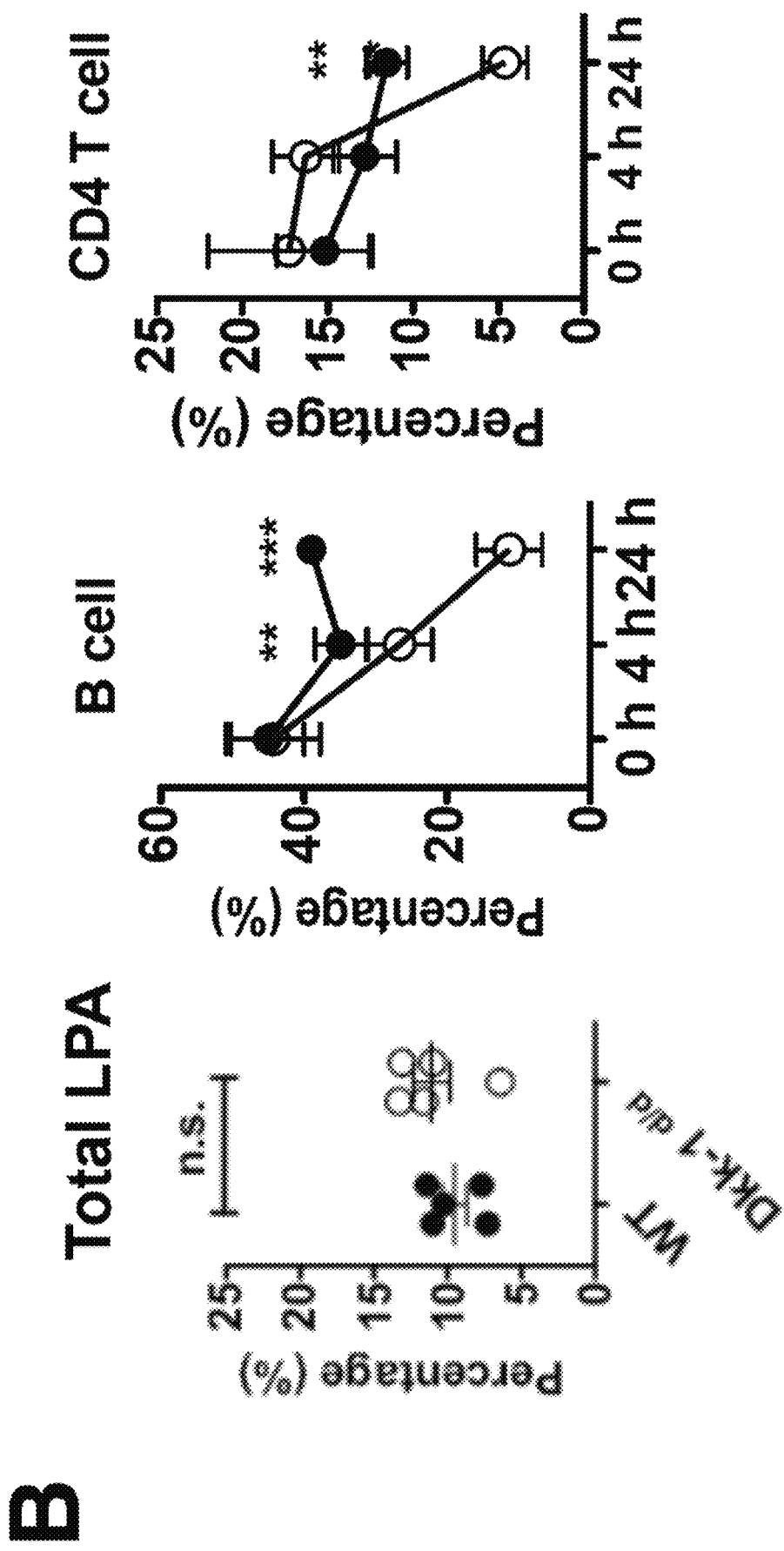
Figure 12C:
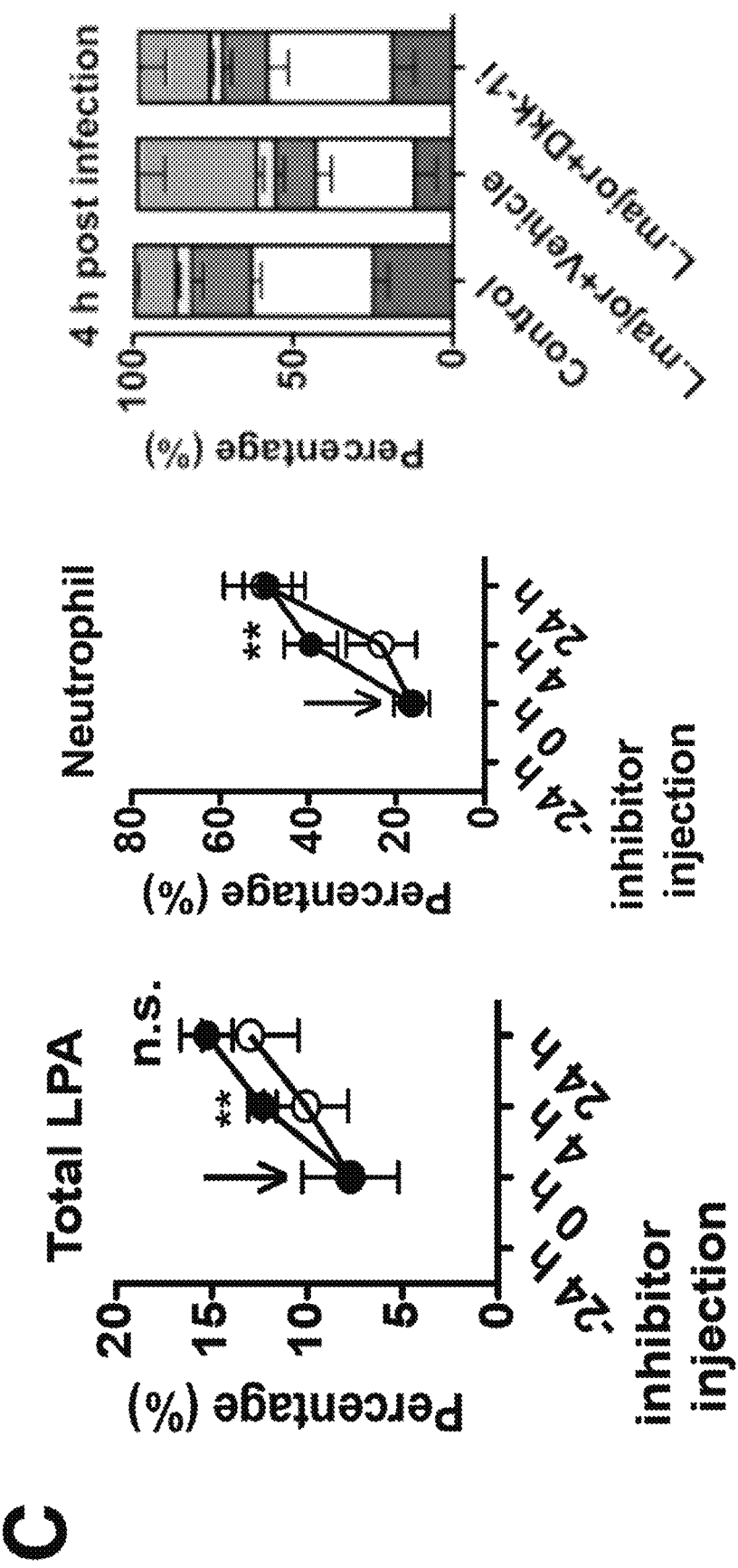
Figure 12D:
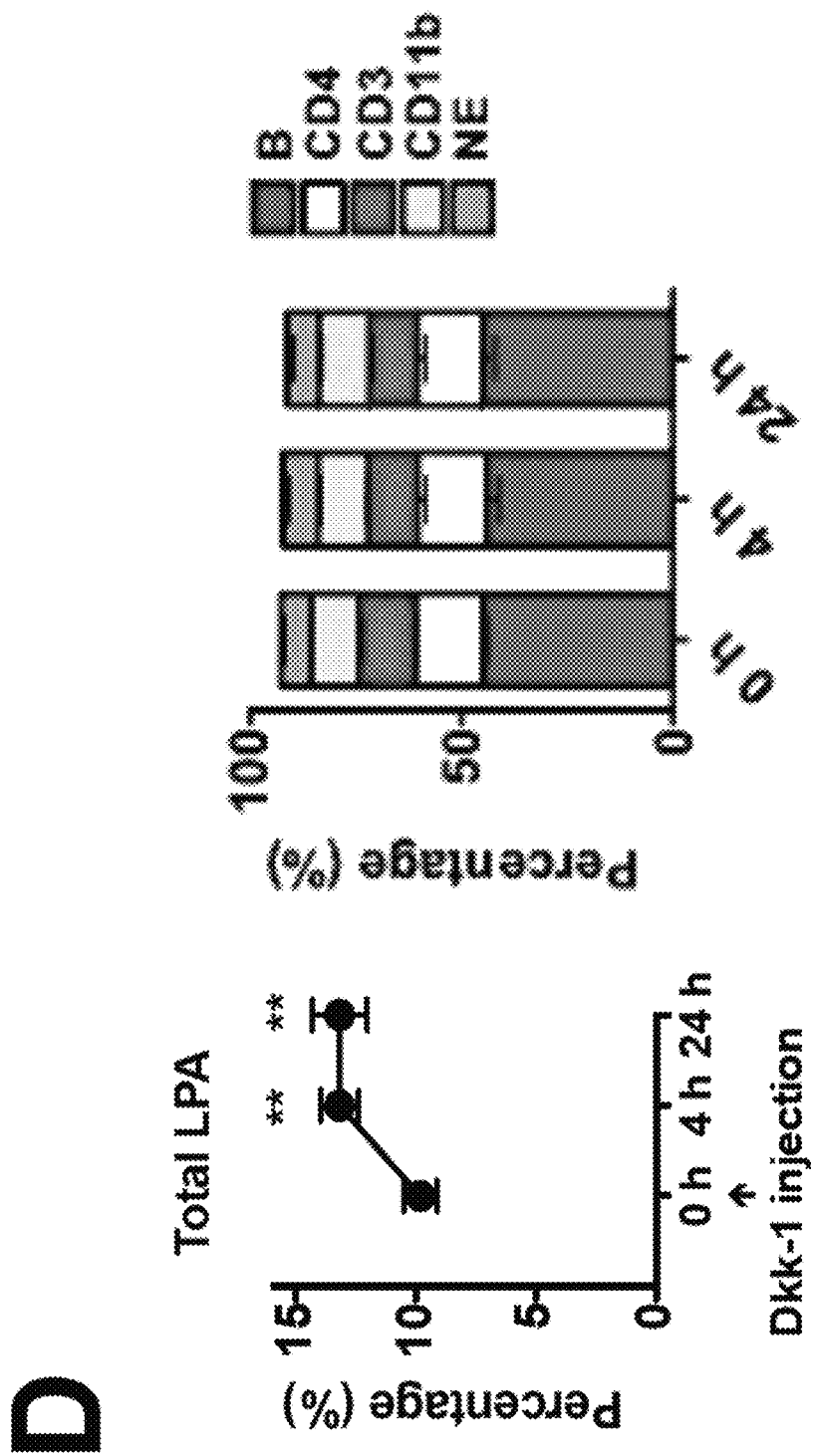
Figure 12E:
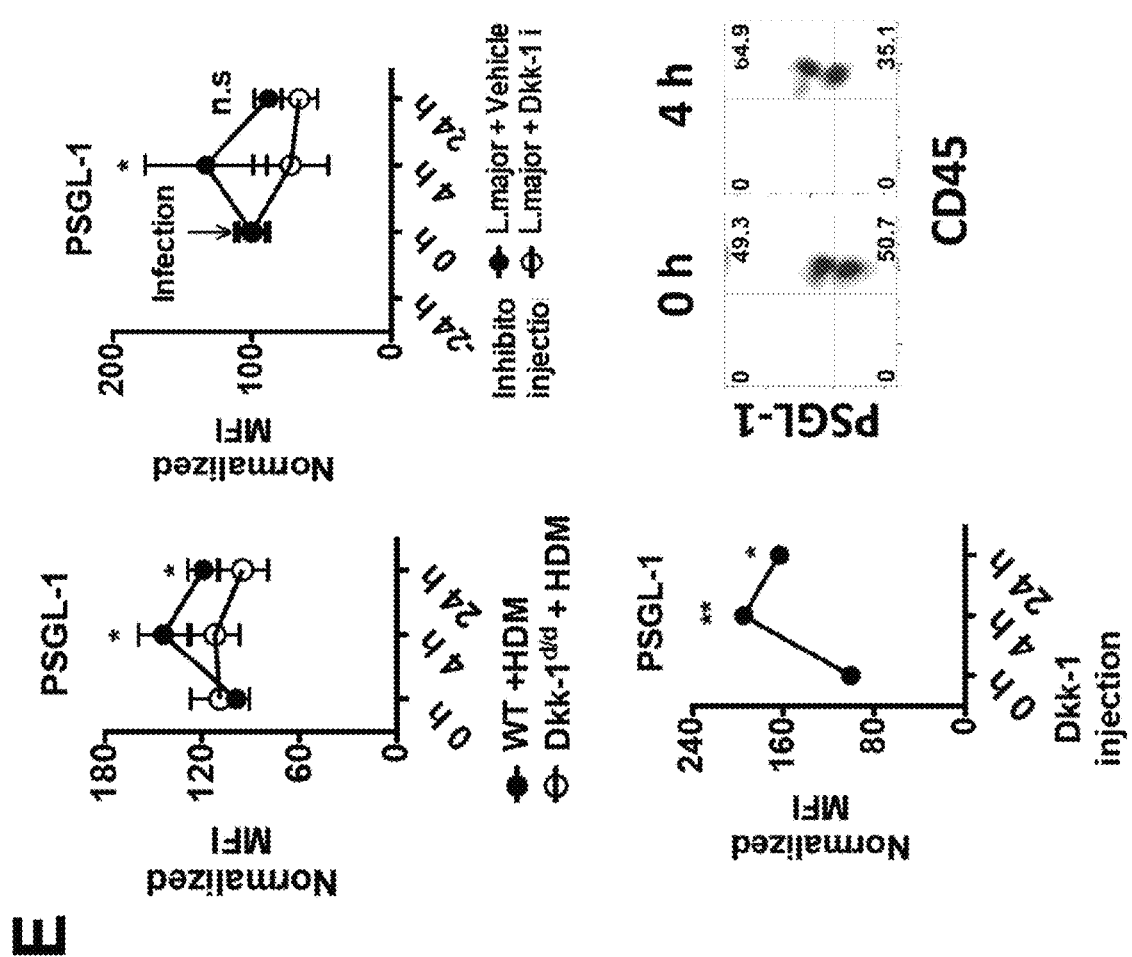
Figure 12F:
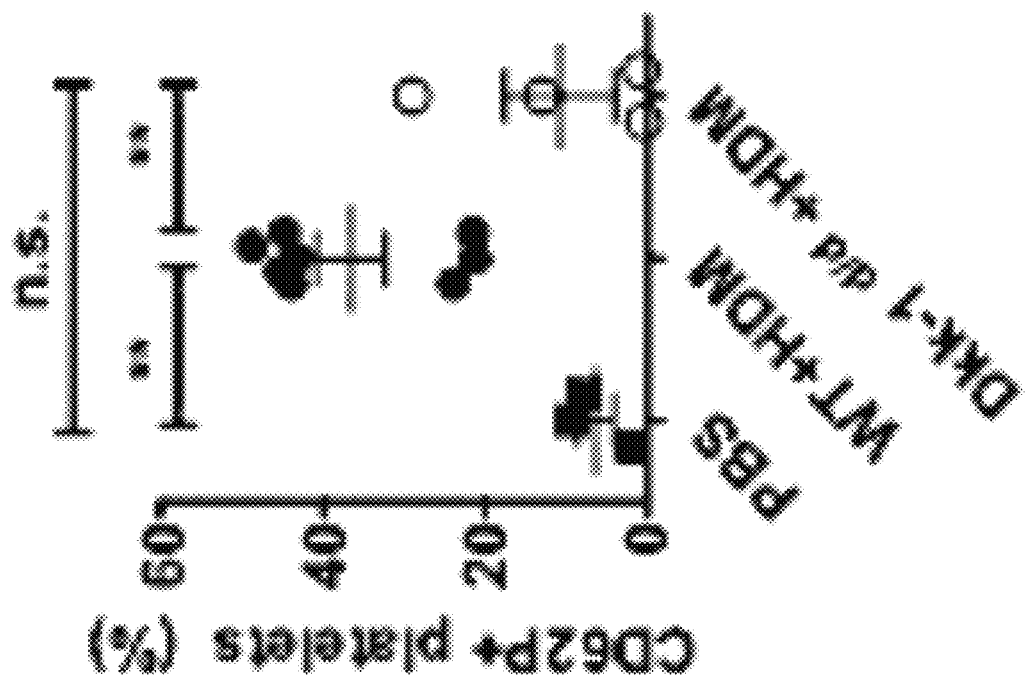
Figure 12G:
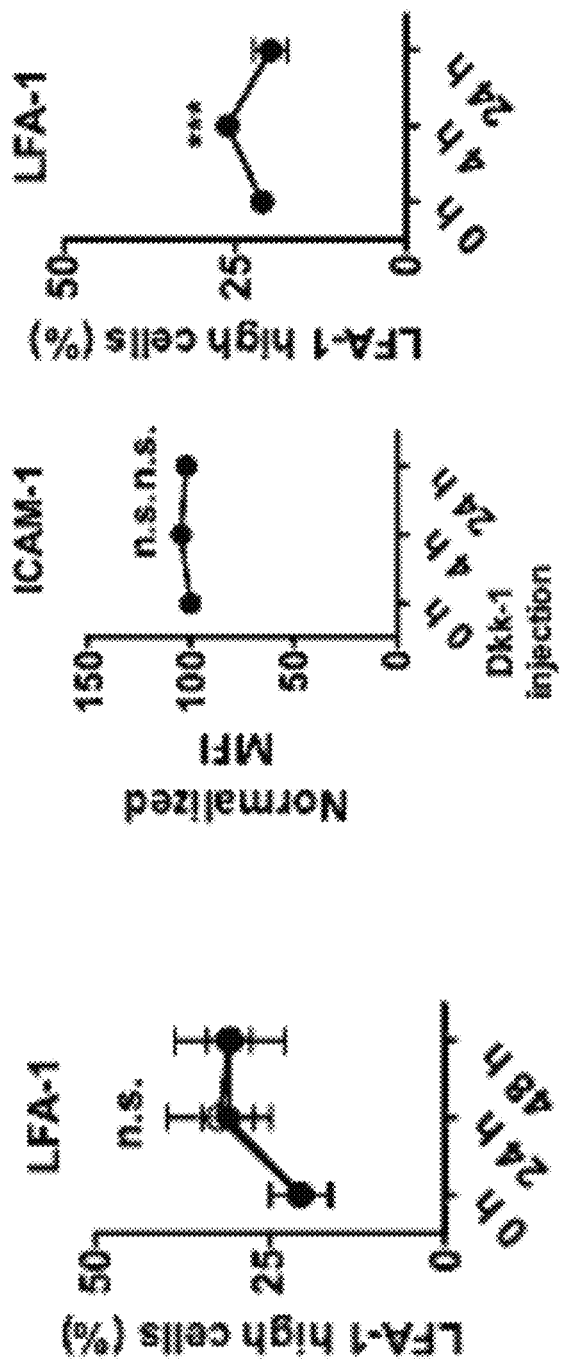
Figure 12G:
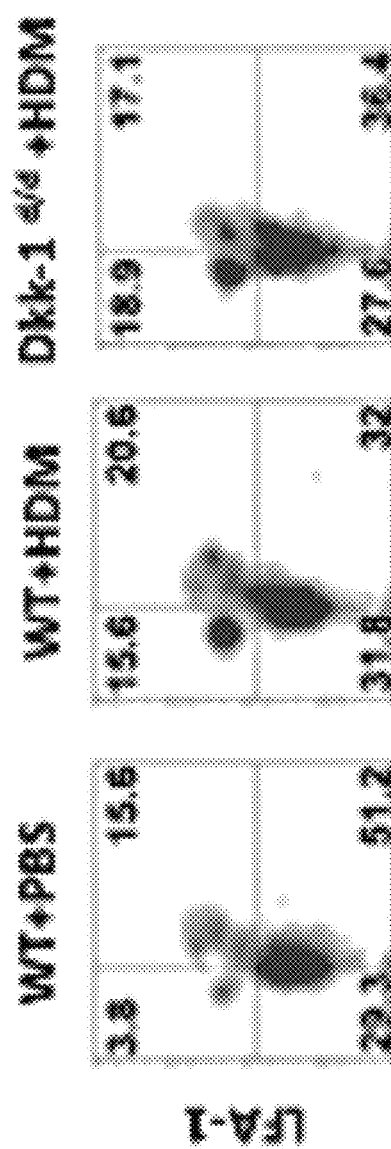

Dkk-1 Facilitates Leukocyte Infiltration and Plays an Important Role in Chronic Type 2 Inflammation Given that the source of circulating Dkk-1 was platelets and Dkk-1$^{d/d}$ mice showed reduced leukocyte infiltration in the lung, it was possible that Dkk-1 may regulate leukocyte-platelet interactions and leukocyte migration into the lung upon HDM extract challenge. LPA (leukocyte-platelet aggregate) formation in human and WT mouse peripheral blood has been considered as a prerequisite for the increases of infiltrating immune cells to the affected tissues to develop immune responses (Ley et al., 2007, Nat Rev Immunol 7:678-89; Li et al., 2012, Adv Hematol 384685; Pitchford et al., 2005, Blood 105:2074-81; Tamagawa-Mineoka et al., 2007, Am J Pathol 170:2019-29; Zarbock et al., 2006, J Clin Invest 116:3211-9). Infiltration of CD45$^+$ immune cells into the lung was significantly increased in WT mice but this was impaired in Dkk-1$^{d/d}$ mice at 72 h following a single allergen challenge (FIG. 11A). Consistent with the marked decrease of leukocyte migration into the lung, a single challenge of allergen induced elevation of LPA (CD45$^+$CD41$^+$ population) in the peripheral blood of WT mice at 4 h and 24 h from the steady state levels but not in Dkk-1$^{d/d}$ mice (FIG. 1B, 12A, 12B). Pretreatment with Dkk-1 inhibitor 24 h prior to infection with the parasite *L. major* similarly reduced the elevation of LPA formation at 4 h post-infection (FIG. 12C). It was further tested whether exogenous Dkk-1 could induce LPA formation and increase leukocyte infiltration in the lung. Exogenous administration of Dkk-1 did not increase the number of infiltrated leukocytes in the lung 72 hours after Dkk-1 protein administration (FIG. 11C) although increased LPA formation was observed without allergen or parasite challenge (FIG. 12D). Combined with results from FIG. 11A, this suggested that infiltration of leukocytes to the lung requires both Dkk-1 and further innate immune responses for leukocyte migration upon allergen challenge. In addition, in contrast to WT mice, leukocytes from peripheral blood in Dkk-1$^{d/d}$ mice failed to sustain the elevation of PSGL-1 expression and its ligand P-selectin on platelets upon HDM allergen challenges. Similarly, inhibition of Dkk-1 in *L. major* infection blocked the increase of PSGL-1 expression (FIG. 12E, 12F, 12G).

Figures 11E, 11F:
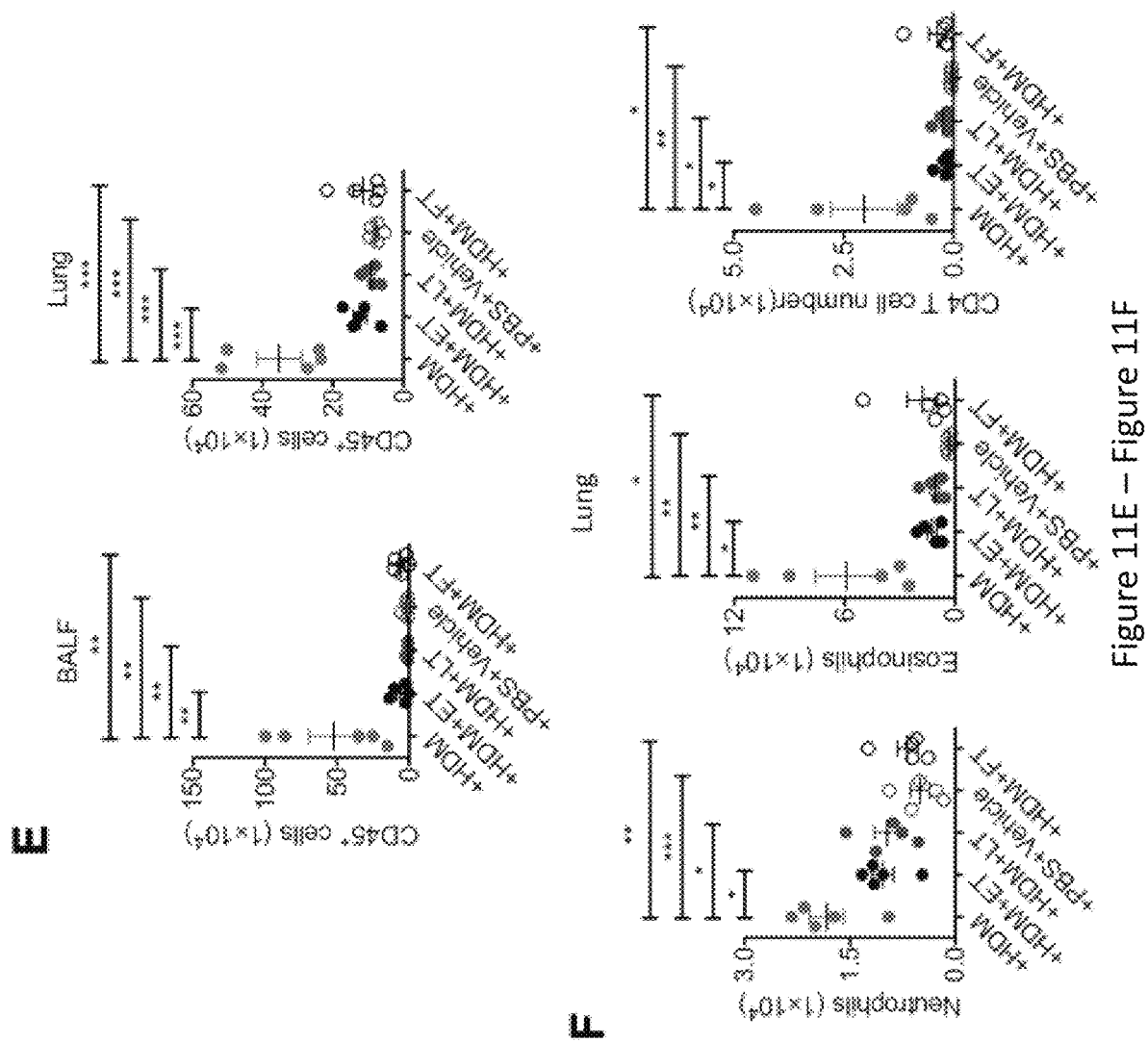
Figures 11G, 11H, 11I, 11J:
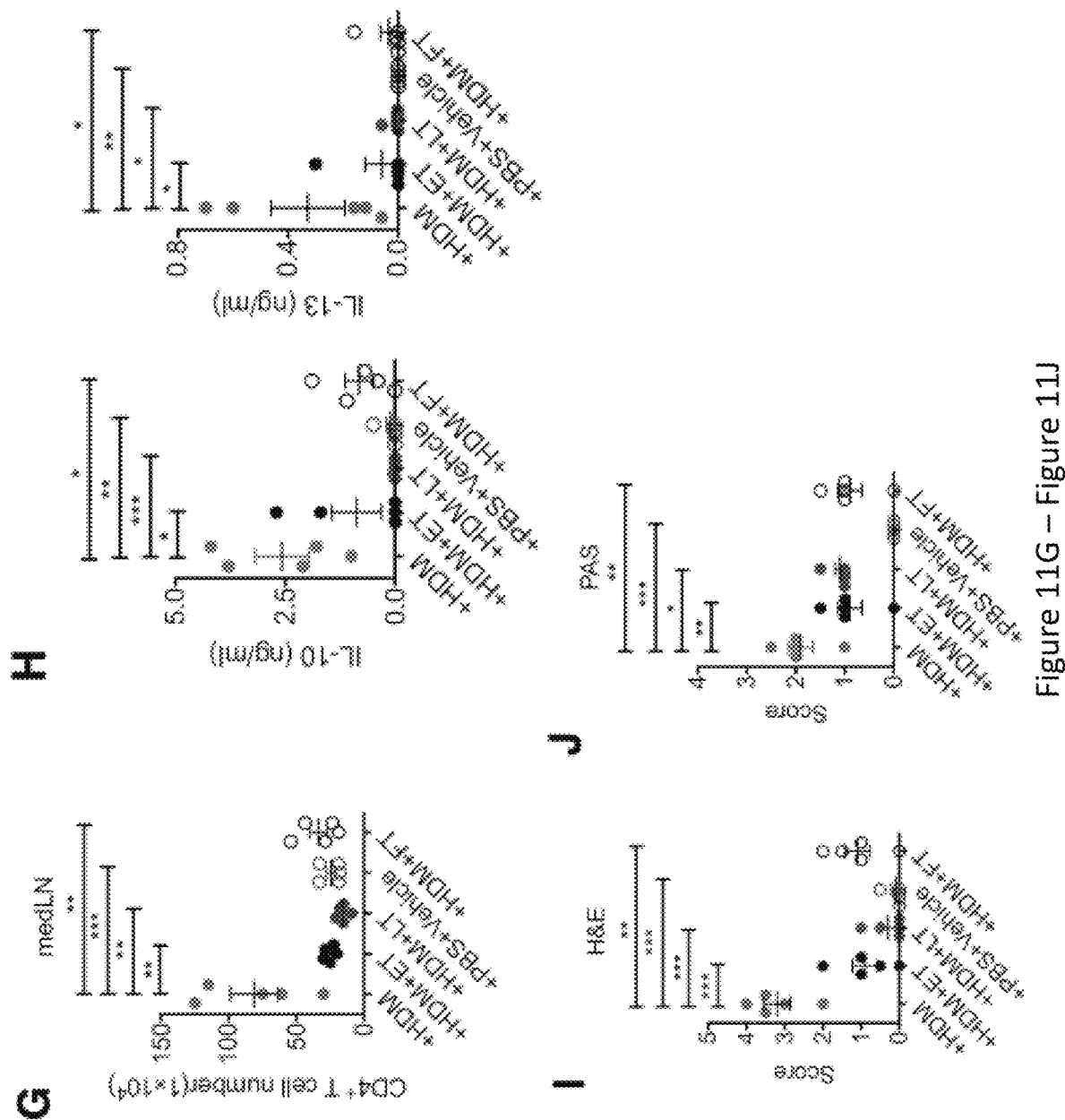
Figures 13A, 13B:
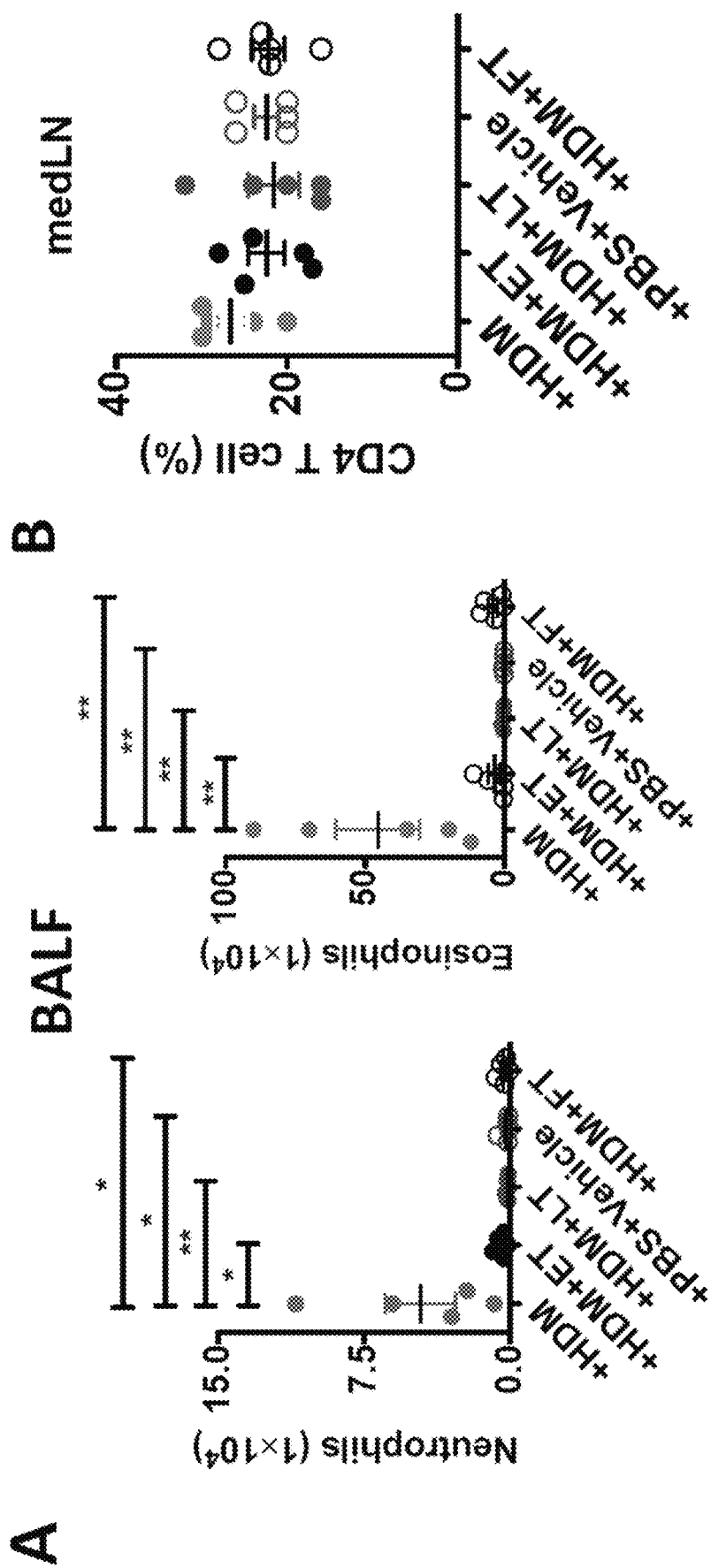

The importance of Dkk-1 was evaluated either at the challenge stage or at the sensitization stage in the HDM-induced asthma model. To this end, Dkk-1 inhibitor was treated either only at the challenge stage (ET, early treatment) or at the sensitization stage (LT, late treatment) (FIG. 11D). Leukocyte infiltration including CD4 T cells, neutrophils, and eosinophils was all markedly decreased in BAL fluid and lung tissues in both the ET and LT treatment protocols (FIG. 11E, 11F, 13A). The number of CD4 T cells was also reduced in mediastinal lymph nodes by inhibiting Dkk-1, but the percentage of CD4 T cells in the lymph nodes did not change (FIGS. 11G, 13). $T_H2$ cytokine secretion from mediastinal lymph nodes was diminished (FIG. 11H). Consistent with these results, histopathological scores also showed that the functional inhibition of Dkk-1 in either the challenge stage or the sensitization stage resulted in inhibition of type 2 inflammatory responses in HDM-induced asthma model (FIG. 11I 11J, 13C). Taken together, these results suggest that Dkk-1 plays an important proinflammatory role for $T_H2$ cell differentiation and leukocyte migration in each stage of HDM allergen challenge to promote chronic type 2 inflammation.

Dkk-1 is a Target for Controlling Type 2 Immune Responses

Figure 14:
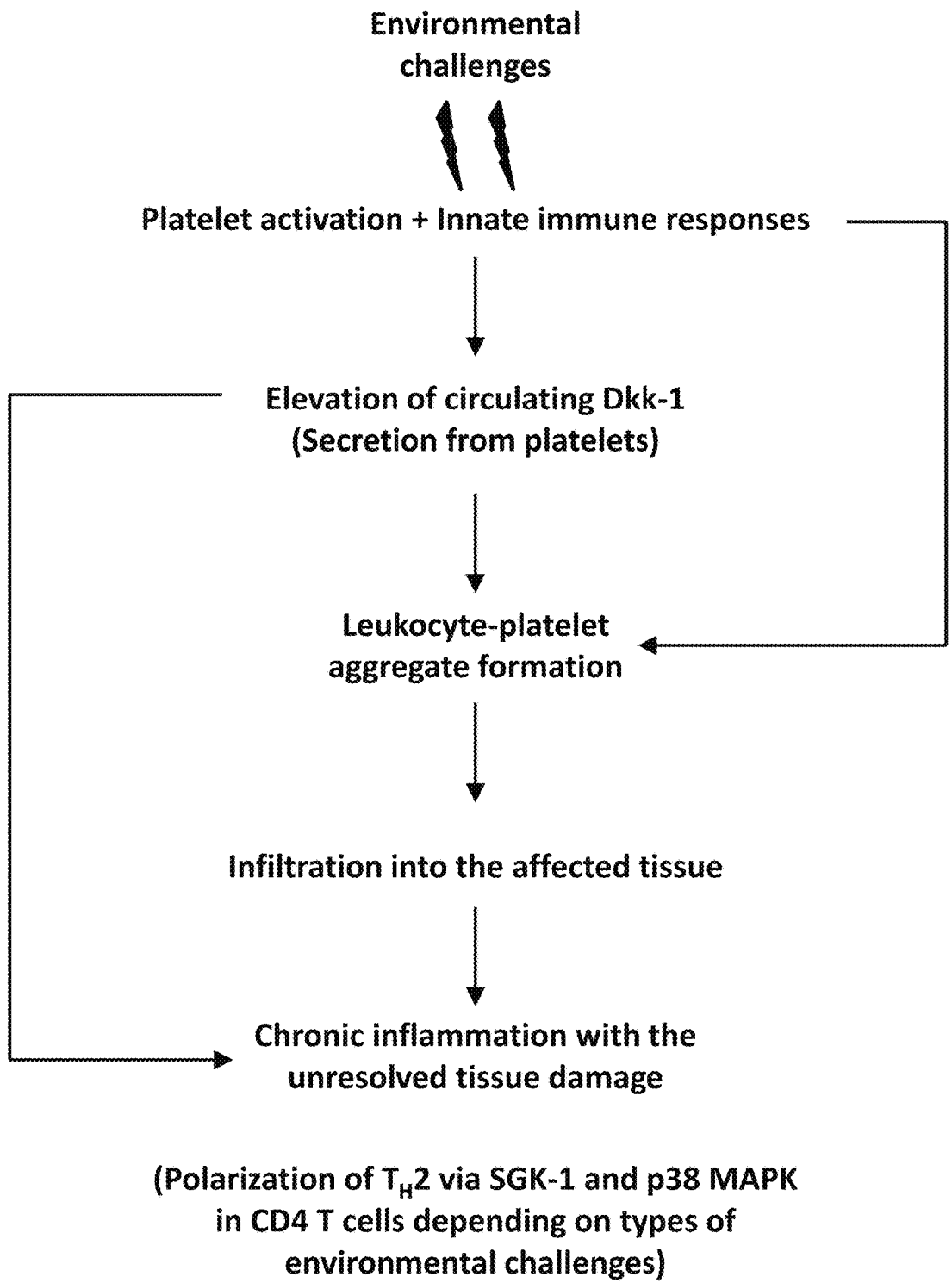
FIG. 14 depicts a schematic diagram of Dkk-1-mediated inflammation. Environmental challenges induce elevated Dkk-1 secretion from activated platelets. The role of Dkk-1 is first to increase leukocyte-platelet aggregate formation in peripheral blood. The increased LPAs facilitate leukocytes infiltration to the affected tissue. When the high level of circulating Dkk-1 is present persistently by recurrent allergen challenge or parasitic infection, CD4 T cell polarization occurs with T cell activation. Dkk-1-mediated $T_H2$ polarization is mediated by SGK-1 and p38 MAPK, resulting in robust $T_H2$ cytokines.

The increased levels of Dkk-1 in peripheral blood have been reported in chronic inflammatory diseases such as various types of cancers, rheumatoid arthritis and lupus (Diana et al., 2007, Nat Med 13:156-63; Sato et al., 2010, Cancer Res 70:5326-36; Wang et al., 2014, PLoS One 9:e84852), and the role of Dkk-1 has been studied as a Wnt antagonist in various model systems. For the first time, the results presented herein demonstrate an important immunomodulatory role of Dkk-1 in type 2 immune responses caused by environmental challenges (FIG. 14).

Although multiple roles of the canonical Wnt signaling pathway have been studied in the context of intracellular mediators such as Apc or β-catenin in T cells and thymocytes (Gounari et al, 2005, Nat Immunol 6:800-9; Guo et al., 2007, Blood 109:5463-72; Staal et al., 2008, Nat Rev Immunol 8:581-93), it is unknown whether Dkk-1 has a role in innate and adaptive immunological responses. These data surprisingly show that Dkk-1 utilizes the MAPK and mTOR signaling pathway components to induce type 2 immune responses/inflammation upon allergen or non-healing parasite infection.

A previous study addressed the role of the canonical Wnt pathway that is mediated by β-catenin in $T_H2$ cell differentiation (Notani et al., 2010, PLoS Biol 8:e1000296), focusing on early progenitor T cells (e.g., thymocytes and naïve CD4 T cells) in vitro. The prediction based on these in vitro studies utilizing high concentrations of Dkk-1 or Wnt3a would have been inhibition of $T_H2$-cell differentiation by Dkk-1, and hence the inhibition of HDM-induced asthma or *L. major* infection. However, these data show that the function of Dkk-1 in vivo at physiological levels is, in fact, the opposite and that Dkk-1 potentiates $T_H2$ cell polarization. Physiologic levels of Dkk-1 (up to 30 ng/ml) in fact promote type 2 inflammation and $T_H2$ cell differentiation primarily through SGK-1 and p38 MAPK. Of note, it was also observed Wnt3a induced Gata-3 expression and non-physiologic high levels of Dkk-1 (>50 ng/ml) inhibited Gata-3 expression similar to the previous report. There are signaling pathways identified which Dkk-1 utilizes other than the well-known canonical Wnt pathway (Fukuda et al., 2010, Differentiation 80:46-52; Krause et al., 2014, Cell Death Dis 5:e1093). It is notable that Dkk-1 has a colipase domain in its carboxy-terminal region that is responsible for Wnt antagonist activity, but the function and role of the N-terminal domain of Dkk-1 is largely unknown (Brott and Sokol, 2002, Mol Cell Biol 22:6100-10). Collectively, these findings suggest that physiological concentrations of Dkk-1 utilized SGK-1 and p38 MAPK under type 2 immune responses/inflammation.

Recent studies pointed out the specificity of platelet activation and its immunomodulatory role in addition to its traditional role in coagulation events and hemostasis (Rondina and Garraud, 2014, Front Immunol 5:653). Platelets do express a variety of receptors for PAMPs, and recent studies identify more receptors and ligands that are expressed in immune cells (Semple et al., 2011, Immunology 11:264-74). The data presented herein demonstrates that platelets are an important source of Dkk-1 in the models and the release of Dkk-1 is specific to environmental challenges that lead to chronic type 2 immune responses. Platelets are the most abundant source of TGF-β1 (Kim et al., 2013, J Biol Chem 288:34352-63). Although the release of TGF-β1 could be assumed in platelet activation and thus further assumed to increase Foxp3+ CD4 T cells, it should be noted that platelets also possess ligands such as PF4 (CXCL4) which is abundantly present and can inhibit TGF-β1-mediated T cell differentiation (Shi et al., 2014, J Clin Invest 124:543-52). The inhibition of TGF-β1-mediated Foxp3 expression by Dkk-1 suggests that the immunosuppressive function of TGF-β1 in a given microenvironment would be potently inhibited, and hence Dkk-1 would be able to generate robust $T_H2$ cytokines. Together with the inhibitory role of Dkk-1 on TGF-β1-mediated Foxp3+ T cell differentiation, it is unlikely that TGF-β1 would affect T cell differentiation in these models. Additionally, it was not observe any increased level of Foxp3+ T cells in doubleridge mice, confirming that platelet activation and subsequent Dkk-1 release from platelets is specific to a given environmental challenge.

These findings may suggest that immunomodulation of Dkk-1 from platelets is an example of the development of the mammalian immune system from the hemocyte system that exists in *Drosophila* (Lavine et al., 2002, Insect Biochem Mol Biol 32:1295-1309; Wood and Jacinto, 2007, Moll Cell Biol 8:542-51). The results from exogenous Dkk-1 injection and HDM-induced asthma and *Leishmania major* infection model suggest that platelet activation and subsequent release of Dkk-1 facilitates leukocytes migration to the site of environmental challenges, and this should be coordinated with the recognition of such challenges by innate immune cells. Since hemocytes play both roles of platelets and innate immune cells, these results may show the specialized role of platelets and leukocytes to coordinate type 2 immune responses in mammals. It is notable that the potent induction of IL-10 by Dkk-1 in the *L. major* infection model demonstrates that the parasite utilizes Dkk-1 as a strategy to reconcile immune-activation and immunosuppression to favor parasite survival, avoiding complete eradication and maintaining lesions.

Taken together, these findings highlight the importance of the orchestrating role of Dkk-1 from platelets to facilitate leukocyte migration and further to polarize immune responses by inducing $T_H2$ cell polarization, placing Dkk-1 as a highly attractive target for controlling type 2 immune responses.

Example 2

Determination of the Role of Dkk-1 in Endotypes of Severe Asthma

After exposure to inhaled house dust mite (HDM) allergen and release of thymic stromal lymphopoietin (TSLP), Dkk-1 synergizes with TSLP to stimulate Th2 development and reactivation. Thus, as a result of exposure to an environmental allergen, release of this platelet-derived factor activates immune pathways that may regulate asthmatic inflammation. Preliminary studies also show that Dkk1 expression in human sputum has a striking association with asthma severity. Interestingly, Dkk-1 was not elevated in asthmatics of all severities, nor was Dkk-1 associated with atopy or other markers of "Th2 high" asthma. Thus, Dkk-1 elevation in the airway has a specific association with severity. Dkk-1 protein is measured in the blood to clarify this association with asthma and the endotypes of asthma that have elevation of Dkk-1 are determined. Single cell RNA-seq is used to define the cell populations producing Dkk-1, and CyTOF analysis is used to define specific effects of Dkk-1 on cells in the airways.

The Dkk-1 data provides a novel mechanism by which platelets release Dkk-1 that drives allergic inflammation. Data presented herein demonstrates that this novel mediator of inflammation is identified in sputum of severe asthmatics suggesting Dkk-1 is an innovative target for asthma treatment that may block vascular leak and reduce antigen exposure.

The results from experimental example 1 show that Dkk-1 function is critical for asthma-like pathogenesis in a mouse model of house dust mite (HDM)-induced asthma. These studies are extended herein to show that Dkk-1 expression is associated with asthma severity in humans. Moreover, experimental example 1 demonstrates that platelets are an important source of Dkk-1 in both humans and mice, leading to release in the serum. Platelet activation in asthma is well known to promote disease through a variety of mechanisms (Idzoko, 2015, J Allergy Clin Immunol 135:1416-23). Thus, these findings provide novel and strong support that Dkk-1 may impact asthma pathogenesis.

Experiments using mice expressing only very low levels of Dkk-1 (hypomorphic doubleridge mice, Dkk-1$^{d/d}$) repeatedly exposed to intranasal HDM, demonstrated that the Type 2 immune response to HDM was almost completely impaired (FIGS. 3B, 3C, 3E, 9A). To define the mechanism by which Dkk-1 drives this asthma-like response the ability of recombinant Dkk-1 to induce Gata-3 or other transcription factors essential for T cell development was tested. Dkk-1 strongly stimulates CD4 T cells to become $T_H2$ cells. Depletion of platelets by in vivo by injection of anti-CD42B also eliminates Dkk-1 from peripheral blood. In addition anti-TSLP also reduces the induction of Dkk-1 in response to HDM. Thus it is hypothesized that TSLP is important for the induction of Dkk-1 and may cooperate with Dkk-1 in driving the asthma response perhaps by their receptors on platelets.

Figure 15:
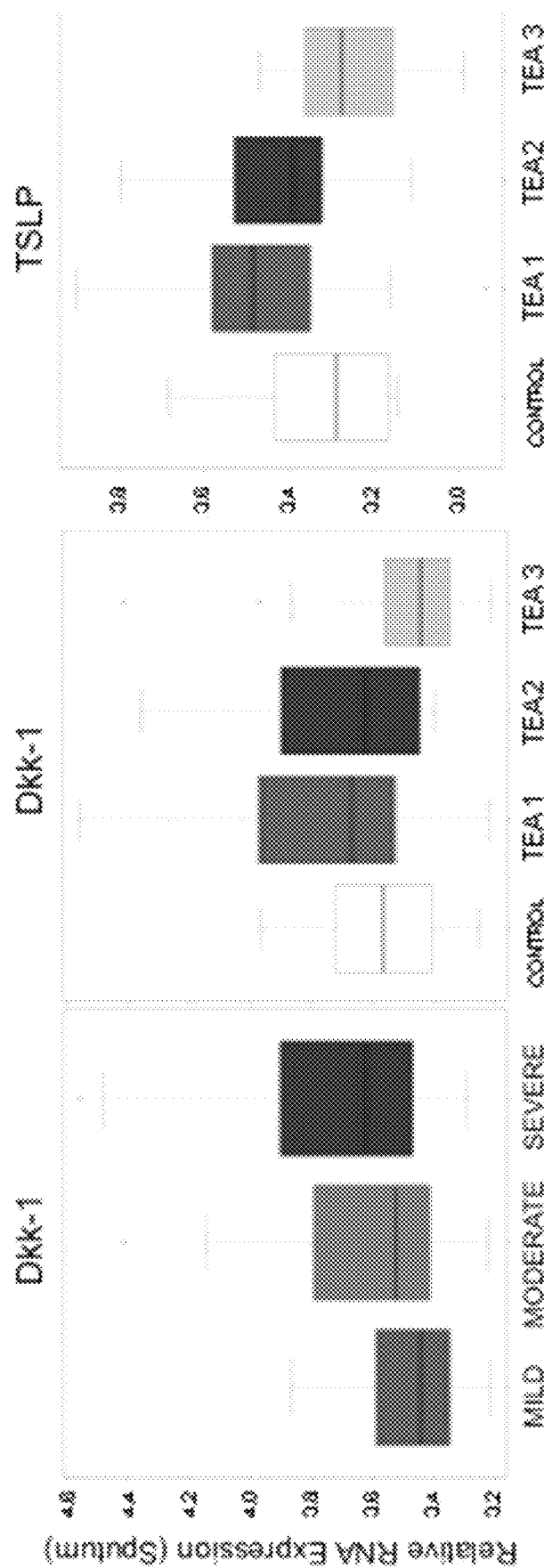
FIG. 15 depicts results of experiments showing increased expression of Dkk-1 and TSLP in sputum microarray analyses. Left panel is from all asthmatics based on clinical criteria of severity (p=0.004), middle (p=5.7×10-5) and right (p=9.2×10-7) panels expression in TEA clusters. X-axis defines the groups.

Dkk-1 gene expression in the sputum was significantly associated with asthma severity and in the most severe clusters 1 and 2 of the TEA (transcriptomic endotypes of asthma) analysis (Yan et al., 2015, Am J Respir Crit Care Med 191:1116-25). Thus, it appears that in asthma, Dkk-1 is highly expressed in the respiratory tract, at the site of inflammation, possibly leading to release of Dkk-1 into the blood. TSLP, shown be required to induce expression of Dkk-1 in platelets, was also increased in sputum expression data, based on asthma severity and in the severe TEA clusters 1 and 2, as shown (FIG. 15). These data show a significant association of the Dkk-1 pathway with asthma severity. Dkk-1 expression in sputum was also positively associated with other markers of severe asthma, including number of asthma exacerbations in the past year, dose of inhaled corticosteroid and percentage of bronchial epithelial cells in the sputum, suggesting that epithelial damage and severity may be markers of Dkk-1 elevation in asthma. While a large majority (88%) of the asthmatic subjects in the YCAAD cohort was atopic, Dkk-1 expression in sputum was not elevated in the total asthmatic population, nor was Dkk-1 elevation significantly associated with elevated sputum or blood eosinophils or fraction of exhaled nitric oxide (FENO). These data suggest that Dkk-1 is not merely a marker of atopy or a "Th2 high" asthmatic population. Based on these data, without wishing to be bond to any particular theory, it is contemplated that Dkk-1 is elevated in a subset of asthmatics subjects with severe disease and in these populations Dkk1 induced inflammatory pathways promote persistence of disease. Asthma subpopulations having elevations in Dkk-1 are defined with a focus on epithelial damage and reactivity to specific allergens, and the biological pathways in the airway that drive Dkk-1 are examined.

These data show that Dkk-1 expression in sputum correlates with asthma severity. Dkk-1 is produced by activated platelets and was elevated in blood in models of asthma. It is hypothesized that Dkk-1 is elevated in a subset of asthmatic subjects and promotes disease. The subsets of asthmatics with elevations of Dkk-1 are delineated and the pathways by which Dkk-1 influences disease are examined to determine if Dkk-1 in serum is associated with asthma severity. Dkk-1 is measured in serum and sputum supernatants of 200 asthmatic and 50 non-asthmatic, healthy control subjects by multiplex ELISA. This assesses if Dkk-1 protein in serum parallels its expression in the sputum and if expression in the sputum is reflected in protein in the sputum supernatant.

The subset of asthmatics that express high Dkk-1 is defined and associations with other pathways are analyzed. A Dkk-1 association with subjects with sensitivity to HDM is determined using data from subjects including ImmunCAP.

It is determined if Dkk-1 is produced in the airway and define its source. These studies show that sputum expression of Dkk-1 correlates with asthma severity. It is hypothesized that Dkk-1-producing cells in sputum contribute to inflammation and asthma severity. The major source is from activated platelets, therefore one possibility is that platelets might be an important source of Dkk-1 in sputum. RNA-Seq data analysis from sputum and single cell analysis is used to define the in vivo source of Dkk-1. Moreover, the cells that express TSLP (Thymic stromal lymphopoietin) and TSLP-R (receptor) are assessed to give insights into the interactions among cells in the sputum. Human platelets express TSLP- R. Elevation of Dkk-1 in the serum and increased expression of Dkk-1 in platelets, may suggest that platelets are activated in the respiratory tract where they release Dkk-1.

The effects of Dkk-1 on sputum and blood cell cytokine production and surface marker expression and cellular differentiation are defined. Blood and sputum cells are stimulated with Dkk-1 in vitro. Cells treated versus untreated are compared using CyTOF for cytokine expression, including type-2 cytokines IL-4, IL-5, IL-13 and IFN-γ and IL-17 and markers of alternative activation (CD206). The activation status of platelets from subjects with elevated Dkk-1, are determined as described in experimental example 1, which includes CD62P, TSLP-R and additional adhesion molecules. The cellular responses of platelets to HDM are also evaluated for induction of CD62P, TSLP-R and additional adhesion molecules.

Figure 16:
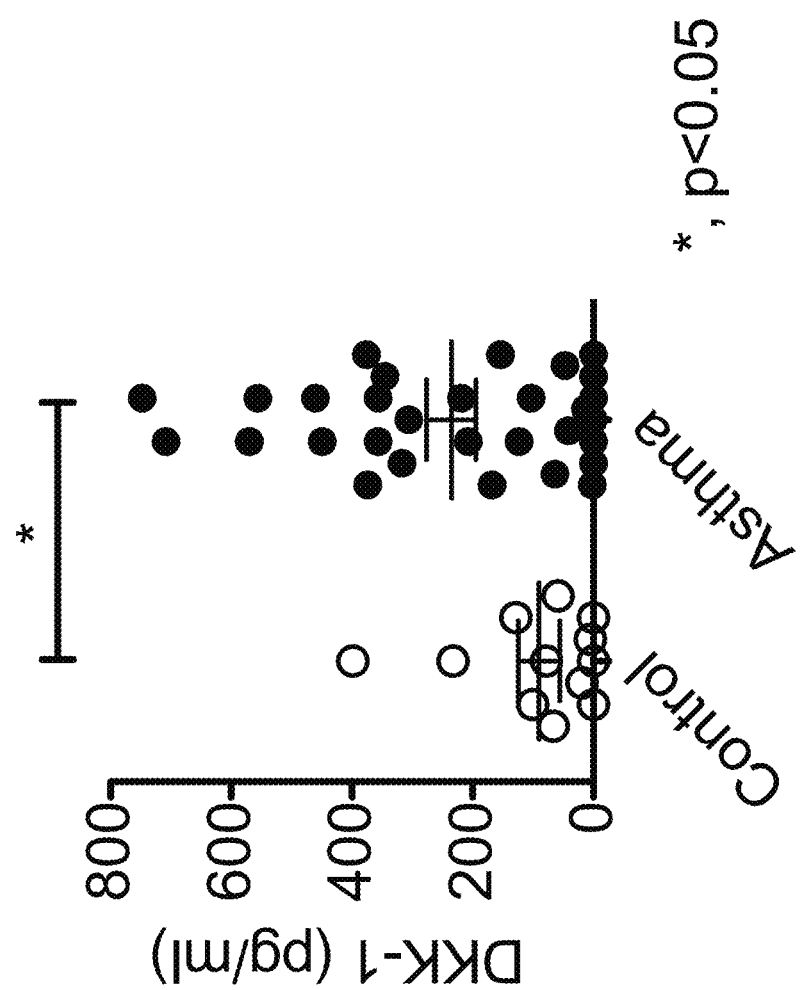
FIG. 16 depicts results of experiments showing human asthma patients showing elevated DKK-1 expression compared to control patients. Sputum samples from healthy volunteers (n=12) and asthma patients (n=30) were analyzed by human DKK-1 ELISA. *, p<0.05. Student's t-test was performed.

Further experiments showed that human asthma patients show elevated Dkk-1 expression compared to controls (FIG. 16).

Example 3

The Anti-Dickkopf-1 Monoclonal Antibodies Protect Against Pathological Type 2 Inflammation As described in Example 1, a Dkk-1 small molecule inhibitor protects BALB/c mice from both chronic inflammation caused by *L. major* and house dust mite (HDM)-induced asthma. The results presented herein demonstrate that an anti-Dkk-1 monoclonal antibody protects BALB/c mice from both chronic inflammation caused by *L. major* and house dust mite (HDM)-induced asthma.

Figures 17A, 17B:
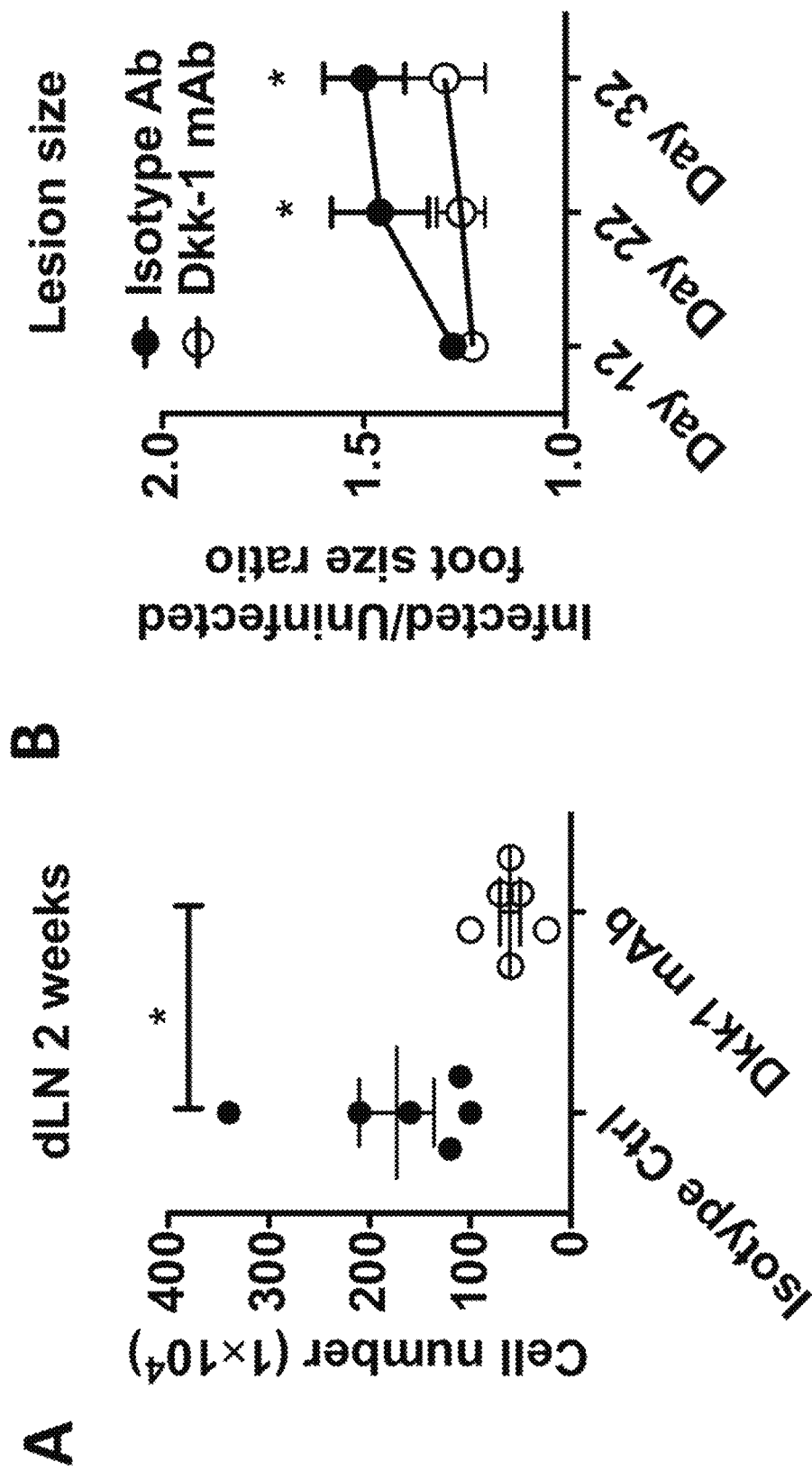
FIG. 17A and FIG. 17B, depicts results of experiments showing a Dkk-1 monoclonal antibody treatment protects BALB/c mice from chronic inflammation caused by L. major.
Figure 18:
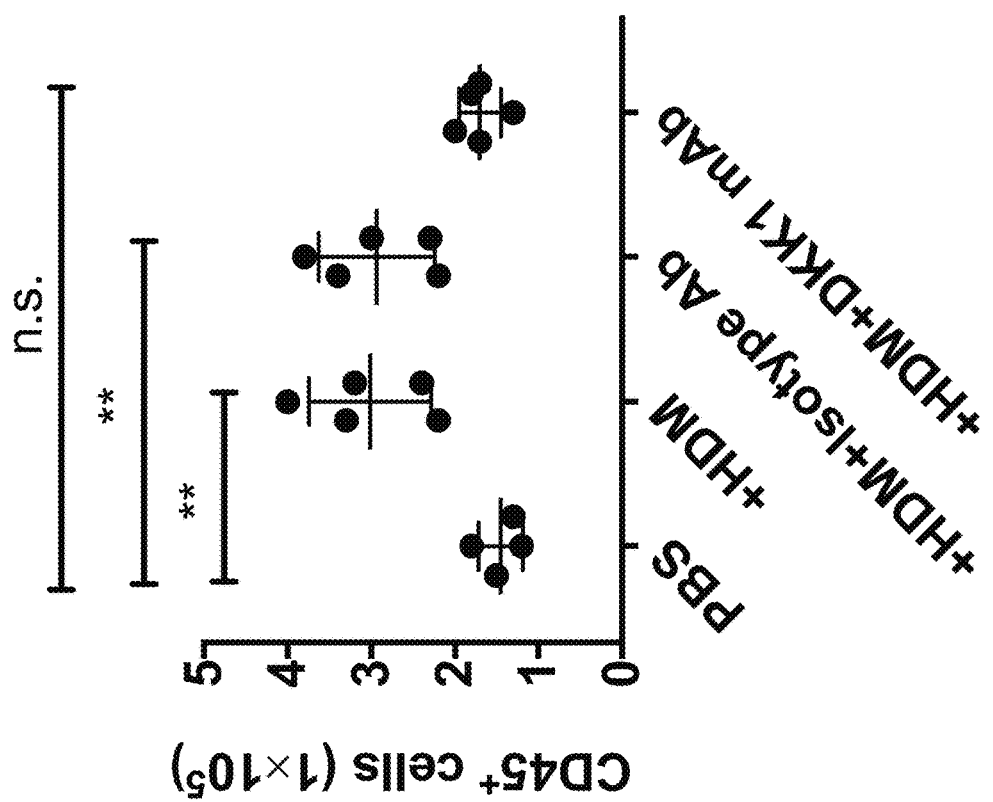
FIG. 18 depicts results of experiments showing a Dkk-1 monoclonal antibody treatment protects BALB/c mice from house dust mite (HDM)-induced asthma. Six-week-old female C57Bl/6 mice were treated with PBS(n=4), HDM (n=5), HDM and isotype antibody (n=5), and HDM plus Dkk-1 mAb (n=5). 10 μg of HDM was treated intranasally on day 0, 7, 8, 9, 10 and 11. Isotype antibody or Dkk-1 mAb was treated on day −1, +1, +6, +8, and +10. On day 14, mice were sacrificed and the lungs were harvested. fHCD45+ leukocytes were counted by flow cytometry. One-way-ANOVA analyses with Dunnet's post-hoc test was performed. **, p<0.005, n.s., not significant.

To determine the ability of an anti-Dkk-1 monoclonal antibody (Dkk-1 mAb) to protect BALB/c mice against chronic inflammation caused by *L. major*, 6-week old BALB/c mice were infected with *L.major* (2 million parasites/animal) on day 0. A Dkk-1 mAb or isotype control antibody (100 μg/injection) was injected intraperitoneally on day −1, +1, +3, +5, +7, +9, +11, +14 (n=6). On day 14, mice were sacrificed, and their draining lymph node cells were counted. Lesion size for each mouse was measured on day 12, 22, and 32. The Dkk-1 mAb reduced both the number of lymph node cells (FIG. 17A) and the lesion size on the feet of mice (FIG. 17B). These results indicate that the Dkk-1 mAb was able to protect BALB/c mice against chronic inflammation caused by *L. major*.

To determine the ability of a Dkk-1 mAb to protect BALB/c mice against HDM-induced asthma, 6-week old BALB/c mice were treated with PBS, HDM, HDM and an isotype antibody, or HDM and a Dkk-1 mAb. Mice treated with HDM or HDM and an isotype antibody had significantly increased levels of leukocytes (CD45+) compared to PBS treated mice. Conversely, mice treated with HDM and a Dkk-1 mAb did not have a significant change in leukocytes (CD45+) levels compared to PBS treated mice. These results suggest that the Dkk-1 mAB inhibition of Dkk-1 following allergen challenge inhibited the infiltration of leukocytes to the lung.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating a subject for or protecting a subject from type 2 inflammation the method comprising administering a composition comprising a compound selected from the group consisting of

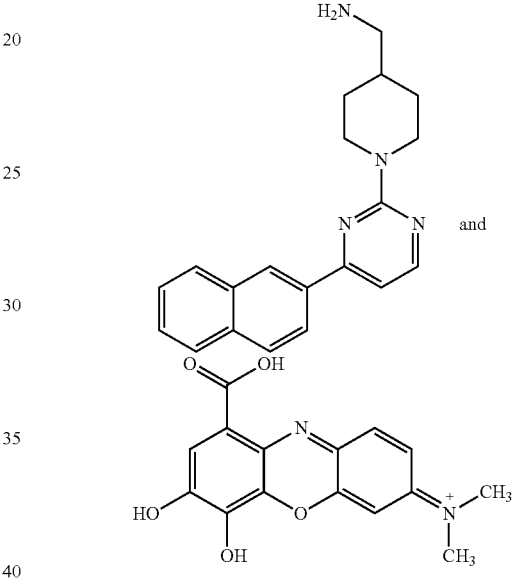

to the subject in need thereof.

2. The method of claim 1, wherein the method further comprises administering a second therapeutic agent.

3. The method of claim 2, wherein the second therapeutic agent is an inhibitor of type 2 inflammation.

4. The method of claim 3, wherein the inhibitor of type 2 inflammation is a glucocorticoid.

5. The method of claim 2, wherein the second therapeutic agent is selected from the group consisting of an asthma therapeutic, a parasite infection therapeutic and a cutaneous leishmaniasis therapeutic.

6. The method of claim 1, wherein the subject is a mammal.

7. The method of claim 6, wherein the mammal is a human.

* * * * *